(12) United States Patent
Kaminaka et al.

(10) Patent No.: US 9,175,295 B2
(45) Date of Patent: Nov. 3, 2015

(54) MODIFIED TRANSPOSON VECTOR AND ITS USE

(75) Inventors: Kazuyoshi Kaminaka, Kikuchi (JP); Hiroaki Maeda, Kikuchi (JP); Masaki Hirashima, Kikuchi (JP); Ryoichi Kawamura, Kikuchi (JP); Junichi Matsuda, Kikuchi (JP); Takashi Kuwana, Tsukuba (JP)

(73) Assignee: THE CHEMO-SERO-THERAPEUTIC RESEARCH INSTITUTE, Kumamoto (JP)

( * ) Notice: Subject to any disclaimer, the term of this patent is extended or adjusted under 35 U.S.C. 154(b) by 1736 days.

(21) Appl. No.: 11/994,982

(22) PCT Filed: Jul. 4, 2006

(86) PCT No.: PCT/JP2006/013302
§ 371 (c)(1),
(2), (4) Date: Jan. 7, 2008

(87) PCT Pub. No.: WO2007/004642
PCT Pub. Date: Jan. 11, 2007

(65) Prior Publication Data
US 2010/0281551 A1    Nov. 4, 2010

(30) Foreign Application Priority Data

Jul. 5, 2005 (JP) ................................. 2005-196398
Jul. 6, 2005 (JP) ................................. 2005-196957

(51) Int. Cl.
*C12N 15/79* (2006.01)
*C12N 5/10* (2006.01)
*C12N 15/85* (2006.01)

(52) U.S. Cl.
CPC ............... *C12N 15/79* (2013.01); *C12N 15/85* (2013.01); *C12N 2800/30* (2013.01); *C12N 2820/00* (2013.01)

(58) Field of Classification Search
CPC ............ C12N 2800/90; C12N 15/90; C12N 2800/30; A01K 2217/05; A01K 2227/706; A01K 67/0275; A01K 67/0339; A01K 2227/105; A01K 2267/03; A01K 2207/05; A01K 2217/052; A01K 2217/20; A01K 2227/106
USPC ...................................... 435/320.1, 69.1, 325
See application file for complete search history.

(56) References Cited

U.S. PATENT DOCUMENTS 6,140,129 A * 10/2000 Cox et al. ....................... 435/477
6,200,800 B1 * 3/2001 Choulika et al. ............ 435/320.1
7,745,218 B2 * 6/2010 Kim et al. ....................... 435/473

2003/0050258 A1 * 3/2003 Calos ............................... 514/44
2004/0077572 A1 * 4/2004 Hackett et al. .................. 514/44
2006/0212949 A1 * 9/2006 Alphey ........................... 800/13

FOREIGN PATENT DOCUMENTS

WO          03/031629 A1     4/2003

OTHER PUBLICATIONS

Xiao et al Genetics, 2000, 156, 2007-2017.*
Miskey, C., "DNA transposons in vertebrate functional genomics", CMLS Cellular and Molecular Life Sciences (2005), vol. 62, No. 6, pp. 629-641 XP019200959.
Ivics et al., "The Sleeping Beauty Transposable Element: Evolution, Regulation and Genetic Applications", Current Issues in Molecular Biology (2004), vol. 6, pp. 43-55 XP002520006.
Ivics et al., "Transposable Elements for Trangenesis and Insertional Mutagenesis in Vertebrates: A Contemporary Review of Experimental Strategies", Methods in Molecular Biology (2004), vol. 260, pp. 255-276 XP0001182472.
Araki et al., "Exchangeable Gene Trap Using the Cre/Mutated Lox System" Celluar Molecular Biology (1999), vol. 45, No. 5, pp. 737-750.
Shimizu et al., "Identification of cis-Regulatory Sequences in the Human Angiotensinogen Gene by Transgene Coplacement and Site-Specific Recombination", Molecular and Cellular Biology (2005), vol. 25, No. 8, pp. 2938-2945.
Chatterjee et al., "Selecting transpositions using phage P1 headful packaging: new markerless transposons for functionally mapping long-range regulatory sequences in bacterial artificial chromosomes and P1-derived artificial chromosomes", Analytical Biochemistry (2004), vol. 335, pp. 305-315.

(Continued)

*Primary Examiner* — Anoop Singh
(74) *Attorney, Agent, or Firm* — Browdy and Neimark, PLLC

(57) ABSTRACT

A modified transposon vector and a method for introducing a foreign gene into a cell are provided. A modified transposon vector wherein a nucleic acid fragment having the following features (a)-(b) or (a)-(c) is inserted; a cell expressing a foreign gene obtained by introducing said vector into chromosomal DNA of a cell line or an ontogenetic cell and further introducing an expression cassette of a foreign gene into the chromosomal DNA; a genetically recombined animal generated by using said cell (in case of an ontogenetic cell); and a method for producing a foreign protein from said cell and said genetically recombined animal:

(a) It consists of 5'- and 3'-TIR sequences of a transposon gene; (b) A sequence where a recombination reaction occurs is inserted between at least either of DR regions present by twos each in 5'- and 3'-TIR sequences of a transposon gene; (c) A restriction enzyme recognition site or an expression cassette of a foreign gene is inserted between 5'- and 3'-TIR sequences of a transposon gene.

17 Claims, 20 Drawing Sheets

(56) References Cited

OTHER PUBLICATIONS

Ivics et al., "Identification of Functional Domains and Evolution of Tc1-like Transposable Elements", Proc. Natl. Acad. Sci. USA (1996), vol. 93, No. 10, pp. 5008-5013.

Canestro et al., "Isolation and Characterization of the First Non-autonomous Transposable Element in Amphioxus, ATE-1", Gene (2003), vol. 318, pp. 69-73.

Araki et al., "Site-directed Integration of the cre gene mediated by Cre recombinase Using a Combination of Mutant lox sites", Nucleic Acids Research (2002), vol. 30, No. 19, pp. e103.

Soukharev et al., "Segmental Genomic Replacement in Embryonic Stem Cells by Double lox Targeting", Nucleic Acids Reaserach (1999), vol. 27, No. 18, pp. e21.

\* cited by examiner

Fig. 7

```
              10         20         30         40         50         60
       atgggaaaat caaaagaaat cagccaagac ctcagaaaaa aaatagtaga cctccacaag
              70         80         90        100        110        120
       tctggttcat ccttgggagc gatttccaaa cgcctcaagg taccacgttc atctgtgcaa
             130        140        150        160        170        180
       acaatagtac gcaagtataa acaccatggg accacgcagc cgtcttaccg atcaggaagg
             190        200        210        220        230        240
       agacgcgttc tgtctcctag agatgaacgt actttggtgc gtaaagttca atcaatccc
             250        260        270        280        290        300
       agaacaacag caaaggacct tgtgaagatg ctggaagaaa caggtacaaa agtatctata
             310        320        330        340        350        360
       tccacagtaa acgagtcct atatcgacat aacctgaaag gtcgctcagc aaggaagaag
             370        380        390        400        410        420
       ccactgctcc aaaaccgcca taaaaaagct agactacggt ttgcaactgc acatggagac
             430        440        450        460        470        480
       aaagatcgta cttttggag aaatgtcctc tggtctgatg aaacaaaaat agaactgttt
             490        500        510        520        530        540
       ggccataatg accatcgtta tgtttggagg aaaaaggggg aggcttgcaa gccgaagaac
             550        560        570        580        590        600
       accatcccaa ctgtgaagca cgggggtggc agcatcatgt tgtgggggtg ctttgctgca
             610        620        630        640        650        660
       ggaggaactg gtgcacttca caaatagat ggcattatga ggaaagaaaa ttatgtagat
             670        680        690        700        710        720
       atattgaagc aacatctcaa gacatcagtc aggaagttaa agcttggtcg caaatgggtc
             730        740        750        760        770        780
       ttccaaatgg acaatgaccc caaacatact tccaaagttg tggcgaaatg cttaaggac
             790        800        810        820        830        840
       aacaaagtca aggtattgga gtggccatca caaagccctg acctcaatcc tatagaaaat
             850        860        870        880        890        900
       ctgtgggcag aactgaaaaa gcgtgttcga gcaaggaggc ctacaaacct gactcagtta
             910        920        930        940        950        960
       caccagcttt gtcaggagga atgggccaaa attcacccaa cttattgtgg caagcttgtg
             970        980        990       1000       1010       1020
       gaaggctacc cgaaacgttt aacccaagtt aaacaattta aaggcaatgc taccaaatac
                 1030
       taa
```

Fig. 8

```
         10         20         30         40         50         60
MGKSKEISQD LRKKIVDLHK SGSSLGAISK RLKVPRSSVQ TIVRKYKHHG TTQPSYRSGR
         70         80         90        100        110        120
RRVLSPRDER TLVRKVQINP RTTAKDLVKM LEETGTKVSI STVKRVLYRH NLKGRSARKK
        130        140        150        160        170        180
PLLQNRHKKA RLRFATAHGD KDRTFWRNVL WSDETKIELF GHNDHRYVWR KKGEACKPKN
        190        200        210        220        230        240
TIPTVKHGGG SIMLWGCFAA GGTGALHKID GIMRKENYVD ILKQHLKTSV RKLKLGRKWV
        250        260        270        280        290        300
FQMDNDPKHT SKVVAKWLKD NKVKVLEWPS QSPDLNPIEN LWAELKKRVR ARRPTNLTQL
        310        320        330        340
HQLCQEEWAK IHPTYCGKLV EGYPKRLTQV KQFKGNATKY
```

Fig. 9

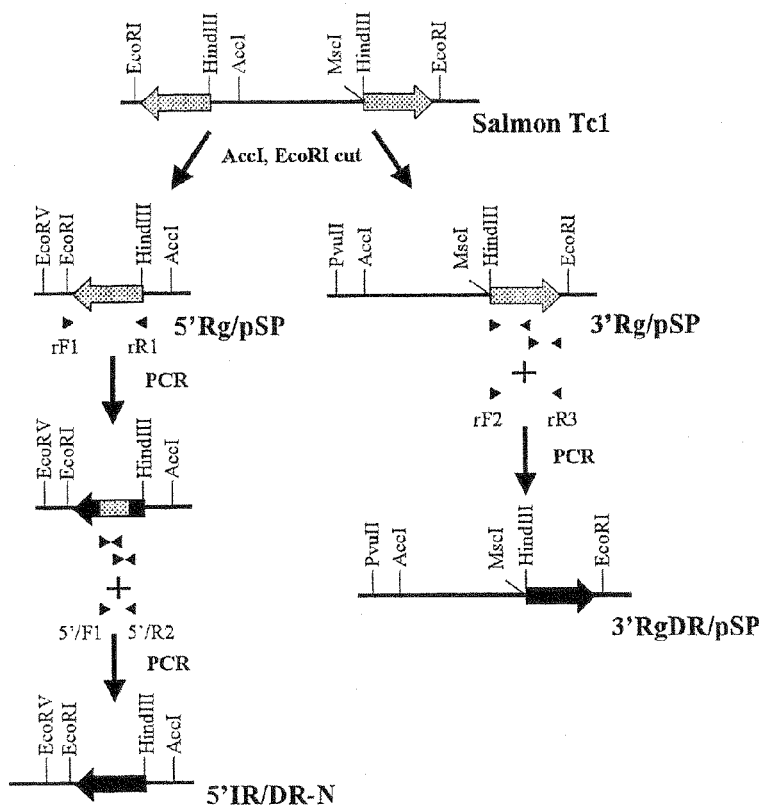

○;PolyA addition signal sequence

Photomicrograph　　GFP expression　　SSEA-1 expression
　　　　　　　　　　　　　　　　　　　　(Texas red)

Photomicrograph　　GFP expression

Photomicrograph　　GFP expression

MODIFIED TRANSPOSON VECTOR AND ITS USE

TECHNICAL FIELD

The present invention relates to a modified transposon vector obtained by gene recombination technique and use thereof. More particularly, the present invention relates to a modified transposon vector, which is reduced in capacity to transpose on a genome characteristic of transposon and which allows for introduction of a foreign gene of large size into cells, and use thereof.

BACKGROUND ART

Today, a gene introduction technique has made remarkable progress and become indispensable for production of a genetically recombined protein obtained by introducing a foreign gene into animal cells, production of genetically recombined organisms and a gene therapy.

The most important matter for a gene introduction technique is to efficiently introduce a gene of interest into cells and to express it stably. Normally, for obtaining animal cells or animal individuals expressing a gene of interest (hereinafter referred to as "recombinant"), a cassette for expressing said gene (a cassette consisting of a promoter, said gene and poly(A) addition signal sequence, hereinafter referred to as "expression cassette") and a cassette for expressing a drug resistant gene as a marker gene for the gene introduction are introduced into ontogenetic cells such as EG cells or ES cells and those recombinants stably expressing the introduced gene are selected. An instrument used for introducing the expression cassette of said gene and the cassette of the drug resistant gene into cells is called a vector. In order to efficiently obtain a recombinant stably expressing said gene, how efficiently said gene may be introduced into chromosomal DNAs of a host, i.e. cells or animal individual to which gene introduction is aimed, would become the crux and in this regard a kind of a vector to be used is the most important. What kind of a vector is used would greatly vary insertion efficiency into chromosomal DNAs of a host as well as efficiency of subsequent recombinant production.

Today, a vector utilized for introducing a gene of interest into animal cells or animal individual may largely be classified into a viral vector where a viral genome within viral particles is used and a non-viral vector. Characteristic features of both vectors are outlined hereinbelow in view of insertion into chromosomal DNAs.

A viral vector, as its name indicates, is one wherein an expression unit of a gene of interest is inserted into a viral genome to prepare a viral particle bearing said gene within its genome and said viral particle is infected to animal cells or a fertilized egg or occasionally directly to animal individual for introduction of said gene. This type of vector is further classified into a vector introducible into chromosomal DNAs of a host and a vector not introduced into chromosomal DNAs of a host but present as an episome. Examples of the former include oncoretrovirus, lentivirus and adeno-associated virus vectors. Examples of the latter include adenovirus and herpesvirus vectors.

These viral vectors are capable of introducing a gene of interest into cells with high efficiency since they utilize the ability to infect cells originally possessed by the virus. These viral vectors also have limitation in cellular species for introduction since they retain cellular species specificity originally possessed by the virus. Furthermore, when oncoretrovirus or lentivirus vector introducible into chromosomal DNAs of a host is used, there is a concern in safety such as contamination of an expression product of a gene of interest with viruses due to generation of replicable viral particles or production of innate retrovirus due to insertion of a reverse transcriptase into a genome.

On the other hand, a plasmid vector is primarily used as a non-viral vector. A plasmid vector is one where a plasmid, which was found as an extranuclear circular gene that is replicated and retained outside the E. coli chromosome, is used as a vector. A plasmid vector, even with insertion of a gene of interest, may easily be multiplied within E. coli and thus has commonly been used as a gene introduction vector for animal cells. However, a plasmid vector, which is a DNA per se, is difficult to be introduced into cells without physical treatment such as microinjection or electroporation. At present, other than the physical technique, the method for efficiently introducing a plasmid vector into cells includes calcium phosphate coprecipitation and complex formation with DEAE-dextran or cationic lipids. With these devises, efficiency of gene introduction into cells has gradually been improved but is still much inferior to the above method using a viral vector. Furthermore, the most important is that, when a gene of interest is introduced via a plasmid vector, a probability of insertion of said gene into chromosomal DNAs of a host is extremely low such that the vector transferred from cytoplasm into nucleus may accidentally be inserted while chromosomal replication. A plasmid vector, though with the defects described above, is superior to a viral vector from the aspect of safety and up till the present a recombinant obtained with this vector alone has been used for production of a recombinant protein.

In recent years, for improving one of the greatest drawbacks of a plasmid vector, i.e. poor insertion efficiency into chromosomal DNAs of a host, a vector utilizing a transposon has been developed which has an insertion mechanism into chromosomal DNAs of a host. A transposon, referring to a gene which transposes on a chromosome and has firstly been reported by Barbara McClintock, is found to be present on a chromosome of various organisms (e.g. Non-patent reference 1).

A transposon may largely be classified into two groups (cf. e.g. Non-patent reference 2). One is a retro transposon classified as class I and the other is a DNA transposon classified as class II. A class I retro transposon, present as a DNA on a chromosome, is once transcribed into an RNA which is then transformed into a complementary DNA (cDNA) by the function of a reverse transcriptase coded therein and the cDNA is re-inserted into a chromosome. Thus, this type of transposon tends to continually multiply its copies insofar as it has the activity. A retro transposon is further divided into two large groups based on the presence or absence of a reverse transcriptase. A retro transposon with no reverse transcriptase encoded therein is a non-autonomous transposon that is not capable of transposing by itself but transposes by borrowing an exogenous reverse transcriptase. The group with a reverse transcriptase encoded therein is further divided into two large groups based on the presence or absence of Long Terminal Repeat (LTR). A so-called retrovirus, which has an LTR sequence at the end of its genome and encodes a reverse transcriptase, is thought to be a kind of a retro transposon.

On the other hand, a class II DNA transposon is cleaved from the insertion site on a chromosome via the function of an enzyme catalyzing transposition, called transposase, encoded by itself and is re-inserted into different site. From such a mode of transposition, this type of transposon is also called "cut-and-paste" transposon. This type of transposon characteristically has a Terminal Inverted Repeat (TIR) of several to as long as several hundreds of bases at both ends of a transposon gene as well as a gene encoding transposase flanked by TIR sequences. A transposase as expressed recognizes and binds with the terminal TIR sequences and undertakes reactions of cleavage from chromosomal DNAs and insertion at a different site of the transposon to thereby allow for its transposition on a chromosome. A majority of transposons with the transposition activity has only been reported in bacteria, plants and insects with some exceptions. However, in 1997, Ivics et al. isolated a transposon from a salmon belonging to Tc1/mariner superfamily, repaired a gene encoding a transposase inactivated through accumulation of genetic mutations and eventually succeeded in regeneration of a transposase with the "cut-and-paste" activity, which is named "Sleeping Beauty" (cf. e.g. Non-patent reference 3). It was revealed that the "Sleeping Beauty" has the transposition activity not only in cells derived from fish but also in cells derived from mammals and its introduction rate into chromosomal DNAs reached a level of 80-folds higher than that of usual transfection (cf. e.g. Non-patent reference 4).

Table 1 shows active transposons belonging to Tc1/mariner superfamily reported up till the present. Among the active transposons shown therein, the "Sleeping Beauty" was revealed to have the highest transposition activity (cf. e.g. Non-patent reference 5) and, with the benefit of its property that no host-derived factor is necessary for expression of the transposition activity, is going to be used as a non-viral, efficient vector for gene introduction into animal cells or animal individual.

TABLE 1

Major transposons belonging to Tc1/mariner superfamily

| Superfamily | family | subfamily | TIR length | Organism |
|---|---|---|---|---|
| Tc1/mariner | Tc1 | Tc1 | 54 | *Caenorhabditis elegans* |
| | | Tc3 | 462 | *Caenorhabditis elegans* |
| | | Sleeping Beauty | 225 | Atlantic salmon |
| | mariner | Minos | 255 | *Drosophila hydei* |
| | | Mos1 | 28 | *Drosophila mauritiana* |
| | | Himar1 | 31 | *Haematobia irritans* |

A transposon vector system developed by Ivics et al. is such that a plasmid, wherein an expression unit of a gene of interest is inserted into a transposon vector having at both ends TIR sequences derived from white cloud mountain minnow (*Tanichthys albonubes*), and a plasmid, wherein an expression unit of a transposase ("Sleeping Beauty") necessary for transposition into chromosomal DNAs is inserted into a transposon vector, are simultaneously introduced into cells. With this method, those clones alone having a gene of interest in chromosomal DNAs of cells are selected so as to avoid, as characteristic feature of transposon, transposition after insertion into chromosomal DNAs. Besides, a transposon vector used in this system has relatively long TIR sequences, characteristic of Tc3 among Tc1/mariner superfamily, in which two transposase-binding sequences called "Direct Repeat (DR)" are present (FIG. 1).

As outlined above, a transposon vector, typically "Sleeping Beauty", exhibits high insertion efficiency into chromosomal DNAs as well as a broad host spectrum in spite of a non-viral vector and thus is expected to be increasingly used as a vector for gene introduction in future.

While such a development of a vector for gene introduction has much progress, a great progress is also seen in a technique for inserting a gene at a specific site on DNAs or for providing deletion or replacement of a specific gene. A typical example of such techniques is to use a recombination mechanism called "Cre-Lox" and "Flp-FRT" recombination systems.

Cre-Lox recombination system is an application of a recombination mechanism found in bacteriophage P1 consisting of two elements, i.e. LoxP sequences consisting of 34 bases where recombination occurs and Cre, an enzyme (recombinase) undertaking a recombination reaction. In a recombination reaction with wild-type LoxP, in the presence of Cre, there may occur both a reaction wherein a DNA sequence flanked by LoxP sequences is deprived and a reaction wherein a circular DNA having LoxP sequences is inserted into LoxP sequences present on a different DNA. However, with wild-type LoxP, the reaction of deprivation of a DNA sequence flanked by LoxP sequences preferentially occurs as compared to the insertion reaction into LoxP sequences and thus it will be hard to expect the latter reaction to occur (FIG. 2). Today, in order to solve this problem, mutated LoxP sequences have been prepared and applied for insertion reaction or replacement reaction not expected with wild-type LoxP. Table 2 shows major mutated Lox sequences being used and their mutated sites. Cre-Lox system with these mutated Lox sequences has allowed for efficient DNA insertion at Lox sequences or replacement of a DNA sequence between Lox sequences (FIG. 3),

TABLE 2

Major mutated Lox sequences

| Name | Cre-binding site | Spacer | Cre-binding site | Type of mutation |
|---|---|---|---|---|
| LoxP | ATAACTTCGTATA | GCATACAT | TATACGAAGTTAT | Wild type |
| Lox71 | TACCGTTCGTATA | GCATACAT | TATACGAAGTTAT | LE mutant |
| Lox66 | ATAACTTCGTATA | GCATACAT | TATACGAA CGGTA | RE mutant |
| Lox 2272 | ATAACTTCGTATA | G GATAC TT | TATACGAAGTTAT | Spacer mutant |
| Lox 511 | ATAACTTCGTATA | G TACAT | TATACGAAGTTAT | Spacer mutant |

*: The underlined sequences indicate mutations from those of wild type.

Flp-FRT recombination system is an application of a recombination mechanism found in yeast (*Saccharomyces cerevisiae*) which consists of, like Cre-Lox system, two elements, i.e. FRT sequences consisting of 48 bases where recombination occurs and Flp, a recombinase undertaking a recombination reaction. With this recombination system, it is also possible to remove a DNA sequence flanked by FRT sequences through deprivation reaction or to insert a circular DNA having FRT sequences into FRT sequences.

Thus, once a specific sequence could be inserted into chromosomal DNAs, it is now possible to induce insertion, deprivation or replacement reaction of a gene on a specific region, i.e. on a sequence where a recombination reaction occurs, by utilizing the recombination systems as described above.

Non-patent reference 1: Richardson R D et al., *Stem Cells*, 20, 105-118, 2002

Non-patent reference 2: Finnegan, *Curr. Opin. Genet. Dev.*, 2, 861-867, 1992

Non-patent reference 3: Ivics Z et al., *Cell*, 91, 501-510, 1997
Non-patent reference 4: Yant S R et al., *Nat. Genet.*, 25, 35-41, 2000
Non-patent reference 5: Sylvia E J et al., *Proc. Natl. Acad. Sci. USA*, 98, 6759-6764, 2001

DISCLOSURE OF THE INVENTION

Technical Problem to be Solved by the Invention

As described above, among vectors for gene introduction into chromosomal DNAs of cells, systems with a transposon vector belonging to Tc1/mariner superfamily and "Sleeping Beauty" are expected to increasingly be used as a vector that is safe and has high introduction efficiency but bear problems as described below.

The first problem is that a gene size to be expected for insertion into chromosomal DNAs by the transposon activity has limitation. As reported, with a system using "Sleeping Beauty" which has the highest efficiency of gene introduction among transposon vectors, the larger a DNA size to be inserted becomes, the lower its efficiency of gene introduction with the efficiency being extremely decreased when a DNA size to be inserted exceeds 6 kbp (*J. Mol. Biol.*, 302, 93-102, 2000). For a gene introduction, in addition to a gene of interest, a promoter for transcription of its mRNA and a poly(A) addition signal sequence for stabilization of the transcribed mRNA are also necessary. Therefore, limitation in a size of 6 kbp, when expression of a gene of interest is intended, will result in restriction in a kind of genes to be inserted. Also, in case of some genes where an active protein is not produced until several peptides encoded are associated to form a polymer, insertion of several expression cassettes will be required for expressing a protein in an active form. Furthermore, for selecting cells or animal individual with a gene of interest inserted therein, an expression cassette of a drug resistance gene to confer resistance to a lethal drug needs simultaneously be inserted. As such, in case of introduction of plural genes into cells, a necessary number of gene expression cassettes are each inserted into separate plasmids which are then simultaneously introduced into cells. However, in case of a transposon vector, it is believed that only one copy of an expression cassette may be inserted into chromosomal DNAs. Thus, in view of its mechanism for insertion, it is likely that only one of the expression cassettes introduced simultaneously into cells may be inserted into chromosomal DNAs.

Besides, recombinant products useful for a medical drug include those wherein a gene encoding a single protein alone exceeds 8 kbp (*Science*, 228, 1401-, 1985, *Nature*, 312, 330-). For expression of such a big gene, it is impossible to introduce genes in separate plural vectors as described above and in this sense limitation in a size of an introducible gene would be fatal.

The second problem is the presence of possibility that a gene inserted by a transposon vector may transpose on chromosomal DNAs. For gene introduction into cells or individual, a vector should have the following requisites: firstly, it has high introduction efficiency; secondly, a gene introduced is stably expressed; and thirdly, it is safe. Among these requisites, it is safety without a concern of viral particles formation that a transposon vector is superior to a viral vector such as oncoretrovirus or lentivirus. A transposon vector, as exploiting the property of a transposon to transpose on chromosomal DNAs, through which property a transposon was discovered, would be present on chromosomal DNAs retaining the competence to transpose on chromosomal DNAs after introduction therein. Supposing that there is a possibility of contamination of a recombinant protein as an expression product with such a transposon vector that retains the above competence, it is envisaged that a concern for safety will arise to thereby restrict its use like a viral vector.

As described hereinabove, expression of a transposase in addition to TIR sequences is necessary for enabling a transposon to transpose. Thus, as Ivics et al. did, it is possible to select animal cells or individual with a gene of interest alone being inserted therein by separately introducing a plasmid wherein a transposon vector bearing a gene of interest flanked by TIR sequences is inserted and a plasmid wherein an expression cassette of a transposase is inserted. Generally speaking, it is envisaged that the transposition activity may be deprived by eliminating one of the elements necessary for transposition of DNAs, i.e. a transposase.

As characteristic features of a DNA transposon, if a transposon with the capacity of autonomous transposition, expressing an active transposase, is present within the same genome, a non-autonomous transposon, lacking the transposase activity, is also capable of transposing. In other words, as far as an active transposase is provided, a transposon may be said to retain the transposition activity. In fact, in cyprinodont wherein non-autonomous Tol1 transposon belonging to hAT family was introduced, said transposon was found to transpose within a genome (*Protein Nucleic acid Enzyme* 49, 2103-2110, 2004). The cause of this recurrence of transposition, though not fully elucidated, might be: 1) an inactivated transposase present in a host's genome is reconstructed into an active form through spontaneous mutagenesis; and 2) a transposon with the transposition activity invaded from other species. The invasion from other species of a transposon with the transposition activity fairly likely to occur viewing that hobo transposase belonging to hAT family has an ability to let Hermes belonging to the same hAT family transpose (*Insect Mol. Biol.*, 8, 359-, 1999). For Tc1/mariner superfamily to which "Sleeping Beauty" belongs, such a cross-transposition reaction is not directly proved. However, in view of the fact that transposons of this family are present in an active state in various animal species, there is no fully denying a possibility of recurring transposition of said transposon vector within a genome (*Insect Biochem. Mol. Biol.*, 34, 121-, 2004).

Insofar as there is a possibility of recurring transposition via the mechanism described above, it is foreseen that recurring transposition of an introduced transposon vector cannot be prevented merely by selecting animal cells or individual which does not bear an active transposase.

Recurring transposition of an introduced transposon vector, which implies alteration of its position within chromosomal DNAs, would induce reduction in an expression level, called "positional effect", in animal cells which acquired a high expression level through selection. On the other hand, in an animal individual, it not only affects to an expression level of an introduced gene but also to even survival of said individual depending on the site of recurring transposition. On assessing safety of a recombinant protein as an expression product, a possibility of recurring transposition implies that denial of a possibility of contamination of a final product with an introduced transposon vector and of its insertion into human chromosomal DNAs becomes necessary. It is easily envisaged that this concern of recurring transposition would be a serous obstacle especially when a transposon vector is exploited as a vector for a gene therapy.

As described above, conventional transposon vector systems such as "Sleeping Beauty" have problems when used as a vector for gene introduction into animal cells and individual. Thus, the problems need be overcome in order that the transposon vector systems may widely be used not only for preparing cells expressing a foreign gene but also for producing a recombinant medical drug or generating a genetically recombined animal.

Accordingly, an object of the present invention is to provide a modification of a transposon vector (hereinafter referred to as "modified transposon vector") for introducing a foreign gene into cells, which vector allows for overcoming the problems as described above.

Another object of the present invention is to provide a method for introducing a foreign gene of a large size into cells while suppressing the competence to transpose on a genome characteristic of a transposon by using the modified transposon vector as described above.

Means for Solving the Problems

Under the circumstances, the present inventors have earnestly continued research in order to solve the problems described above and as a result have found that a transformation efficiency (introduction efficiency into cells) observed when a transposon vector having a nucleic acid fragment, wherein an expression cassette of a puromycin resistant enzyme gene is inserted between 5'- and 3'-TIR sequences of a transposon gene, and a plasmid expressing a transposase are introduced together into HeLa cells is identical to that observed when a modified transposon vector having the nucleic acid fragment, wherein Lox sequence is inserted between DR regions of at least one of 5'- and 3'-TIR sequences, and the plasmid are introduced together into cells.

Furthermore, to the HeLa cells where the modified transposon vector has been introduced therein, the present inventors have introduced a plasmid (hereinafter also referred to as "donor plasmid") comprising an expression cassette of jellyfish green fluorescent protein (GFP)/aminoglycoside 3' phosphotransferase (neo) genes with addition of Lox sequences at both ends together with an expression plasmid of Cre gene and have found that the puromycin resistant enzyme gene was replaced with GFP/neo genes and that no transposition activity was observed for the thus replaced genes even in the presence of a transposase to thereby complete the present invention.

Thus, the present invention provides a modified transposon vector, a method for expressing a foreign gene by using said vector, transformed cells and a genetically recombined animal obtained by said method as described hereinbelow.

1. A modified transposon vector wherein a nucleic acid fragment having the following features (a)-(b) or (a)-(c) is inserted:
   (a) It consists of 5'- and 3'-TIR sequences of a transposon gene;
   (b) A sequence where a recombination reaction occurs is inserted between at least either of DR regions present by twos each in 5'- and 3'-TIR sequences of a transposon gene;
   (c) A restriction enzyme recognition site or an expression cassette of a foreign gene is inserted between 5'- and 3'-TIR sequences of a transposon gene.
2. The modified transposon vector of 1 wherein the 5'- and 3'-TIR sequences of a transposon gene are SEQ ID NOs: 1 and 2, respectively.
3. The modified transposon vector of 1 or 2 wherein the sequence where a recombination reaction occurs is Lox or FRT sequence.
4. The modified transposon vector of 3 wherein at least one of the Lox sequence is a mutated Lox sequence.

5. The modified transposon vector of 4 wherein said Mutated Lox sequence is selected from the group consisting of Lox71, Lox66, Lox2272 and Lox511 sequences.
6. The modified transposon vector of 4 or 5 wherein LoxP, Lox71, Lox66, Lox2272 and Lox511 sequences are SEQ ID NOs: 3, 4, 5, 6 and 7, respectively.
7. A method for producing a foreign protein which comprises introducing a modified transposon vector, wherein a nucleic acid fragment having the following features (a)-(b) or (a)-(c) is inserted, into cells, culturing the resulting cells expressing a foreign gene, and recovering an expressed foreign protein:
   (a) It consists of 5'- and 3'-TIR sequences of a transposon gene;
   (b) A sequence where a recombination reaction occurs is inserted between at least either of DR regions present by twos each in 5'- and 3'-TIR sequences of a transposon gene;
   (c) A restriction enzyme recognition site or an expression cassette of a foreign gene is inserted between 5'- and 3'-TIR sequences of a transposon gene.
8. A method for producing a foreign protein which comprises culturing cells expressing a foreign gene obtained by the following steps (1)-(4):
   (1) Introducing a modified transposon vector, wherein a nucleic acid fragment having the following features (a)-(b) or (a)-(c) is inserted, into cells:
      (a) It consists of 5'- and 3'-TIR sequences of a transposon gene;
      (b) A sequence where a recombination reaction occurs is inserted between at least either of DR regions present by twos each in 5'- and 3'-TIR sequences of a transposon gene;
      (c) A restriction enzyme recognition site or an expression cassette of a foreign gene is inserted between 5'- and 3'-TIR sequences of a transposon gene,
   (2) Cloning the resulting transformed cells,
   (3) Introducing an expression cassette of a foreign gene with addition of the sequence where a recombination reaction occurs as described in (1)(b) above at either both ends or at any one thereof, and
   (4) Culturing the cells expressing the foreign gene.
9. The method of 7 or 8 wherein the 5'- and 3'-TIR sequences of a transposon gene are SEQ ID NOs: 1 and 2, respectively.
10. The method of any one of 7 to 9 wherein the sequence where a recombination reaction occurs is Lox or FRT sequence.
11. The method of 10 wherein at least one of the Lox sequence is a mutated Lox sequence.
12. The method of 11 wherein said mutated Lox sequence is selected from the group consisting of Lox71, Lox66, Lox2272 and Lox511 sequences.
13. The method of 11 or 12 wherein LoxP, Lox71, Lox66, Lox2272 and Lox511 sequences are SEQ ID NOs: 3, 4, 5, 6 and 7, respectively.
14. The method of any one of 7 to 13 wherein said modified transposon vector and an expression plasmid of a transposase gene are introduced together into cells.
15. The method of any one of 7 to 13 wherein the modified transposon vector, in which an expression plasmid of a transposase gene is introduced, is used.
16. The method of any one of 8 to 15 wherein said expression cassette of a foreign gene and an expression plasmid of a Cre gene are introduced together into cells.
17. The method of any one of 8 to 15 wherein the expression cassette of a foreign gene, in which an expression plasmid of a Cre gene is introduced, is used.
18. The method of any one of 7 to 17 wherein said cells expressing a foreign gene are selected from the group consisting of HeLa, Vero, CHO, 293, BHK and SP2/0 cells.

19. A transformed cell in which a modified transposon vector, wherein a nucleic acid fragment having the following features (a)-(b) or (a)-(c) is inserted, is incorporated, or said transformed cell in which an expression cassette of a foreign gene with addition of the sequence where a recombination reaction occurs as described in (b) below at either both ends or at any one thereof is further incorporated:

(a) It consists of 5'- and 3'-TIR sequences of a transposon gene;

(b) A sequence where a recombination reaction occurs is inserted between at least either of DR regions present by twos each in 5'- and 3'-TIR sequences of a transposon gene;

(c) A restriction enzyme recognition site or an expression cassette of a foreign gene is inserted between 5'- and 3'-TIR sequences of a transposon gene.

20. The transformed cell of 19 which expresses a foreign gene.

21. The transformed cell of 19 or 20 wherein the 5'- and 3'-TIR sequences of a transposon gene are SEQ ID NOs: 1 and 2, respectively.

22. The transformed cell of any one of 19 to 21 wherein the sequence where a recombination reaction occurs is Lox or FRT sequence.

23. The transformed cell of 22 wherein at least one of the Lox sequence is a mutated Lox sequence.

24. The transformed cell of 23 wherein said mutated Lox sequence is selected from the group consisting of Lox71, Lox66, Lox2272 and Lox511 sequences.

25. The transformed cell of 23 or 24 wherein LoxP, Lox71, Lox66, Lox2272 and Lox511 sequences are SEQ ID NOs: 3, 4, 5, 6 and 7, respectively.

26. The transformed cell of any one of 19 to 25 wherein said cells expressing a foreign gene are selected from the group consisting of HeLa, Vero, CHO, 293, BHK and SP2/0 cells.

27. The transformed cell of any one of 19 to 25 which is an ontogenetic cell.

28. The transformed cell of 27 wherein said ontogenetic cell is selected from the group consisting of a fertilized egg, a blastomere up to the blastocyst stage, an ES cell, an EG cell and a primordial germ cell (PGC) derived from mammal, bird, fish and non-vertebrate animal.

29. A genetically recombined animal generated by using either an ontogenetic transformed cell expressing a foreign gene in which a modified transposon vector, wherein a nucleic acid fragment having the following features (a)-(c) is inserted, is incorporated, or an ontogenetic transformed cell expressing a foreign gene in which a modified transposon vector, wherein a nucleic acid fragment having the following features (a)-(b) or (a)-(c) is inserted, is incorporated and in which an expression cassette of a foreign gene with addition of the sequence where a recombination reaction occurs as described in (b) below at either both ends or at any one thereof is further incorporated:

(a) It consists of 5'- and 3'-TIR sequences of a transposon gene;

(b) A sequence where a recombination reaction occurs is inserted between at least either of DR regions present by twos each in 5'- and 3'-TIR sequences of a transposon gene;

(c) A restriction enzyme recognition site or an expression cassette of a foreign gene is inserted between 5'- and 3'-TIR sequences of a transposon gene.

30. The genetically recombined animal of 29 wherein the 5'- and 3'-TIR sequences of a transposon gene are SEQ ID NOs: 1 and 2, respectively.

31. The genetically recombined animal of 29 or 30 wherein the sequence where a recombination reaction occurs is Lox or FRT sequence.

32. The genetically recombined animal of 31 wherein at least one of the Lox sequence is a mutated Lox sequence.

33. The genetically recombined animal of 32 wherein said mutated Lox sequence is selected from the group consisting of Lox71, Lox66, Lox2272 and Lox511 sequences.

34. The genetically recombined animal of 32 or 33 wherein LoxP, Lox71, Lox66, Lox2272 and Lox511 sequences are SEQ ID NOs: 3, 4, 5, 6 and 7, respectively.

35. The genetically recombined animal of any one of 29 to 34 wherein said ontogenetic cell is selected from the group consisting of a fertilized egg, a blastomere up to the blastocyst stage, an ES cell, an EG cell and a primordial germ cell (PGC) derived from mammal, bird, fish and non-vertebrate animal.

36. The genetically recombined animal of any one of 29 to 35 which is chicken.

(More Efficacious Effects than Prior Art)

According to the method of the present invention, a modified transposon vector retaining high introduction efficiency into cells is provided. A modified transposon vector of the present invention, since a sequence where a recombination reaction occurs such as Lox or FRT sequence is inserted into at least either of 5'- and 3'-TIR sequences of a transposon gene, may be subject to destruction of the activity to transpose on a cellular chromosome, as originally possessed by a transposon vector, by utilizing a recombination system which is selected depending on the sequence where a recombination reaction occurs. Also, a modified transposon vector of the present invention, as comprising a restriction enzyme recognition site therein, may be inserted with a foreign gene at said site so that cells or animal cell may express said foreign gene.

Besides, according to the method of the present invention, a modified transposon vector is once introduced into cells, a Cre-Lox recombination system is then used as a recombination system to allow for the use of a mutated Lox sequence to thereby provide a method for efficiently replacing a foreign gene with another gene to be inserted. This enables efficient insertion of a large size gene of more than 6 kbp into a specific site within chromosomal DNAs of cells, which had been difficult with a conventional transposon vector. Accordingly, a foreign gene may efficiently be replaced and cells or a genetically recombined animal expressing a foreign gene with a high expression rate may be obtained more efficiently than before.

BRIEF DESCRIPTION OF DRAWINGS

FIG. 7 shows a nucleotide sequence of a transposase gene.

FIG. 8 shows an amino acid sequence of a transposase gene.

FIG. 9 is a schematic illustration showing process of isolation and repair of TIR sequence.

BEST MODE FOR CARRYING OUT THE INVENTION

Figure 1:
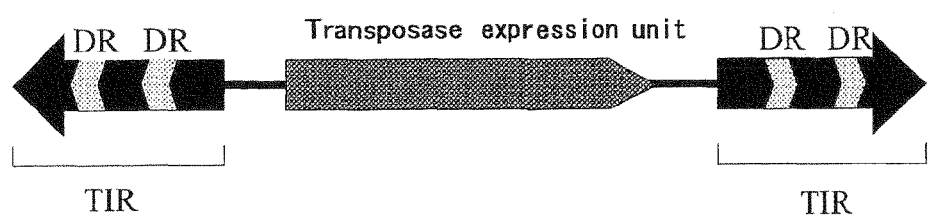
FIG. 1 shows a basic structure of a Tc3 transposon belonging to Tc1/mariner superfamily.
Figure 2:
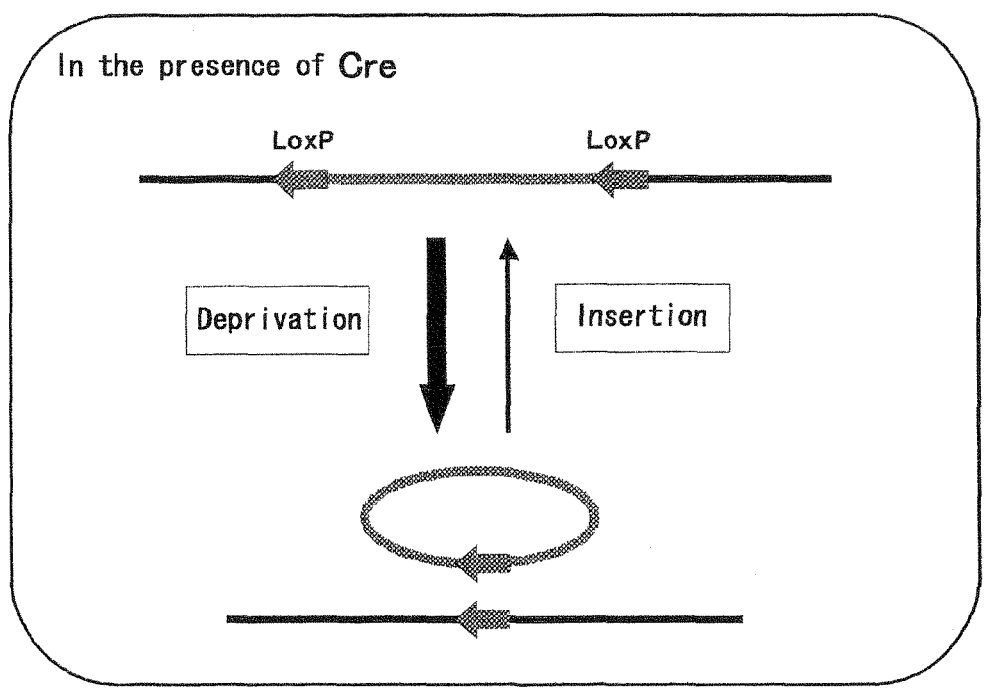
FIG. 2 shows a recombination mode in Cre-Lox system.
Figure 3:
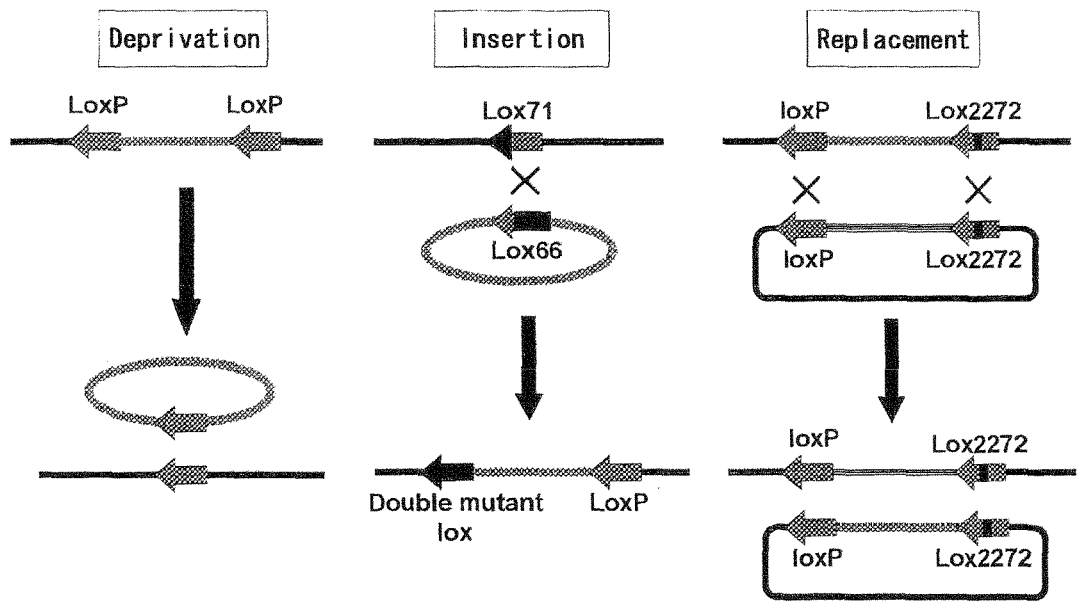
FIG. 3 shows major use of Cre-Lox system.

A modified transposon vector of the present invention is a transposon vector having two TIR sequences between which an appropriate restriction enzyme recognition site is present for inserting a genetic region (an expression cassette of a gene) for expression of a foreign gene. The present invention is characterized by a modified transposon vector having a nucleic acid fragment consisting of 5'- and 3'-TIR sequences of a transposon gene wherein a sequence where a recombination reaction occurs such as a Lox sequence is inserted between at least either of DR regions present by twos each in 5'- and 3'-TIR sequences of a transposon gene; a method for expressing a foreign gene in cells by using said modified transposon vector; a method for expressing a foreign gene in a genetically recombined animal generated by using ontogenetic cells which bear a foreign gene and are obtained by introducing said modified transposon vector; and further a method for expressing a foreign gene which comprises, once said modified transposon vector is introduced into cells including ontogenetic cells, destroying at least either of 5'- and 3'-TIR sequences by inserting or replacing with an expression cassette of a foreign gene or by depriving an unnecessary gene such as a drug marker gene with a recombination system such as Cre-Lox system.

1. Transposon Vector (IR/DR-NTA-Ad/pSP)

For use in a transposon vector, any transposon from any species may be used as far as it has the insertion activity and is preferably such a type of transposon that has two DR regions within a TIR sequence, e.g. Tc3 transposon. A preferable example includes a transposon from a salmon. The vector of the present invention is such that an appropriate restriction enzyme recognition site for inserting an expression cassette of a gene for expression of a foreign gene is added between these two TIR sequences.

(1) Isolation of 5'- and 3'-TIR Sequences of a Transposon Gene

Isolation of 5'- and 3'-TIR sequences of a transposon gene may be done as in the isolation of a transposase gene. For a primer, a primer (SEQ ID NO: 8) synthesized as reported by A. D. Radice et al. (*Mol. Gen. Genet.* 244, 606-, 1994) may be used. PCR is performed with said primer to amplify an inactivated transposon gene of about 1.6 kbp comprising both 5'- and 3'-TIR sequences. The amplified gene is once cloned into a plasmid pCR2.1, which is then digested with restriction enzymes EcoRI and AccI. The resulting DNA fragments of about 0.4 kbp and about 1.2 kbp are subcloned into a cloning vector pSP72 (Promega) to provide a plasmid (5'Rg/pSP) containing 5'-TIR sequence and a plasmid (3'Rg/pSP) containing 3'-TIR sequence, respectively.

These TIR sequences are compared with TIR sequence (EMBL/GenBank accession No. L48685) from *Tanichthys albonubes* (white cloud mountain minnow in Japanese) as reported by Ivics et al. (*Cell*, 91, 501-, 1997) and, if there is any difference, are repaired to be in conformity therewith. When the TIR sequences of 5'Rg/pSP and 3'Rg/pSP are mutated as compared to the TIR sequence reported by Ivics et al. (*Cell*, 91, 501-, 1997), they need be repaired.

The 5'-TIR sequence according to the present inventors may be repaired e.g. as described below. PCR with primers IR/DR rF1 (SEQ ID NO: 9) and IR/DR rR1 (SEQ ID NO: 10) is performed to amplify a DNA fragment of about 0.3 kbp which is cloned into a plasmid (pCR2.1). The plasmid is digested with restriction enzymes EcoRI and HindIII and the resulting fragment is inserted into 5'Rg/pSP, which has previously been digested with the same restriction enzymes and then dephosphorylated (BAP), to construct 5'RgDR/pSP. Using this as a template, PCR is performed with combinations of primers for repair, IR/DR-5'/F1 (SEQ ID NO: 11) and IR/DR-5'/R1 (SEQ ID NO: 12), and IR/DR-5'/F2 (SEQ ID NO: 13) and IR/DR-5'/R2 (SEQ ID NO: 14), to provide DNA fragments of about 100 bp and about 160 bp. An equivalent amount of these DNA fragments are mixed together and, after denaturation (at 70° C. for 10 min.), the mixture is gradually cooled to room temperature for annealing. Using the homologous DNA sequences annealed between both the DNA fragments as a template, PCR is again performed with the primers as described above, IR/DR-5'/R1 and IR/DR-5'/R2, to provide a DNA fragment of about 240 bp which is cloned into a plasmid (pCR2.1). The plasmid is digested with restriction enzymes AflII and HindIII and the resulting fragment is inserted into 5'RgDR/pSP, which has previously been digested with the same restriction enzymes and then BAP treated, to construct a plasmid 5'IR/DR-N having the 5'-TIR sequence.

The 3'-TIR sequence may be repaired e.g. as described below. Using 3'Rg/pSP as a template, PCR with combinations of primers for repair, IR/DR rF2 (SEQ ID NO: 15) and IR/DR rR2 (SEQ ID NO: 16), and IR/DR rF3 (SEQ ID NO: 17) and IR/DR rR3 (SEQ ID NO: 18), is first performed to amplify each of DNA fragments of about 200 bp. An equivalent amount of these DNA fragments are mixed together and the mixture is treated for annealing as described above. Using this DNA as a template, PCR is again performed with the primers as described above, IR/DR rF2 and IR/DR rR3, to provide a DNA fragment of about 370 bp which is cloned into a plasmid (pCR2.1). The plasmid is digested with restriction enzymes EcoRI and MscI and the resulting fragment is inserted into 3'Rg/pSP, which has previously been digested with the same restriction enzymes and then BAP treated, to construct a plasmid 3'RgDR/pSP having the 3'-TIR sequence. Nucleotide sequences of the DR regions of the 5'- and 3'-TIR sequences as repaired are identical to those of the DR regions from *Tanichthys albonubes* (white cloud mountain minnow in Japanese) except for one nucleotide of the inner DR of the 3'-TIR sequence and have the sequences of SEQ ID NO: 19 and SEQ ID NO: 20, respectively.

(2) Construction of a Transposon Vector IR/DR-NTA-Ad/pSP

Figure 4:
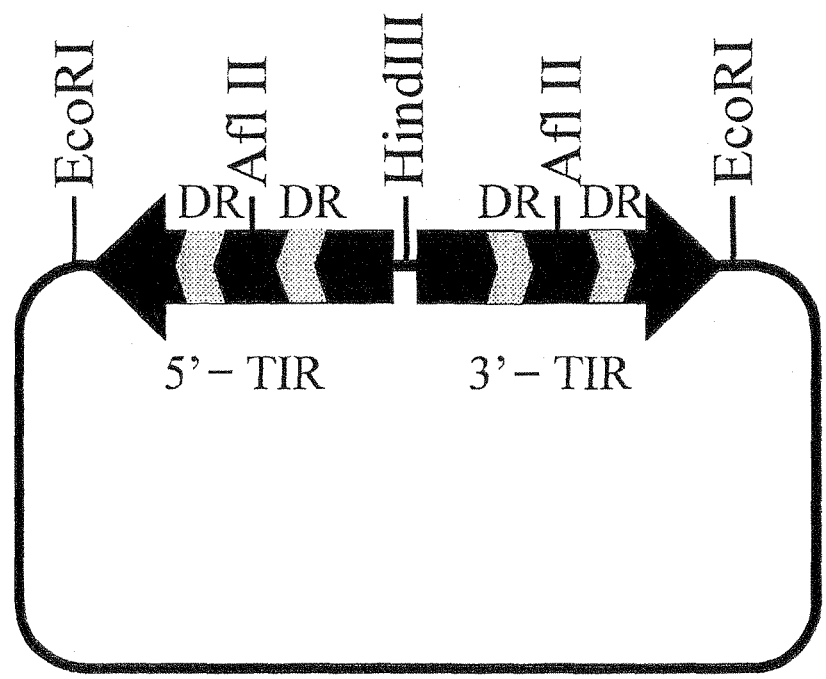
FIG. 4 shows a structure of a transposon vector IR/DR-N.

First, a DNA fragment comprising the 5'-TIR sequence obtained by digesting 5'IR/DR-N with restriction enzymes HindIII and EcoRV is inserted into 3'RgDR/pSP comprising the 3'-TIR sequence, which has previously been digested with restriction enzymes HindIII and PvuII and then BAP treated, to construct IR/DR-N comprising both the 5'- and 3'-TIR sequences (FIG. 4).

Next, IR/DR-N is treated as described below for inserting an adaptor having several restriction enzymes recognition sites into the HindIII cleavage site. First, an equivalent amount of primers, 5'IR/DR-AdF (SEQ ID NO: 21) and 5'IR/DR-AdR (SEQ ID NO: 22), phosphorylated at the 5' end, are mixed together and annealed to provide an adaptor 5'IR/DR-Ad where both primers are annealed. In like manner, an adaptor 3'IR/DR-Ad is obtained where 3'IR/DR-AdF (SEQ ID NO: 23) and 3'IR/DR-AdR (SEQ ID NO: 24) are annealed. Then, an equivalent amount of 5'IR/DR-Ad and 3'IR/DR-Ad are mixed together, reacted at 16° C. for 30 min. using DNA Ligation Kit (TaKaRa) and precipitated with ethanol to recover a DNA fragment wherein both adaptors are bound. This DNA fragment is digested with restriction enzyme HindIII and inserted into HindIII site of IR/DR-N previously constructed to construct IR/DR-N-Ad.

Figure 5:
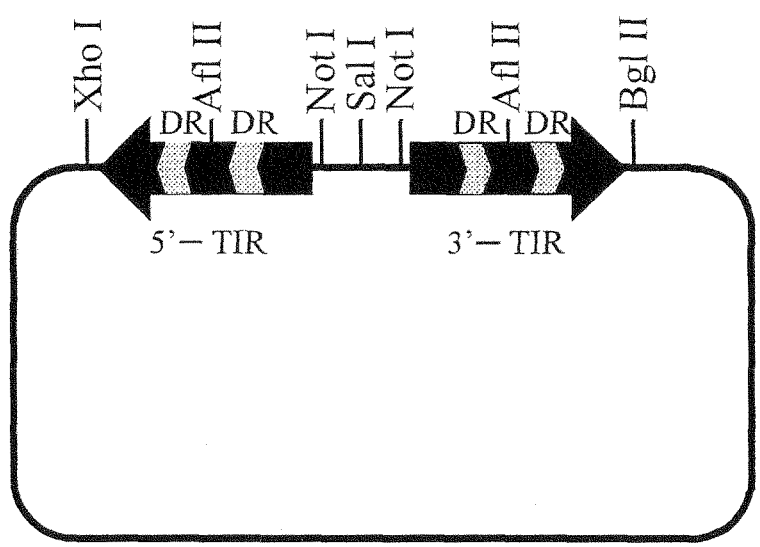
FIG. 5 shows a structure of IR/DR-NTA-Ad/pSP which is IR/DR-N with addition of a restriction enzyme recognition site.

IR/DR-N-Ad is further treated as described below for adding restriction enzymes recognition sites necessary for construction at both ends of the TIR sequences. IR/DR-N-Ad is digested with AflII to recover a DNA fragment of about 2.5 kbp containing the sequence from pSP72 vector and a DNA fragment of about 630 bp. The DNA fragment of about 2.5 kbp is made circular using DNA Ligation Kit (TaKaRa). Using this as a template, PCR is performed with primers 5'IR/DRTA-Fs (SEQ ID NO: 25) and 3'IR/DRTA-R (SEQ ID NO: 26) to amplify a DNA fragment of about 150 bp wherein restriction enzymes recognition sites are added at the 5' and 3' ends. This DNA fragment is once cloned into a plasmid (TA-Fs/R) and the plasmid is then digested with restriction enzymes XhoI and BglII and inserted into a cloning vector pSP72, which has previously been digested with the same restriction enzymes and then BAP treated, to provide TA-Fs/R-pSP. Said TA-Fs/R-pSP is digested with restriction enzyme AflII and BAP treated, into which the above DNA fragment of about 630 bp is inserted to provide a transposon vector IR/DR-NTA-Ad/pSP which bears restriction enzymes (StuI, NotI, SalI and MscI) recognition sites between the 5'- and 3'-TIR sequences as well as restriction enzymes (XhoI and BglII) recognition sites outside both the TIR sequences (FIG. 5).

Whether a fragment of interest could be obtained may suitably be confirmed by sequencing. For insertion of other restriction enzymes recognition sites than those described above, an adaptor with the corresponding restriction enzymes recognition sites may be used. When preparing an adaptor, a synthetic DNA may be used whose nucleotide sequence is prepared so as to contain a restriction enzyme recognition site of interest. Such a suitable restriction enzyme recognition site would allow for insertion of a variety of gene expression cassettes or a sequence where a recombination reaction occurs and be applied for destruction of TIR sequences as described hereinbelow.

(3) Expression Cassette of Gene

An expression cassette of a gene is imposed with no special condition and is defined as a nucleic acid fragment of a foreign gene to which a suitable expression control region such as a promoter, termination codon, poly(A) addition signal, Kozak sequence, secretion signal, etc. are added. A promoter to be contained in said expression cassette may be any promoter capable of expression of a foreign gene such as SV40 early, SV40 late, cytomegalovirus and chicken β actin promoters as selected from combination with animal cells used as a host. Preferably, an expression plasmid pCAGG with chicken β actin promoter (Japanese patent publication No. 168087/1991) may be used. For a marker gene for selection or gene amplification, a marker gene commonly known to be used for selection or gene amplification such as neo, dihydrofolate reductase (dhfr), puromycin resistant enzyme and glutamate synthetase (GS) genes may be used. A commercially available marker gene may also be used and includes pSI, pCI-neo (Promega) for expression in animal cells; pPICZ (Invitrogen), pESP-1 (Stratagene) for yeast; BacPAK6 (Clontec), pBAC (Novagen) for insect cells; and pET (Stratagene) for bacteria, which may suitably be used for the specific purpose. Examples of insertion of an expression cassette of a gene are insertion of a drug selection marker such as puromycin resistant enzyme gene, insertion of an expression cassette of a marker gene such as GFP, or insertion of an expression cassette of a foreign gene of interest, as described in Examples of the present invention.

2. Modified Transposon Vector with Insertion of a Sequence where Recombination Reaction Occur (1) Construction of Modified Transposon Vector A modified transposon vector may be constructed by inserting a sequence where a recombination reaction occurs such as Lox sequence between the two DR regions each present within 5'- and 3'-TIR sequences of a transposon gene. As a consequence of insertion at this site, the transposition activity (the activity to transpose on cellular chromosome) of a native transposon may be lost by using subsequently a recombination system such as Cre-Lox while maintaining its high introduction efficiency into cells. This effect may be attained by inserting a sequence where a recombination reaction occurs such as Lox sequence into at least either of 5'- or 3'-TIR sequence of a transposon vector.

Araki, K. et al. (*Nucleic Acids Res.*, 30(19), e103, 2002) and Soukharev, S. et al. (*Nucleic Acids Res.*, 27(18), e21, 1999) revealed that replacement and insertion reactions occur more efficiently than deprivation reaction by exploiting a mutated Lox sequence. A variety of mutated Lox sequences have been studied (G. Lee and I. Saito, *Gene*, 55-65, 216, 1998) and there is possibility of varied sequences. A suitable sequence includes Lox71 sequence (SEQ ID NO: 4), Lox66 sequence (SEQ ID NO: 5), Lox2272 sequence (SEQ ID NO: 6), Lox511 sequence (SEQ ID NO: 7), etc. as already reported. When merely the loss of the transposition activity of a transposon is aimed, any sequence may be used where a recombination reaction occurs including LoxP sequence. Since various mutated sequences are known as described above, Cre-Lox recombination system may preferably be used for the purpose of efficient replacement or insertion of a foreign gene.

Besides, when Cre-Lox recombination system is used, a combination needs be considered of a mutated Lox sequence to be inserted into a transposon vector and a mutated Lox sequence to be used for replacement or insertion reaction. If a replacement reaction is expected, it is preferable that a combination of Lox71 sequence with Lox2272, Lox511 or LoxP sequence is inserted into a transposon vector whereas a combination of Lox66 sequence with Lox2272 sequence, Lox511 sequence or LoxP sequence is inserted into a plasmid (donor plasmid) which provides gene insertion by subsequent replacement reaction with Cre-Lox recombination system. Among these, a combination of Lox71 and Lox2272 sequences for a transposon vector and a combination of Lox66 and Lox2272 sequences for a donor plasmid are the most efficient. Conversely, the combination is likewise efficient such that Lox71 sequence is inserted into a donor plasmid and Lox66 sequence into a transposon vector. If a replacement reaction is expected, a combination of Lox71-Lox66 is the best wherein Lox71 sequence may be inserted into a transposon vector whereas Lox66 sequence is inserted into a donor plasmid or vice versa.

Although a best mode of the present invention will be explained hereinbelow with Cre-Lox recombination system since this system is the best for efficient replacement and insertion of a gene due to mutated Lox sequences as described above, other recombination systems such as Flp-FRT may also be used.

A modified transposon vector with insertion of a Lox sequence may be constructed by performing PCR with primers in which a Lox sequence is inserted using as a template a nucleic acid fragment bearing 5'- or 3'-TIR sequence of a transposon gene. More specifically, PCR is performed, for instance, with SP6 primer (SEQ ID NO: 27) and a primer Ps/Lx71R (SEQ ID NO: 28) bearing Lox71 sequence using IR/DR-NTA-Ad/pSP as a template to provide a DNA fragment of about 200 bp. This DNA fragment is once cloned using TOPO TA Cloning kit (INVITROGEN), digested with restriction enzymes PshAI and XhoI and inserted into IR/DR-NTA-Ad/pSP, which has previously been digested with the same restriction enzymes and then BAP treated, to construct a modified transposon vector IR/DR-Ad/5'Lxp wherein Lox71 sequence is inserted between the two DR sequences present within 5'-TIR sequence.

A modified transposon vector 3'IR/DR-Lxp/pP wherein LoxP sequence is inserted between the two DR sequences present within 3'-TIR sequence may be obtained by digestion of IR/DR-NTA-Ad/pSP with restriction enzymes SalI and BglII and cloning into pSP72 (Promega), which has previously been digested with the same restriction enzymes and then BAP treated, to construct 3'IR/DR-Ad/pSP. Using this as a template, PCR is performed with SP6 primer (SEQ ID NO: 27) and a primer Af/LxpR (SEQ ID NO: 29) in which LoxP sequence is inserted to provide a DNA fragment of about 400 bp wherein LoxP sequence is added within 3'-TIR sequence. This DNA fragment is once cloned using TOPO TA Cloning kit (INVITROGEN), digested with restriction enzymes AflII and SalI and inserted into 3'IR/DR-Ad/pSP, which has previously been digested with the same restriction enzymes and then BAP treated, to construct a modified transposon vector 3'IR/DR-Lxp/pSP.

In case of insertion of Lox sequences into both 5'- and 3'-TIR sequences of a transposon, a desired construct may be obtained by replacing the 3'-TIR sequence of IR/DR-Ad/5'Lxp with 3'IR/DR-Ad/pSP. For instance, 3'IR/DR-Lxp/pSP is digested with restriction enzymes BglII and SalI and the resulting fragment is inserted into IR/DR-Ad/5'Lxp, which has previously been digested with the same restriction enzymes and then BAP treated, to construct a modified transposon vector IR/DR-Ad/LxDb bearing a, mutated Lox sequence (Lox71) within 5'-TIR sequence and LoxP sequence within 3'-TIR sequence.

For stable expression of a foreign gene in animal cells, a poly(A) addition signal sequence downstream a translation region is necessary. In the absence of a poly(A) addition signal sequence, mRNAs transcribed from a gene become unstable to ultimately result in reduction of expression of a final product, protein. Utilizing this principle, a poly(A) trap method has been developed wherein a homologous recombination is designed so that a drug selection marker with no poly(A) addition signal sequence downstream thereof may be introduced into cells but a poly(A) addition signal sequence may be present downstream the drug selection marker only in case of insertion at the desired site to thereby allow for efficient selection of cells where homologous recombination occurred. It is thus possible to construct a modified transposon vector with higher efficiency of replacement by exploiting this method in addition to the mutated Lox sequence as described above. For this purpose, a poly(A) addition signal sequence may be added downstream the Lox sequence inserted into 3'-TIR sequence.

Such a modified transposon vector may be obtained, for instance, by performing PCR with SP6 primer and primer Af/LxpAR (SEQ ID NO: 30) in which a poly(A) addition signal sequence derived from bovine growth hormone is added downstream LoxP sequence using 3'IR/DR-Lxp/pSP as a template to amplify and recover a DNA fragment of about 400 by wherein LoxP sequence together with the poly(A) addition signal sequence downstream thereof are added within 3'-TIR sequence. This DNA fragment is once cloned using TOPO TA Cloning kit (INVITROGEN), digested with restriction enzymes AflII and SalI and inserted into 3'IR/DR-Lxp/pSP, which has previously been digested with the same restriction enzymes and then BAP treated, to construct 3'IR/DR-LxpA/pSP. 3'IR/DR-LxpA/pSP is further digested with restriction enzymes BglII and SalI and inserted into IR/DR-Ad/5'Lxp, which has previously been digested with the same restriction enzymes and then BAP treated, to construct a modified transposon vector IR/DR-Ad/LxpADb bearing a mutated Lox sequence (Lox71) within 5'-TIR sequence and LoxP sequence together with the poly(A) addition signal sequence downstream thereof within 3'-TIR sequence.

Modified transposon vectors of the present invention, IR/DR-Ad/5'Lxp, IR/DR-Ad/LxDb and IR/DR-Ad/LxpADb, as possessing recognition sites for several restriction enzymes, may be used for construction of an expression plasmid of a foreign gene by inserting a suitable expression cassette of a foreign gene into these restriction enzymes recognition sites. Such an expression plasmid of a foreign gene may appropriately be introduced into cells including ontogenetic cells to prepare cells and an animal producing a foreign protein. An expression cassette of a foreign gene is defined as a nucleic acid fragment of a foreign gene to which a suitable promoter, termination codon, poly(A) addition signal, Kozak sequence, secretion signal, etc. are added. Introduction of an expression cassette of a foreign gene into suitable cells allows for expression of a foreign gene in said cells. Such a nucleic acid fragment may easily be prepared by inserting a foreign gene into any of various expression vectors (or expression plasmids) already commercially available as instructed by protocol attached thereto and then cleaving out said nucleic acid fragment with a suitable restriction enzyme. A commercially available product includes, for instance, pSI, pCI-neo (Promega) for expression in animal cells; pPICZ (Invitrogen), pESP-1 (Stratagene) for yeast; BacPAK6 (Clontec), pBAC (Novagen) for insect cells; and pET (Stratagene) for bacteria, which may suitably be used for the specific purpose.

(2) Construction of Donor Plasmid (pLx/GFP/neo/pA(−))

A donor plasmid for use in gene replacement exploiting Cre-Lox recombination system may be constructed as described below. An expression cassette of a foreign gene is added with Lox sequences at its both ends. The Lox sequence may be any Lox sequence inserted into 5'- and 3'-TIR sequences of a transposon vector but, for obtaining higher replacement efficiency in Cre-Lox recombination system, is preferably a combination of either Lox71-Lox66 sequences or Lox2272-Lox2272 sequences.

Figure 6:
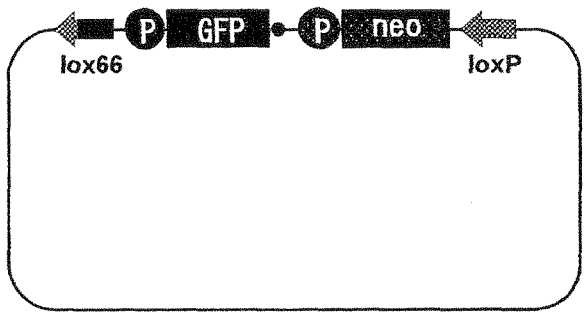
FIG. 6 shows a donor plasmid pLx/GFP/neo/pA(−) which, after introduction of a modified transposon vector into cells, is introduced for inducing a gene replacement reaction.

Specifically, a primer Lx66/LxP-F (SEQ ID NO: 31) bearing XhoI recognition site at its 5' end and Lox66 sequence in its interior and a primer Lx66/LxP-R (SEQ ID NO: 32) bearing BglII recognition site at its 5' end and LoxP sequence in its interior are initially mixed together and PCR is performed without addition of a template DNA, 25 nucleotide residues at 3' end of Lx66/LxP-F and 25 nucleotide residues at 3' end of Lx66/LxP-R being homologous to each other, to provide a fragment of about 120 bp consisting of Lox66 and LoxP sequences. Into this fragment is then inserted an expression cassette wherein GFP gene is inserted downstream a promoter obtained from an expression vector for animal cells pCAGn-mcs-polyA (Japanese patent application No. 165249/1996). An expression cassette of neo gene as a marker gene without poly(A) addition signal is further inserted downstream the GFP gene. Thus, d donor plasmid pLx/GFP/neo/pA(−) (FIG. 6) is constructed wherein Lox66 and LoxP sequences are added to 5' and 3' ends, respectively, of an expression cassette of GFP gene and neo gene.

(3) Construction of Expression Plasmid of Cre Gene (pCAGGS/Cre)

A Cre gene for use in Cre-Lox recombination system needs be functionally expressed in the same target cells wherein the donor plasmid as described above is introduced. For this purpose, a Cre gene may be incorporated into a suitable expression vector which is then introduced into cells wherein a Cre gene may be included in either the same plasmid as the donor plasmid or separately in other plasmid than the donor plasmid. Furthermore, synthesis and introduction of a Cre gene RNA or even direct introduction of the expressed protein would meet with the condition of the present invention insofar as the Cre activity is exerted within cells. An example of such a plasmid that allows for expression of a desirable Cre gene in animal cells (hereinafter also referred to as "Cre expression plasmid") includes a plasmid pCAGGS/Cre generously presented by Assistant Professor Araki of Kumamoto University, Gene Technology Center. Said plasmid pCAGGS/Cre may be obtained as described in *Proc. Natl. Acad. Sci. USA*, 92, 160-164, 1995. Briefly, it is obtained by inserting a gene encoding Cre into the restriction enzyme SalI recognition site of an expression vector pCAGGS.

3. Transposase

A transposase for use with a transposon vector may be any insofar as it endows a transposon vector with a transposon activity but preferably is one paired with a transposon vector. A transposase needs be functionally expressed in the same target cells wherein a transposon vector is introduced. For this purpose, a transposase gene may be incorporated into a suitable expression vector which is then introduced into cells wherein a transposase gene may be included in either the same plasmid as a transposon vector or separately in other plasmid than a transposon vector. Furthermore, synthesis and introduction of a transposase gene RNA or even direct introduction of the expressed protein would meet with the condition of the present invention insofar as the transposase activity is exerted within cells.

(1) Isolation of Transposase Gene

Since a gene encoding a transposase is inactivated and is not expressed in salmon, it may be prepared by using as a starting material a genomic DNA extracted from tissues by a general genetic engineering technique as taught by Sambrook et al. (Molecular Cloning, A Laboratory Manual Second Edition, Cold Spring Harbor Laboratory Press, N.Y., 1989). In practice, a commercially available kit may be used for extraction of DNAs, including Wizard Purification System (Promega), ISOTISSUE (NIPPON GENE CO., LTD.), DNA Extraction Kit (Toyobo), Genomic-tip System (QIAGEN), and the like.

More specifically, using DNAs from salmon sperm (NIPPON GENE CO., LTD.) as a template, PCR is performed with LA-Taq (TaKaRa) and reagents attached thereto to amplify a transposase gene. Synthetic DNAs are used as primers of PCR. For instance, a 5' primer (SEQ ID NO: 33) based on the nucleotide sequence of a salmon transposase gene (EMBL/GenBank accession No. L12206) and a 3' primer (SEQ ID NO: 34) based on the nucleotide sequence of a rainbow trout transposase gene (EMBL/GenBank accession No. L12209) may be used to amplify a transposase gene of about 1 kbp. PCR is performed wherein the reaction solution is subject to a Thermal Cycler PC-800 (ASTEC Co., Ltd.) under normal PCR conditions (40 cycles of denaturation at 96° C. for 20 sec., annealing and elongation at 68° C. for 1.5 min.).

The amplified DNA fragments are once cloned into a plasmid (pCR2.1) using TOPO TA Cloning kit (INVITROGEN). A full nucleotide sequence of the DNA fragments may be determined using BigDye Terminator Cycle Sequencing FS Ready Reaction Kit and ABI PRISM 310 Genetic Analyzer from Applied Biosystems (ABI). Since a transposase from salmon is present in an inactivated form lacking the transposition activity as a consequence of accumulated amino acid mutations, the amino acid sequence deduced from the obtained DNA fragments is compared with that of a transposase having the transposition activity (Sleeping Beauty Transposase; hereinafter referred to as "SB transposase") as reported by Ivies et al. (*Cell*, 91, 501-, 1997). Those amino acid residues which are different from those of SB transposase are repaired so as to be conformity therewith. For comparison of homology in amino acid sequences, genetic data processing software GENETYX (GENETYX CORPORATION) may be used. For repair of nucleotide sequence, site-directed mutagenesis may commonly be used. In practice, it may be done using a commercially available kit where this technique is applied such as Site-Directed Mutagenesis System (such as Mutan-Super Express Km, Mutan-Express Km, Mutan-K) from Takara, QuickChange Multi Site-Directed Mutagenesis Kit, QuickChange XL Site-Directed Mutagenesis Kit from Stratagene, or GeneTailor Site-Directed Mutagenesis System from Invitrogen, in accordance with protocol attached thereto. In accordance with the present invention, the nucleotide sequence was repaired by mutagenesis using PCR (as reported by Ivics et al., *Cell*, 91, 501-, 1997) to provide a plasmid (SB/pSP) wherein a nucleic acid fragment having the nucleotide sequence encoding the same amino acid sequence as that of SB transposase gene is inserted.

(2) Construction of Transposase Expression Plasmid pCAGG/SB

The thus obtained SB transposase gene may be incorporated into a suitable expression vector which is then introduced into a host to thereby allow for expression of SB transposase in said host. As a host for expression of SB transposase, bacteria, yeast, animal cells, plant cells and insect cells may be used as is common in expression of a foreign gene, selection of which may appropriately be done depending on each purpose of research and development. Preferably, animal cells are used as a host wherein Kozak sequence may sometimes be added at the 5' side of SB transposase for increasing expression efficiency. An expression vector may suitably be selected and used from those developed and commercially available for expression in animal cells. More specifically, using a plasmid (SB/pSP) wherein an SB transposase gene fragment is cloned as a template, the synthetic DNAs of SEQ ID NOs: 35 and 36 are used to amplify an SB transposase gene. These primers are such that restriction enzyme XhoI recognition site and Kozak sequence are added to SEQ ID NO: 33 corresponding to 5'-end of an SB transposase gene and restriction enzymes SalI and BglII recognition sites are added to SEQ ID NO: 34 corresponding to 3'-end of an SB transposase gene. The obtained cDNA fragment is digested with restriction enzymes XhoI and BglII and cloned into a cloning vector pSP72 (Promega), which has previously been digested with the same restriction enzymes and then dephosphorylated (BAP), to provide a plasmid SB/XS. Then, pCAGGS-DN5, which is a partial modification of an expression vector pCAGn-mcs-polyA for expression in animal cells (Japanese patent application No. 165249/1996), is digested with restriction enzyme SalI and BAP treated, to which a DNA fragment containing a transposase gene obtained from digestion of SB/XS with restriction enzymes XhoI and SalI is then inserted to construct an expression plasmid of transposase (pCAGG/SB).

4. Introduction of Transposon Vector into Cells (1) Introduction of Various Transposon Vectors into Animal Cells Introduction of a transposon vector into animal cells may be carried out as described below. Animal cells include a cell line (such as HeLa, Vero, CHO, 293, BHK, and myeloma cell such as SP2/0), a primary cell (such as CE, HUVEC), and an ontogenetic cell (an ES cell, an EG cell, a cell from a fertilized egg up to the blastocyst stage, and a primordial germ cell (PGC)), which may suitably be selected depending on the purpose. A gene may be introduced into animal cells by any method without limitation such as e.g. calcium phosphate method, DEAE-dextran method, a method using liposome such as with lipofectin, polyethylene glycol fusion for protoplasts, or electroporation, which may suitably be selected depending on host cells to be used (Molecular Cloning (3rd Ed.), Vol. 3, Cold Spring Harbor Laboratory Press (2001)). A culture medium for use in culture may be agar or liquid medium from viewpoint of its form or DMEM, RPMI or αMEM from viewpoint of its sorts and may appropriately be selected depending on a kind of cells, purpose of culture, or a stage of culture. In accordance with each protocol of respective culture media, serum, an amino acid, a vitamin, a sugar, an antibiotic, a pH adjuster and the like may be added. A culture medium is set to conditions of pH 6-8 and culture temperature of 30-39° C. An amount of a culture medium, an additive and time for culture may suitably be adjusted depending on a culture scale.

For instance, to Opti-MEM I Reduced-Serum Medium (INVITROGEN) is added Trans-IT LT1 (TaKaRa) and the mixture is stirred and kept to stand at room temperature for 10 min. To the mixture are further added a transposase expression plasmid pCAGGS/SB and a transposon vector bearing an expression cassette of a gene and the mixture is stirred and kept to stand at room temperature for 15 min. This is added to HeLa cells prepared the previous day which are cultured at 37° C. for hours. A culture supernatant is removed and 2 ml/well of DMEM medium (hereinafter also referred to as "10% complete DMEM") containing 10% fetal bovine serum and 1/100 amount of penicillin-streptomycin is added and culture continued at 37° C. for 2 days in the presence of 5% $CO_2$. Culture further continued in a culture medium containing a drug as appropriate for a selection marker gene used to obtain drug resistant cells. The obtained cells may be cloned by a limiting dilution method as in usual transformed cells.

(2) Introduction of Donor Plasmid and Expression Plasmid of Cre Gene into Cells Transformed with Modified Transposon Vector Introduction of a donor plasmid wherein a foreign gene is inserted therein and an expression plasmid of a Cre gene into the cells transformed with the modified transposon vector as described above allows for replacement of an expression cassette of a foreign gene of the donor plasmid at Lox sequences. The introduction may be done as described hereinabove. When a selection marker gene is used, it needs be a different one from that of the modified transposon vector. In case of an exchange reaction, it is possible to select cells wherein a foreign gene is inserted by the absence of drug resistance without using a selection marker gene. For cells transformed with a modified transposon vector in a GFP gene is inserted therein, expression of the GFP gene may easily be detected by observing fluorescence generated by ultraviolet irradiation of excitation wave length. Thus, its replacement with a foreign gene by Cre-Lox recombination system may be selected by the loss of said fluorescence. For instance, a cell sorter may also be used to enable easy and speedy selection of those cells that undertook replacement and those not.

Replacement of an expression cassette of a foreign gene by Cre-Lox recombination system will remove a sequence containing the single inner DR sequences within each of 5'- and 3'-TIR sequences of a modified transposon vector inserted in chromosomal DNAs to thereby drastically reduce introduction efficiency of the modified transposon vector into chromosomal DNAs of cells. This phenomenon may also be seen when only either one of the inner sequences of 5'- or 3'-TIR sequence is removed. Thus, if the introduction activity of a transposon should be maintained, Lox sequences must be inserted at specific sites so as not to lose TIR sequences, specifically between the DR regions present by twos within TIR sequences. Conversely, by removing the inner DR sequences within each of 5'- and 3'-TIR sequences, it is expected that the transposition competence characteristic to a transposon may surely be suppressed after its insertion into chromosomal DNAs.

Alternatively, in addition to replacement and insertion of a gene exploiting Cre-Lox system, TIR sequences may also be destroyed by a deprivation reaction as described below. For instance, a transposon vector may be introduced into cells wherein a sequence where a recombination reaction occurs such as LoxP sequence is inserted at the interior restriction enzyme recognition site whereas another sequence where a recombination reaction occurs is inserted between the DR sequences of either 5'- or 3'-TIR sequence. To the resulting transformed cells, any of an expression plasmid of an enzyme undertaking a recombination reaction corresponding to the inserted sequence where a recombination reaction occurs (Cre in case of LoxP sequence), a mRNA for said enzyme or said enzyme per se may be introduced to thereby induce a deprivation reaction of a region flanked by the sequences where a recombination reaction occurs, resulting in removal of one of the DR sequences present by two of either 5'- or 3'-TIR sequence, to destroy the transposon competence.

The present invention is explained in more detail by means of the following Examples but should not be construed to be limited thereto. In the following Examples, reagents from Wako Pure Chemical Industries, Ltd. or Nacalai torque were used unless otherwise instructed.

Example 1

Isolation of Active Transposase

Using DNAs from salmon sperm (NIPPON GENE CO., LTD.) as a template, PCR was performed to amplify a DNA fragment of about 1 kbp comprising a transposase gene. Specifically, with LA-Taq (TaKaRa) and reagents attached thereto, 25 µl of a reaction solution was prepared comprising 0.5 µg of salmon DNAs, each 400 µM of dATP, dCTP, dGTP and dTTP, magnesium chloride (2.5 mM), each 800 nM of a 5' primer (SEQ ID NO: 33) based on the nucleotide sequence of a salmon transposase gene (EMBL/GenBank accession No. L12206) and a 3° primer (SEQ ID NO: 34) based on the nucleotide sequence of a rainbow trout transposase gene (EMBL/GenBank accession No. L12209), and LA-Taq (50 unit/ml). The reaction solution was subject to a Thermal Cycler PC-800 (ASTEC Co., Ltd.) to perform 40 cycles of denaturation at 96° C. for 20 sec., annealing and elongation at 68° C. for 1.5 min.

The amplified DNA fragments were cloned into a plasmid (pCR2.1) using TOPO TA Cloning kit (INVITROGEN). A full nucleotide sequence of the DNA fragments as cloned was determined using BigDye Terminator Cycle Sequencing FS Ready Reaction Kit and ABI PRISM 310 Genetic Analyzer from Applied Biosystems (ABI).

The amino acid sequence deduced from the obtained DNA fragments was compared with that of SB transposase as reported by Ivics et al. (*Cell*, 91, 501-, 1997) for homology using genetic data processing software GENETYX (GENETYX CORPORATION). As a result, as expected, numerous mutations were observed. Each of the mutations were repaired so as to be conformity with the amino acid sequence of SB transposase by site-directed mutagenesis using PCR (as reported by Ivics et al., *Cell*, 91, 501-, 1997). Namely, various primers for repairing the mutations were synthesized and DNA fragments amplified with these primers were replaced for those regions where the mutations were present to obtain a plasmid (SB/pSP) wherein SB transposase gene fragment as repaired was inserted. The nucleotide and amino acid sequences of said SB transposase gene are shown in FIGS. 7 and 8, respectively.

Example 2

Construction of Transposase Expression Plasmid pCAGG/SB

Kozak sequence was added at the 5' side of a gene encoding SB transposase by PCR and the resulting gene was inserted into an expression vector for animal cells. First, using SB/pSP obtained in Example 1 as a template, PCR was performed with 5' primer (SEQ ID NO: 35) and 3' primer (SEQ ID NO: 36) to amplify a DNA fragment wherein restriction enzyme XhoI recognition site and Kozak sequence were added to 5'-end and restriction enzymes SalI and BglII recognition sites were added to 3'-end of the transposase gene. PCR was done as described in Example 1. The obtained DNA fragment was digested with restriction enzymes XhoI and BglII and cloned into a cloning vector pSP72 (Promega), which has previously been digested with the same restriction enzymes and then dephosphorylated (BAP) (the obtained cloning vector is hereinafter referred to as "SB/XS"), Then, a plasmid pCAGGS-DN5, which is a partial modification of an expression vector pCAGn-mcs-polyA for expression in animal cells (Japanese patent application No. 165249/1996), is digested with restriction enzyme SalI and BAP treated, to which a DNA fragment containing a transposase gene obtained from digestion of SB/XS with restriction enzymes XhoI and SalI is then inserted to construct an expression plasmid of a transposase (pCAGG/SB).

Example 3

Construction of Transposon Vector (IR/DR-NTA-Ad/pSP)

A transposon vector IR/DR-NTA-Ad/pSP was constructed which bears several restriction enzymes recognition sites between the 5'- and 3'-TIR sequences of a transposon gene as described below.

(1) Isolation of 5'- and 3'-TIR Sequences

Using DNAs from salmon sperm (NIPPON GENE CO., LTD.) as a template, PCR was performed with a primer (SEQ ID NO: 8) as reported by A. D. Radice et al. (*Mol. Gen. Genet.* 244, 606-, 1994) to amplify a DNA fragment of about 1.6 kbp comprising a transposase gene and both 5'- and 3'-TIR sequences. The amplified DNA fragment was cloned into a plasmid pCR2.1 as described in Example 1. A full-length nucleotide sequence of the 1.6 kbp DNA fragment in the plasmid retained in said clone (hereinafter referred to as "Salmon Tc1") was determined and the sequence was repaired so as to be in conformity with the TIR sequence (EMBL/GenBank accession No. L48685) from *Tanichthys albonubes* (white cloud mountain minnow in Japanese) as reported by Ivics et al. (*Cell*, 91, 501-, 1997) in accordance with the scheme shown in FIG. 9.

First, the isolated Salmon Tc1 was digested with restriction enzymes EcoRI and AccI. The resulting DNA fragments of about 0.4 kbp and about 1.2 kbp were separated from the DNA fragment from the plasmid on 1.5% agarose gel. These two DNA fragments were recovered using GFX PCR DNA and Gel Band Purification Kit (Amersham Bioscience) and subcloned into a cloning vector pSP72 (Promega) (the obtained vectors are hereinafter referred to as "5'Rg/pSP" and "3'Rg/pSP", respectively).

The 5'-TIR sequence was repaired as described below. Using 5'Rg/pSP as a template, PCR was performed with primers for repair IR/DR rF1 (SEQ ID NO: 9) and IR/DR rR1 (SEQ ID NO: 10) to amplify a DNA fragment of about 0.3 kbp which was recovered. The DNA fragment was cloned into a plasmid (pCR2.1) using TOPO TA Cloning kit (INVITROGEN). The plasmid was then digested with restriction enzymes EcoRI and HindIII and the resulting fragment was separated on agarose gel. The fragment was inserted into 5'Rg/pSP, which has previously been digested with the same restriction enzymes and then BAP treated, to construct 5'RgDR/pSP. Using the 5'RgDR/pSP as a template, PCR was performed with combinations of primers for repair, IR/DR-5'/F1 (SEQ ID NO: 11) and IR/DR-5'/R1 (SEQ ID NO: 12), and IR/DR-5'/F2 (SEQ ID NO: 13) and IR/DR-5'/R2 (SEQ ID NO: 14), to amplify DNA fragments of about 100 bp and about 160 bp which were recovered. An equivalent amount of these DNA fragments were mixed together and, after denaturation (at 70° C. for 10 min.), the mixture was gradually cooled to room temperature for annealing. Using the homologous DNA sequences annealed between both the DNA fragments as a template, PCR was again performed with the primers as described above, IR/DR-5'/R1 and IR/DR-5'/R2, to amplify a DNA fragment of about 240 bp which was cloned with TOPO TA Cloning kit (INVITROGEN). The plasmid was digested with restriction enzymes AflII and HindIII and the resulting fragment was inserted into 5'RgDR/pSP, which has previously been digested with the same restriction enzymes and then BAP treated, to construct a plasmid 5'IR/DR-N having the 5'-TIP sequence.

On the other hand, the 3'-TIR sequence was repaired as described below. Using 3'Rg/pSP as a template, PCR was performed with combinations of primers for repair, IR/DR rF2 (SEQ ID NO: 15) and IR/DR rR2 (SEQ ID NO: 16), and IR/DR rF3 (SEQ ID NO: 17) and IR/DR rR3 (SEQ ID NO: 18), to amplify each of DNA fragments of about 200 bp which were recovered. An equivalent amount of these DNA fragments were mixed together and the mixture was treated for annealing as described above. Using this DNA as a template, PCR was again performed with the primers as described above, IR/DR rF2 and IR/DR rR3, to amplify a DNA fragment of about 370 bp which was cloned with TOPO TA Cloning kit (INVITROGEN). The plasmid was digested with restriction enzymes EcoRI and MscI and the resulting fragment was inserted into 3'Rg/pSP, which has previously been digested with the same restriction enzymes and then BAP treated, to construct a plasmid 3'RgDR/pSP having the 3'-TIR sequence. Nucleotide sequences of the two DR regions of the thus obtained 5'- and 3'-TIR sequences as repaired were determined as described in Example 1. As a result, the nucleotide sequences of the DR regions of the 5'- and 3'-TIR sequences as repaired were those of SEQ ID NO: 19 and SEQ ID NO: 20, respectively.

(2) Construction of a Transposon Vector (IR/DR-NTA-Ad/pSP)

Figure 10:
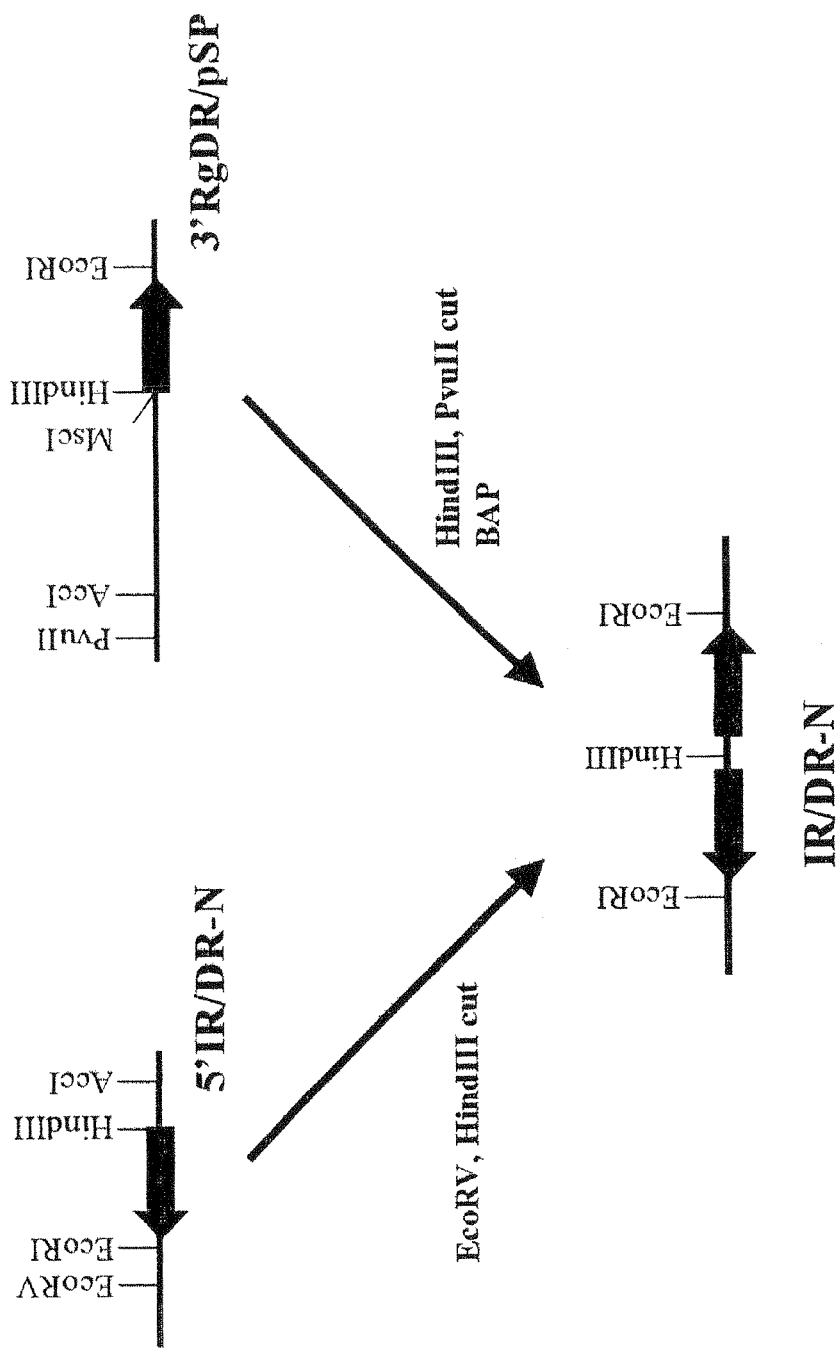
FIG. 10 is a schematic illustration showing construction of a transposon vector IR/DR-N.

First, a DNA fragment comprising the 5'-TIR sequence obtained by digesting 5'IR/DR-N with restriction enzymes HindIII and EcoRV was inserted into 3'RgDR/pSP comprising the 3'-TIR sequence, which has previously been digested with restriction enzymes HindIII and PvuII and then BAP treated, to construct IR/DR-N comprising both the 5'- and 3'-TIR sequences (FIG. 10).

Next, an adaptor having several restriction enzymes recognition sites was inserted into HindIII cleavage site of IR/DR-N. An equivalent amount of primers, 5'IR/DR-AdF (SEQ ID NO: 21) and 5'IR/DR-AdR (SEQ ID NO: 22), phosphorylated at the 5' end, were mixed together and annealed as described in Example 3(1) to provide an adaptor 5'IR/DR-Ad where both primers were annealed. In like manner, an adaptor 3'IR/DR-Ad was obtained where 3'IR/DR-AdF (SEQ ID NO: 23) and 3'IR/DR-AdR (SEQ ID NO: 24) were annealed. An equivalent amount of 5'IR/DR-Ad and 3'IR/DR-Ad were mixed together, reacted at 16° C. for 30 min. using DNA Ligation Kit (TaKaRa) and precipitated with ethanol to recover a DNA fragment wherein both adaptors were bound (IR/DR-Ad). This DNA fragment was digested with restriction enzyme HindIII and inserted into HindIII site of IR/DR-N previously constructed to construct IR/DR-N-Ad.

Figure 11:
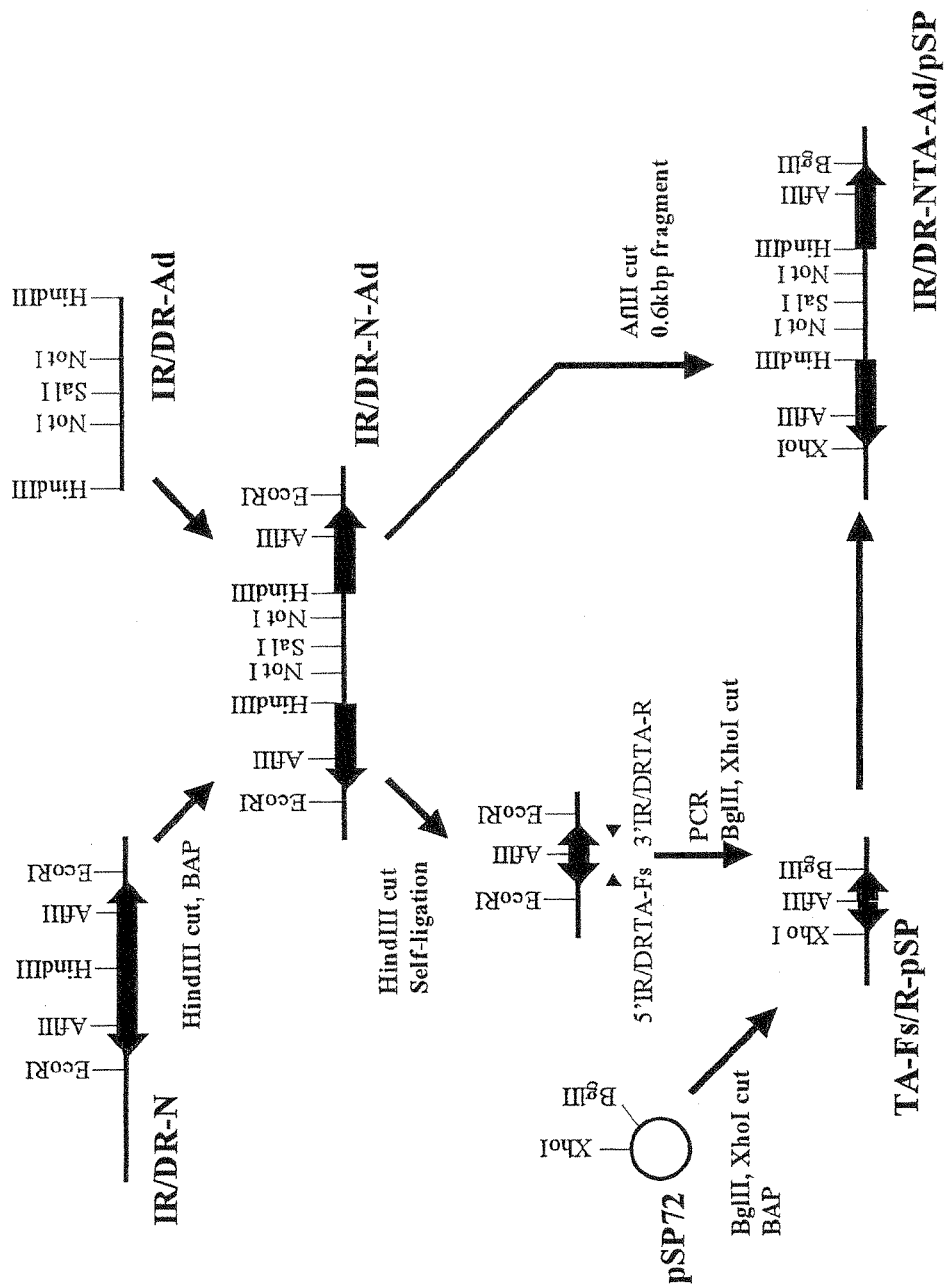
FIG. 11 is a schematic illustration showing construction of IR/DR-NTA-Ad/pSP which is a transposon vector IR/DR-N with addition of a restriction enzyme recognition site.

Restriction enzymes recognition sites were added at both ends of the 5'- and 3'-TIR sequences as described below. The obtained IR/DR-N-Ad was digested with AflII to recover a DNA fragment of about 2.5 kbp containing the sequence from pSP72 vector and a DNA fragment of about 630 bp. The DNA fragment of about 2.5 kbp was made circular using DNA Ligation Kit (TaKaRa). Using this as a template, PCR was then performed with primers 5'IR/DRTA-Fs (SEQ ID NO: 25) and 3'IR/DRTA-R (SEQ ID NO: 26) to amplify a DNA fragment of about 150 bp wherein restriction enzymes recognition sites were added at the 5' and 3' ends. This DNA fragment was cloned with TOPO TA Cloning kit (INVITROGEN) (the obtained plasmid is hereinafter referred to as "TA-Fs/R") and the nucleotide sequence of the DNA fragment of 150 bp was determined. TA-Fs/R was digested with restriction enzymes XhoI and BglII and inserted into a cloning vector pSP72, which has previously been digested with the same restriction enzymes and then BAP treated, to construct TA-Fs/R-pSP. Said TA-Fs/R-pSP was digested with restriction enzyme AflII and BAP treated, into which the above DNA fragment of 630 bp was inserted. Thus, a transposon vector IR/DR-NTA-Ad/pSP was obtained which bears restriction enzymes (StuI, NotI, SalI and MscI) recognition sites between the 5'- and 3'-TIR sequences necessary for transposition as well as restriction enzymes (XhoI and BglII) recognition sites outside both the TIR sequences (FIG. 11).

Example 4

Construction of Plasmid for Assessing Transposon Activity (IR/DR-puro)

Figure 12:
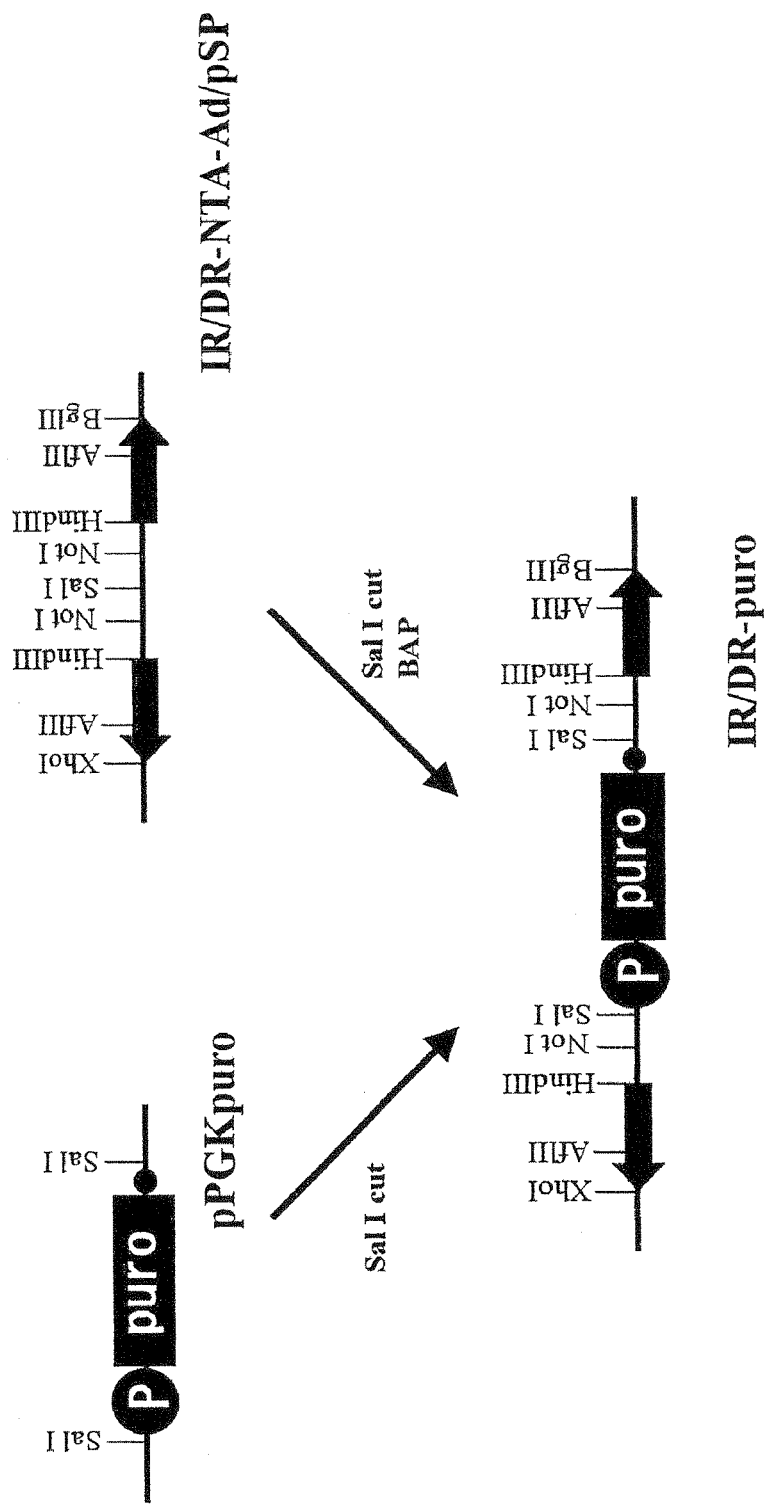
FIG. 12 is a schematic illustration showing construction of a plasmid IR/DR-puro for assessing the transposon activity of IR/DR-NTA-Ad/pSP.

For Assessment of the transposon activity of a transposon vector IR/DR-NTA-Ad/pSP obtained in Example 3(2), a plasmid (IR/DR-puro) for assessing the transposon activity with a puromycin resistant enzyme gene inserted therein was constructed by inserting into SalI site of said transposon vector a DNA fragment of about 1.7 kbp obtained by digestion with restriction enzyme SalI of an expression plasmid pPGKpuro in which a puromycin resistant enzyme gene (Gomez L E et al., *Nucleic Acids Res.*, 19, 3465, 1991) and a poly(A) addition signal sequence from PGK were linked under control of a PGK promoter (Adra C N, *Gene,* 60, 65-74, 1987) (FIG. 12).

Example 5

Construction of a Modified Transposon Vector with Insertion of a Lox Sequence

In the subsequent Examples, construction of vectors, donor plasmids and expression plasmids of the enzyme Cre undertaking a recombination reaction, and a replacement reaction will be described for use in Cre-Lox recombination system. However, other recombination systems may also be used.

(1) Construction of a Modified Transposon Vector with Insertion of a Mutated Lox Sequence (IR/DR-Ad/5'Lxp)

Figure 13:
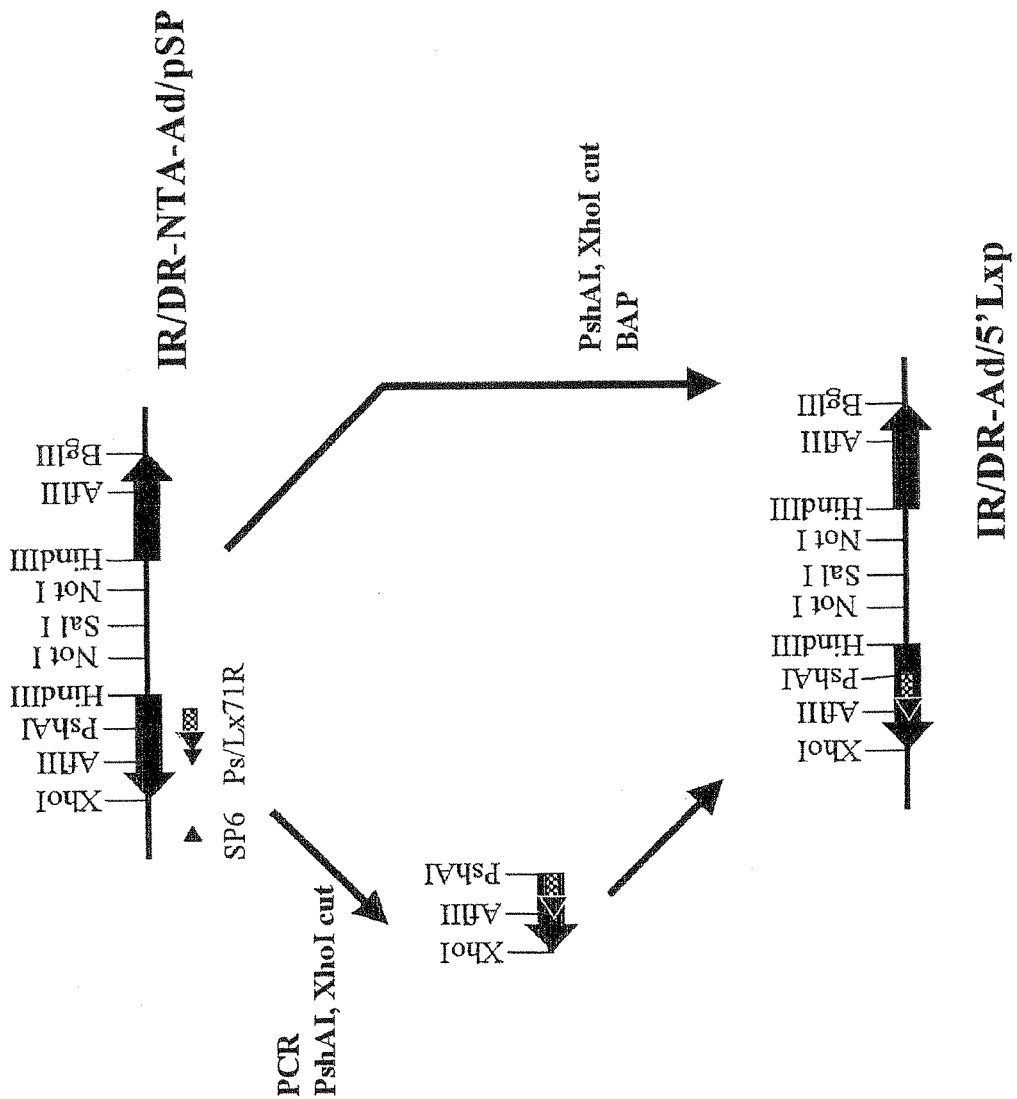
FIG. 13 is a schematic illustration showing construction of a modified transposon vector IR/DR-Ad/5'Lxp wherein a mutated Lox71 sequence is inserted into 5'-TIR sequence.

Using IR/DR-NTA-Ad/pSP as a template, PCR was performed with SP6 primer (SEQ ID NO: 27) and a primer Ps/Lx71R (SEQ ID NO: 28) with insertion of Lox71 sequence, a mutant of LoxP sequence, to amplify a DNA fragment of about 200 bp wherein Lox71 sequence was added within 5'-TIR sequence which was recovered. PCT was carried out as described in Example 1 except for 35 cycles of denaturation at 94° C. for 1 min., annealing at 55° C. for 2 min. and elongation at 72° C. for 2 min. This DNA fragment was once cloned using TOPO TA Cloning kit (INVITROGEN), digested with restriction enzymes PshAI and XhoI and inserted into IR/DR-NTA-Ad/pSP, which has previously been digested with the same restriction enzymes and then BAP treated, construct a modified transposon vector IR/DR-Ad/5'Lxp wherein mutant Lox71 sequence was inserted between the two DR sequences present within 5'-TIR sequence (FIG. 13). A mutant Lox71 sequence was inserted into 5'-TIR sequence such that a distance between the two DR sequences (a number of nucleotides of DNA) will not be changed after insertion by suitably designing the primer so that the Lox71 sequence to be inserted has the same length as that of the original DNA sequence.

(2) Insertion of LoxP Sequence into 3'-TIR Sequence

Figure 14:
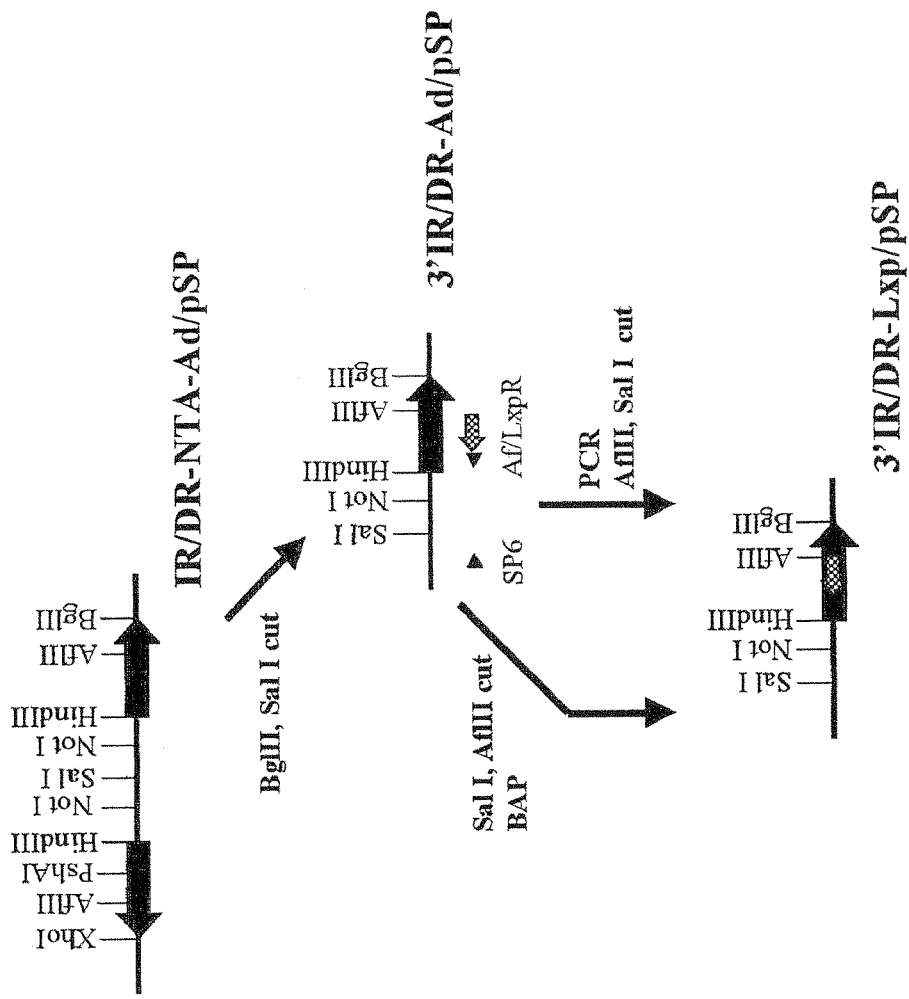
FIG. 14 is a schematic illustration showing construction of a plasmid 3'IR/DR-Lxp/pSP wherein a LoxP sequence is inserted into 3'-TIR sequence.

IR/DR-NTA-Ad/pSP constructed in Example 3(2) was digested with restriction enzymes SalI and BglII and subcloned into pSP72 (Promega), which has previously been digested with the same restriction enzymes and then SAP treated, to construct 3'IR/DR-Ad/pSP. Using the 3'IR/DR-Ad/pSP as a template, PCR was performed with SP6 primer (SEQ ID NO: 27) and a primer Af/LxpR (SEQ ID NO: 29) in which LoxP sequence was inserted under the same conditions as in Example 5(1) to amplify a DNA fragment of about 400 bp, wherein LoxP sequence was added within 3'-TIR sequence, which was recovered. This DNA fragment was once cloned using TOPO TA Cloning kit (INVITROGEN), digested with restriction enzymes AflII and SalI and inserted into 3'IR/DR-Ad/pSP, which has previously been digested with the same restriction enzymes and then BAP treated, to construct a modified transposon vector 3'IR/DR-Lxp/pSP wherein LoxP sequence was inserted between the two DR sequences present within 3'-TIR sequence (FIG. 14). The 3'-TIR sequence in the thus obtained vector was designed such that a distance between the two DR sequences (a number of nucleotides of DNA) will not be changed after insertion as in Example 5(1).

(3) Insertion of LoxP/poly(A) Signal Sequences into 3'-TIR Sequence

Figure 15:
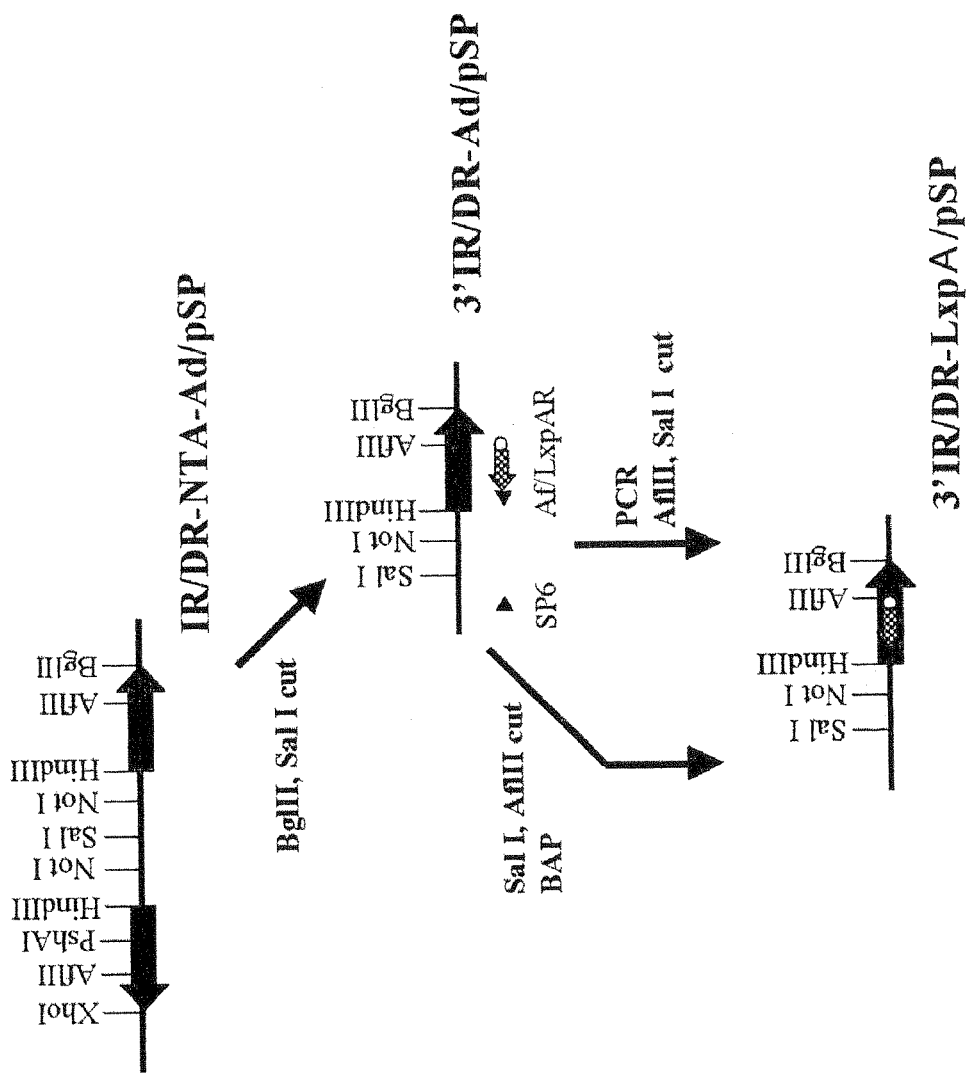
FIG. 15 is a schematic illustration showing construction of a plasmid 3'IR/DR-LxpA/pSP wherein a LoxP sequence and a poly(A) addition signal sequence are inserted into 3'-TIR sequence.

Using the 3'IR/DR-Lxp/pSP constructed in Example 5(2) as a template, PCR was performed with SP6 primer and a primer Af/LxpAR (SEQ ID NO: 30) in which a poly(A) addition signal sequence derived from bovine growth hormone was added downstream LoxP sequence under the same conditions as in Example 5(1) to amplify a DNA fragment of about 400 bp, wherein LoxP sequence together with the poly(A) addition signal sequence downstream thereof were added within 3'-TIR sequence, which was recovered. This DNA fragment was once cloned using TOPO TA Cloning kit (INVITROGEN), digested with restriction enzymes AflII and SalI and inserted into 3'IR/DR-Ad/pSP, which has previously been digested with the same restriction enzymes and then BAP treated, to construct a modified transposon vector 3'IR/DR-LxpA/pSP which bears LoxP sequence together with the poly(A) addition signal sequence downstream thereof (FIG. 15). The 3'-TIR sequence in the thus obtained 3'IR/DR-LxpA/pSP was designed such that a distance between the two DR sequences (a number of nucleotides of DNA) will not be changed after insertion as in Example 5(1).

(4) Construction of a Modified Transposon Vector with Insertion of a Mutated Lox and LoxP Sequences (IR/DR-Ad/LxDb)

Figure 16:
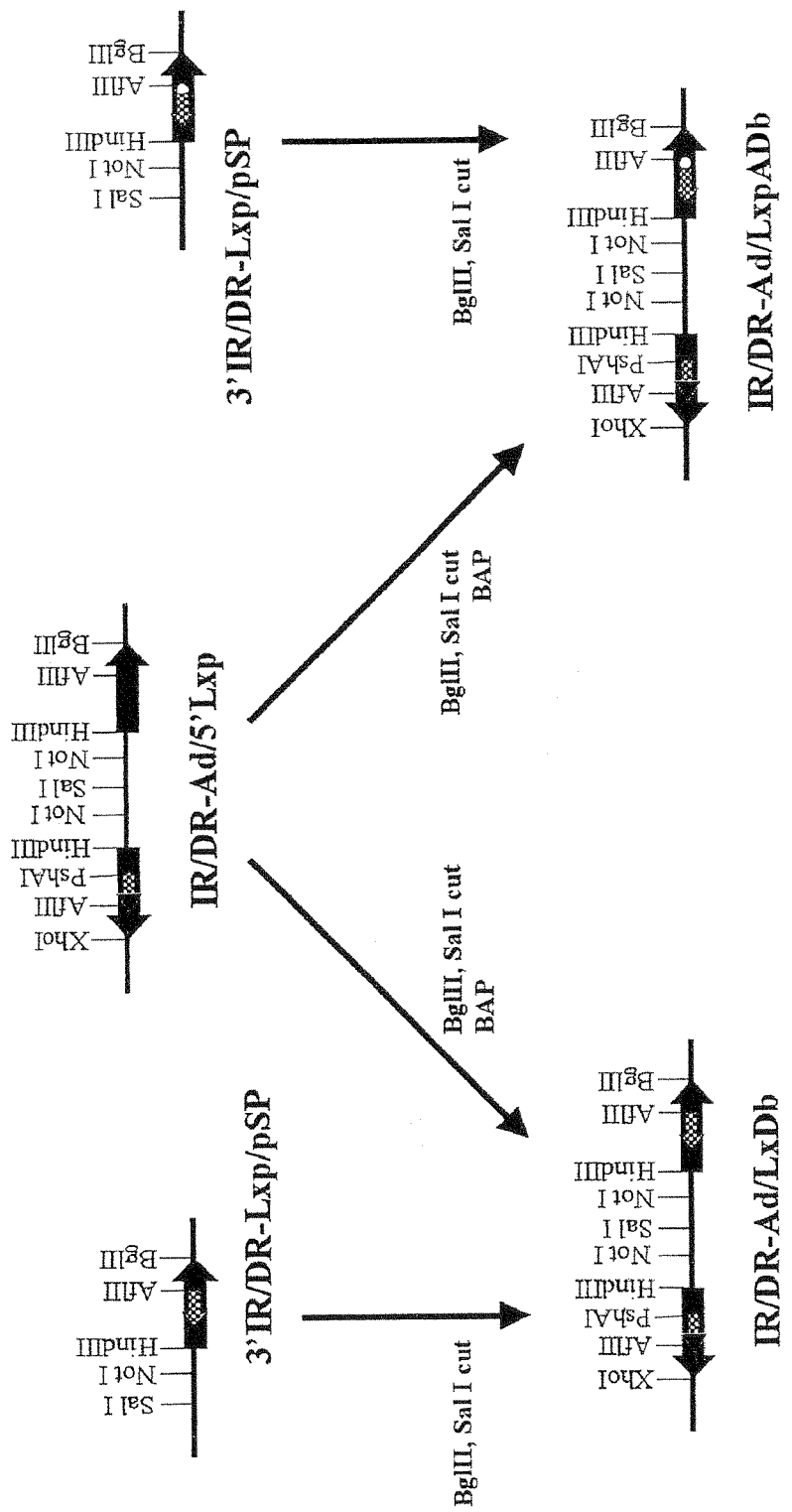
FIG. 16 is a schematic illustration showing construction of a modified transposon vector IR/DR-Ad/LxDb wherein a Lox71 sequence is inserted into 5'-TIR sequence and a LoxP sequence is inserted into 3'-TIR sequence and a modified transposon vector IR/DR-Ad/LxpADb wherein a Lox71 sequence is inserted into 5'-TIR sequence and a LoxP sequence and a poly(A) addition signal sequence are inserted into 3'-TIR sequence.

3'IR/DR-Lxp/pSP constructed in Example 5(2) was digested with restriction enzymes BglII and SalI and the resulting fragment was inserted into IR/DR-Ad/5'Lxp constructed in Example 5(1), which has previously been digested with the same restriction enzymes and then BAP treated, to construct a transposon vector IR/DR-Ad/LxDb bearing Lox71 within 5'-TIR sequence and LoxP sequence within 3'-TIR sequence (FIG. 16).

(5) Construction of a Modified Transposon Vector with Insertion of a Mutated Lox and LoxP/poly(A) Addition Signal Sequences (IR/DR-Ad/LxpADb)

3'IR/DR-LxpA/pSP constructed in Example 5(3) was digested with restriction enzymes BglII and SalI and the resulting fragment was inserted into IR/DR-Ad/5'Lxp constructed in Example 5(1), which has previously been digested with the same restriction enzymes and then BAP treated, to construct a modified transposon vector IR/DR-Ad/LxpADb which bears Lox71 within 5'-TIR sequence and LoxP sequence together with the poly(A) addition signal sequence downstream thereof within 3'-TIR sequence (FIG. 16).

Example 6

Figure 17:
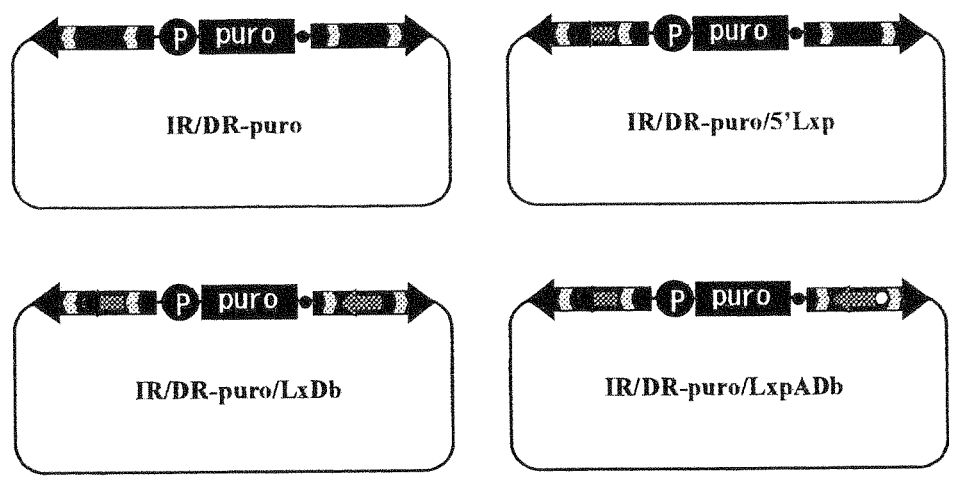
FIG. 17 shows plasmids for assessing the transposon activity of various modified transposon vectors wherein a Lox sequence is inserted between DR sequences.

Construction of Plasmid for Assessing Transposon Activity of Modified Transposon Vector with Insertion of Lox Sequence For assessment of the transposon activity of IR/DR-Ad/5'Lxp constructed in Example 5(1), IR/DR-Ad/LxDb constructed in Example 5(4) and IR/DR-Ad/LxpADb constructed in Example 5(5), plasmids IR/DR-puro/5'Lxp, IR/DR-puro/LxDb and IR/DR-puro/LxpADb for assessing the transposon activity with an expression cassette of a puromycin resistant enzyme gene inserted therein were constructed by inserting into each SelI site of said transposon vectors a DNA fragment of about 1.7 kbp obtained by digestion with restriction enzyme SalI of an expression plasmid pPGKpuro in which a puromycin resistant enzyme gene and a poly(A) addition signal sequence from PGK were linked under control of a PGK promoter (FIG. 17).

Example 7

Comparison of Introduction Efficiency of Various Plasmids for Assessing Transposon Activity with HeLa Cells (1) Purification of Various Plasmids for Assessing Transposon Activity The transposase expression plasmid pCAGGS/SB constructed in Example 2 and the plasmids IR/DR-puro, IR/DR-puro/5'Lxp, IR/DR-puro/LxDb and IR/DR-puro/LxpAD for assessing the transposon activity constructed in Examples 4 and 6 were introduced into competent cells JM109 (TOYOBO) as instructed by attached protocol to prepare recombinant cells bearing each of the plasmids. The recombinant cells were cultured in L-Broth containing 50 mg/ml ampicillin overnight. The obtained culture of each of the recombinant cells was purified with Plasmid Maxi Kit (QIAGEN) as instructed by protocol attached thereto. Each of the purified plasmids was dissolved in autoclaved distilled water and, measuring absorbance at 260 nm of wave length to determine their concentration, was stored at −20° C. till use.

(2) Introduction of Various Plasmids for Assessing Transposon Activity into HeLa Cells Various plasmids for assessing the transposon activity were introduced into HeLa cells as described below. To 250 μl Opti-MEM I Reduced-Serum Medium (INVITROGEN) was added 10 μl Trans-IT LT1 (TaKaRa). The mixture was stirred and kept to stand at room temperature for 10 min. To the mixture were then added 1.5 μg of pCAGGS/SB prepared in Example 2 and 1.5 μg of either of the plasmids (any one of IR/DR-puro, IR/DR-puro/5'Lxp, IR/DR-puro/LxDb or IR/DR-puro/LxpADb) for assessing the transposon activity constructed in Examples 4 and 6. The mixture was stirred and further kept to stand at room temperature for 15 min. to form a DNA/Trans-IT LT1 complex. The obtained complex was added to HeLa cells prepared just prior to transfection and the cells were cultured at 37° C. for 6 hours. Supernatant was removed, 2 ml/well 10% complete DMEM was added and culture continued in the presence of 5% $CO_2$ at 37° C. for 2 days.

For HeLa cells as described above, $1.7 \times 10^5$ cells/2 ml/well of HeLa cells from human cervix cancer (Dainippon Pharma Co., Ltd.) cultured and maintained in DMEM (Sigma) containing 10% fetal bovine serum (HyClone) and 1/100 amount of penicillin-streptomycin (INVITROGEN) (hereinafter also referred to as "10% complete DMEM") were plated to 6-well plate (Corning incorporated) and cultured for about a day and, after removal of culture supernatant and washing with Dulbecco's phosphate buffer (Sigma), 0.8 ml Opti-MEM I Reduced-Serum Medium was added. For control, HeLa cells were used wherein the plasmid for assessing the transposon activity alone was introduced with no addition of pCAGGS/SB.

(3) Assessment of Introduction Efficiency of Various Plasmids for Assessing Transposon Activity HeLa cells, wherein various plasmids for assessing the transposon activity were introduced, prepared in Example 7(2) were washed with Dulbecco's phosphate buffer (Sigma) and treated with 200 μl of 0.05% trypsin solution (INVITROGEN) at 37° C. for 3 min. and then 2 ml of 10% complete DMEM was added to quench the enzymatic reaction. This solution of cells was dispersed by pipetting. To an aliquot of 20 μl was added an equal amount of trypan blue dye (INVITROGEN) and a cell count was measured with a hemocytometer. Cells ($3.8 \times 10^4$) taken from the cell suspension were added to a dish (Corning Incorporated) of 10 cm diameter wherein 10 ml of 10% complete DMEM containing 1 μg/ml puromycin (BD Bioscience) has previously been added and cultured at 37° C. in the presence of 5% $CO_2$. While culture, a culture medium was exchanged at least once with 10% complete DMEM containing 1 μg/ml puromycin. After culture for 10 to 14 days, culture supernatant was removed and the dish was washed with Dulbecco's phosphate buffer. A solution (1 ml/dish) of 0.2% Crystal violet (KISHIDA CHEMICAL Co., Ltd.) in 20% methanol (Wako Pure Chemical Industries, Ltd.) was added to the dish to stain and fix the cells at room temperature for 30 min. The dish was then washed with tap water and, after air dry, a colony number was measured.

A ratio ($C_{SB}/C_N$) of a colony number ($C_{SB}$) of puromycin resistant cells wherein both pCAGGS/SB and various plasmids for assessing the transposon activity were introduced to a colony number ($C_N$) of puromycin resistant cells wherein any of various plasmids for assessing the transposon activity alone was introduced was calculated and was used as an index for assessing introduction efficiency of various plasmids for assessing the transposon activity.

Various plasmids for assessing the transposon activity were all found to be incorporated into chromosome of HeLa cells at a high rate and the introduction efficiency was by 15 to 50 folds higher than that where any of various plasmids for assessing the transposon activity alone was introduced (Table 3). This result indicates that introduction efficiency into cells by the transposon activity would scarcely be affected by Lox sequence which was inserted into TIR sequence such that a distance (a number of nucleotides) between the two DR sequences in TIR sequence will not be changed after insertion.

TABLE 3

Transposon activity of various plasmids for assessing the activity

| Plasmid | Lox Sequence | | $C_{SB}/C_N$ |
|---|---|---|---|
| | 5'TIR | 3'TIR | |
| IR/DR-puro | 0 | 0 | 20.7 |
| IR/DR-puro/5'Lxp | 1 | 0 | 49.3 |
| IR/DR-puro/LxDb | 1 | 1 | 15.4 |
| IR/DR-puro/LxpADb | 1 | 1 | 19.9 |

Example 8

Replacement of Foreign Gene by Cre-Lox Recombination System (1) Cloning of HeLa Cells Wherein Transposon Vector (IR/DR-Puro/LxpADb) is Introduced IR/DR-puro/LxpADb was introduced into HeLa cells as described in Example 7(2). On Day 2 after culture, the cells were subcultured on dish (Corning Incorporated) of 10 cm diameter and cultured on 10% complete DMEM containing 1 μg/ml puromycin (BD Bioscience) for 2 weeks. The dish was washed with Dulbecco's phosphate buffer (Sigma). Dulbecco's phosphate buffer (10 ml) containing 0.5% EDTA (Wako Pure Chemical Industries, Ltd.) was added to the dish and the dish was kept to stand at room temperature for 5 min. With a microscope placed within a bioguard hood, a single colony of the HeLa cells generated on the dish was peeled off physically, added to 48-well plate wherein 500 μl of 10% complete OMEN containing 1 μg/ml puromycin (BD Bioscience) has previously been added and cultured at 37° C. in the presence of 5% $CO_2$. The thus cloned puromycin resistant HeLa cells (hereinafter also referred to as "HeLa/puro cells") were successively expanded to culture on dish of 10 cm diameter. When grown in full sheet, the cells were washed with Dulbecco's phosphate buffer (Sigma), treated with trypsin and recovered. The cells ($10^6$) were stored in liquid nitrogen and the rest was used for subsequent extraction of chromosomal DNAs.

(2) Construction of Plasmid for Gene Replacement (Donor Plasmid and Cre Expression Plasmid)

(a) Construction of Donor Plasmid (pLx/GFP/neo/pA(-))

Figure 18:
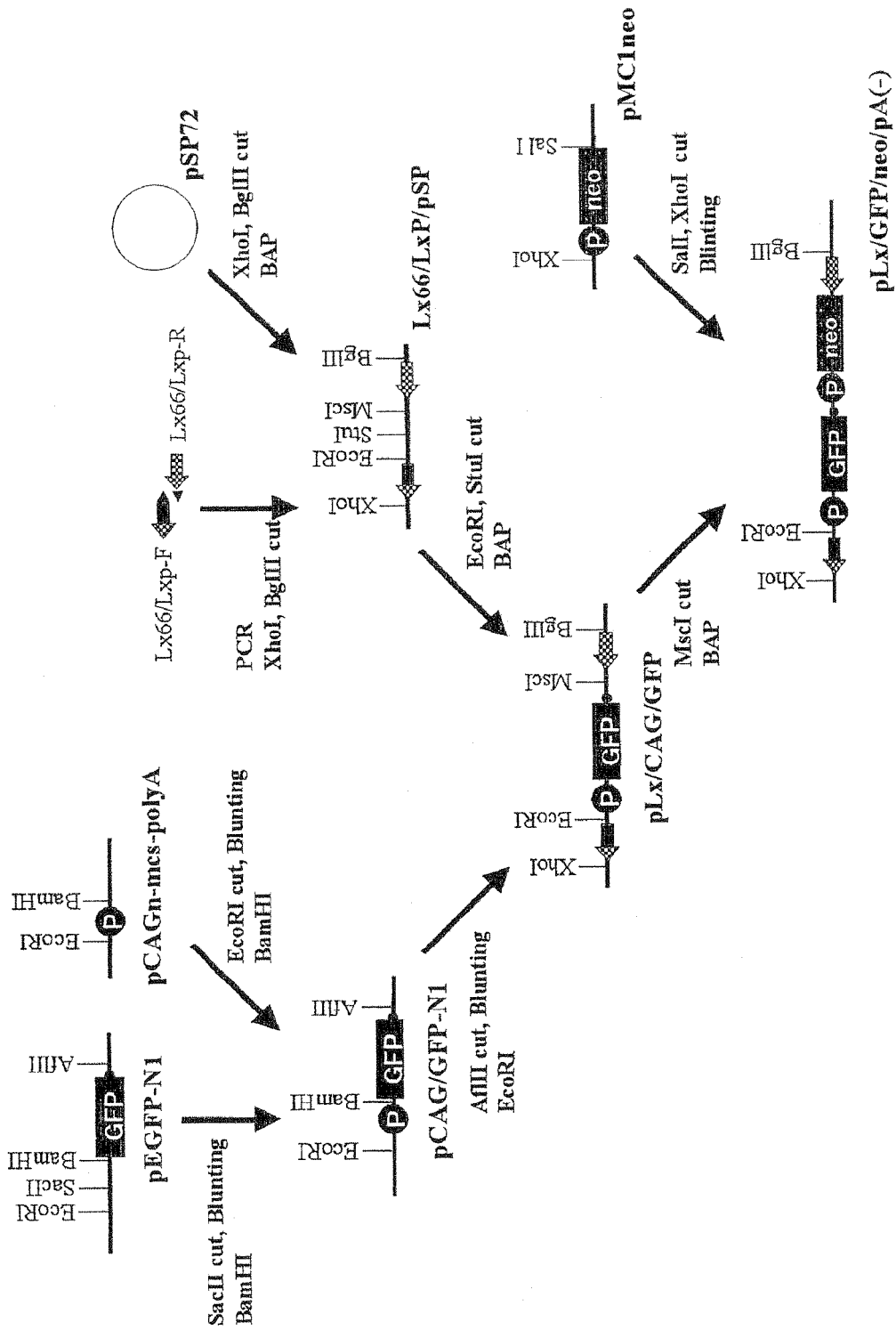
FIG. 18 is a schematic illustration showing construction of a donor plasmid pLx/GFP/neo/pA(−) used for gene replacement with Cre-Lox system.

As illustrated in the scheme of FIG. 18, a donor plasmid pLx/GFP/neo/pA(-) was constructed wherein expression cassettes of GFP gene and of neo gene are flanked by Lox sequences. First, an expression vector pCAGn-mcs-polyA for animal cells (Japanese patent application No. 165249/1996) was digested with restriction enzyme SalI, the cleaved sites were blunted with DNA Blunting Kit (TaKaRa) and linked to each other to remove the SalI recognition site. The plasmid was then digested with restriction enzyme EcoRI, the cleaved sites were blunted with DNA Blunting Kit (TaKaRa) and digested with restriction enzyme BamHI to provide a DNA fragment of about 1.5 kbp. The resulting DNA fragment was inserted into pEGFP-N1 (BD Bioscience) bearing GFP gene, which, after digestion with restriction enzyme SacII and the similar treatment of the cleaved sites for blunting, has previously been digested with restriction enzyme BamHI and then BAP treated, to construct pCAG/GFP-N1. This plasmid was digested with restriction enzyme AflII and, after the treatment of the cleaved sites for blunting, was further digested with restriction enzyme EcoRI to recover a DNA fragment of about 2.8 kbp.

A primer Lx66/LxP-F (SEQ ID NO: 31) bearing XhoI recognition site at its 5' end and Lox66 sequence in its interior and a primer Lx66/LxP-R (SEQ ID NO: 32) bearing BglII recognition site at its 5' end and LoxP sequence in its interior were mixed together and PCR was performed without addition of a template DNA (25 nucleotide residues at 3' end of Lx66/LxP-F and 25 nucleotide residues at 3' end of Lx66/LxP-R being homologous to each other). The amplified fragment of about 120 bp was digested with restriction enzymes XhoI and BglII and inserted into a cloning vector pSP72, which has previously been digested with the same restriction enzymes and then BAP treated, to construct Lx66/LxP/pSP.

Next, the DNA fragment of about 2.8 kbp obtained above was inserted into Lx66/LxP/pSP, which has previously been digested with restriction enzymes EcoRI and MscI and then BAP treated, to construct pLx/CAG/GFP. pMC1neo (STRATAGENE) was digested with restriction enzymes BamHI and XhoI and the cleaved sites were blunted to recover a DNA fragment of about 1.1 kbp. The resulting DNA fragment was inserted into pLx/CAG/GFP, which has previously been digested with restriction enzyme MscI and then BAP treated, to construct a donor plasmid pLx/GFP/neo/pA(–) wherein an expression cassette of a foreign gene (GFP) and an expression cassette of neo gene with no poly(A) addition signal as a consequence of a poly(A) trap method were flanked by Lox sequences.

(b) Provision of Expression Plasmid of Cre Gene (pCAGGS/Cre)

An expression plasmid of Cre gene (pCAGGS/Cre) was generously presented by Assistant Professor Araki of Kumamoto University, Gene Technology Center.

(3) Introduction of Donor Plasmid and Expression Plasmid of Cre Gene into HeLa/Puro Cells Each 1.5 µg of pLx/GFP/neo/pA(–) and pCAGGS/Cre constructed and obtained in Example 8(2) were introduced into $2 \times 10^5$ cells/well of HeLa/puro cells obtained in Example 8(1) as described in Example 7(2). On Day 2 after culture, the cells were washed with Dulbecco's phosphate buffer (Sigma) and treated with 200 µl of 0.05% trypsin solution (INVITROGEN) at 37° C. for 3 min. and 2 ml of 10% complete DMEM was added to quench the reaction. A suspension of the cells was subcultured on dish (Corning Incorporated) of 10 cm diameter and cultured on 10% complete DMEM medium containing 750 µg/ml G418 (TaKaRa) for 10 to 14 days. A G418 resistant single colony was recovered as described in Example 8(1), maintained and subcultured on 10% complete medium containing 750 µg/ml G418 and cultured on 48-well plate (Corning Incorporated) till grown in almost full sheet. The thus cloned G418 resistant cells were divided into two on 24-well plate. One was cultured on 10% complete medium containing 750 µg/ml G418 whereas the other was cultured on 10% complete medium containing 1 µg/ml puromycin for about a week. Such a colony that grew on 10% complete medium containing 750 µg/ml G418 but died on 10% complete medium containing 1 µg/ml puromycin was selected. After it was verified that G418 resistant, puromycin non-resistant clone (hereinafter also referred to as "HeLa/neo cells") emitted green fluorescence as a consequence of GFP expression under a fluorescence microscope, said HeLa/neo cells were expanded to culture on dish of 10 cm diameter and recovered. The cells ($10^6$) were stored in liquid nitrogen and the rest was used for preparation of chromosomal DNAs as described below.

(4) Preparation of Chromosomal DNAs from HeLa/Puro and HeLa/Neo Cells

Each $5$-$10 \times 10^6$ cells of HeLa/puro and HeLa/neo were centrifuged at 1500 r.p.m. to recover cells. The cells were suspended in 220 µl of 10 mM Tris-HCl/1 mM EDTA solution (hereinafter referred to as "TE"). To the suspension was added 200 µl per $10^6$ cells of a lysis buffer (10 mM Tris-HCl, 0.1 M EDTA, 0.5% SDS, final concentration 20 µg/ml RNase (Sigma), pH 8.0) and the mixture was kept to stand at 37° C. An hour later, proteinase K (Invitrogen) was added at a final concentration of 100 µg/ml and the mixture was stirred at 50° C. for 3 hours for reaction. After reaction, an equal amount of phenol saturated with TE was added and the mixture was shaken for 10 min. and centrifuged to recover a separated aqueous layer. This procedure was repeated until an intermediate layer was no longer observed. To an aqueous layer finally recovered were added ⅕ volume of 10 M ammonium chloride and 2 volume of ethanol and the mixture was stirred with glass rod. While stirring, precipitated fibrous chromosomal DNAs were wound around glass rod. After washing 70% ethanol, the DNAs were air dried and dissolved in 200 µl TE. After solution, a DNA concentration was calculated from absorbance at 260 nm of wave length.

(5) Verification of Gene Replacement in Chromosomal DNAs of HeLa/Puro and HeLa/Neo Cells by Southern Blot First, RI labeled probes were prepared for detection of neo and puromycin resistant enzyme genes. PCR was performed with pMC1neo (STRATAGENE) as a template using primers neo/1072F (SEQ ID NO: 37) and neo/1501R (SEQ ID NO: 38) for a probe for detection of a neo gene (neo probe) and with pPGKpuro as a template using primers puro In/S (SEQ ID NO: 39) and puro 2 (SEQ ID NO: 40) for a probe for detection of a puromycin resistant enzyme gene (puro probe). The PCR products were electrophoresed on agarose gel. DNA fragments of interest were recovered with GFX PCR DNA and Gel Band Purification Kit (Amersham Bioscience). These DNA fragments were then labeled with [α-32P] dCTP (Amersham Bioscience) using 100-200 ng of these DNA fragments as a template with BcaBEST Dideoxy Sequencing Kit (TaKaRa) as instructed in protocol attached thereto to provide neo and puro probes.

Southern blot was performed with these probes. Each 20 µg of the chromosomal DNAs from HeLa/puro and HeLa/neo cells prepared in Example 8(4) and each 2 ng of IR/DR-puro/LxpADb constructed in Example 6 and pLx/GFP/neo/pA(–) constructed in Example 8(2) were digested with restriction enzyme AflII and separated on 0.7% agarose gel (BioRAD). The separated DNAs were transferred to Hybond-N+ filter (Amersham Bioscience) in 0.4M NaOH solution using capillary phenomenon overnight. After reaction in Rapid Hyb buffer (Amersham Bioscience) at 65° C. for 1 hour, said filter was transferred to fresh Rapid Hyb buffer. To this was added neo or puro probe which was boiled at 100° C. for 5 min. and then rapidly cooled in ice. The mixture was further reacted at 65° C. overnight. The filter was recovered, rinsed in 2×SSC (0.3M sodium chloride, 0.03M sodium citrate) solution containing 0.5% SDS and washed in the same solution at room temperature for 15 min. Then, washing in 0.1×SSC solution containing 0.1% SDS at 65° C. for 30 min. was repeated twice or thrice and finally the filter was rinsed with 0.1×SSC and dehydrated on filter paper. The filter was wrapped in Saran Wrap (Asahi Kasei Corporation), put in a cassette for autoradiography and exposed to BioMax MS film (Kodak) for 4 days.

Figure 19:
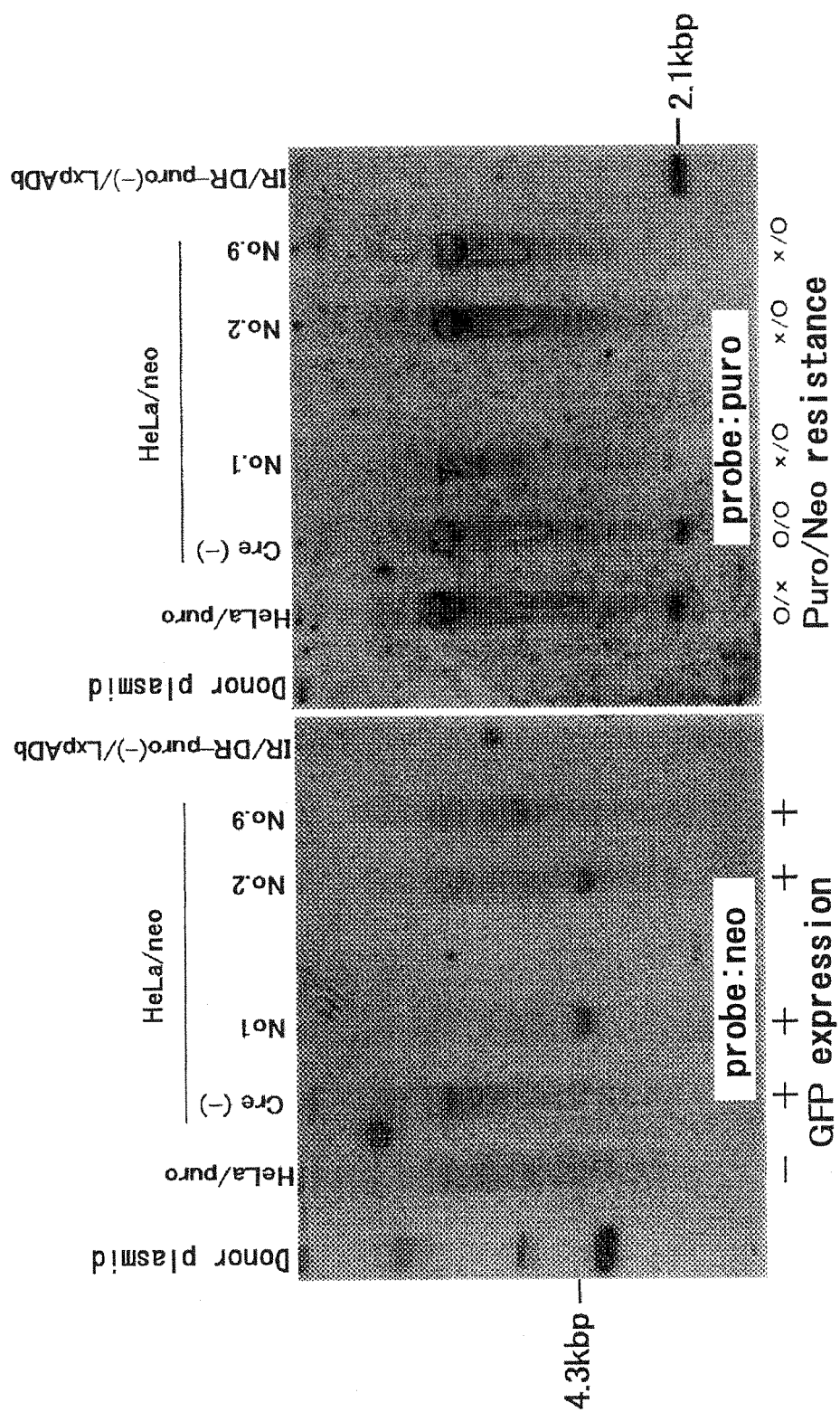
FIG. 19 shows results of Southern blot analysis of HeLa/neo obtained from gene replacement with Cre-Lox system of HeLa/puro which is obtained by introduction of a plasmid IR/DR-puro/LxpADb for assessing the transposon activity.

The results are shown in FIG. 19. For HeLa/puro cells wherein IR/DR-puro/LxpADb was introduced before gene replacement (No. 2; accepter clone), no signal reacting with neo probe was observed. For HeLa/neo cells wherein both a donor plasmid pLx/GFP/neo/pA(−) and pCAGGS/Cre were introduced, however, a signal of about 4.3 kbp was detected (No. 1 and No. 2). For positive control, pLx/GFP/neo/pA(−), a signal was detected but with a different size from that of the HeLa/neo cells due to absence of restriction enzyme AflII recognition site used for digestion. On the other hand, when pure probe was used, a signal of about 2.4 kbp, the same size as positive control IR/DR-puro/LxpADb, was detected for the HeLa/puro cells before gene replacement whereas no signal was detected for the HeLa/neo cells after gene replacement (No. 1, No. 2 and No. 9). From this result, it is estimated that the puromycin resistant enzyme gene in IR/DR-puro/LxpADb inserted into chromosomal DNAs was replaced with neo and GFP genes (FIG. 20).

Figure 20:
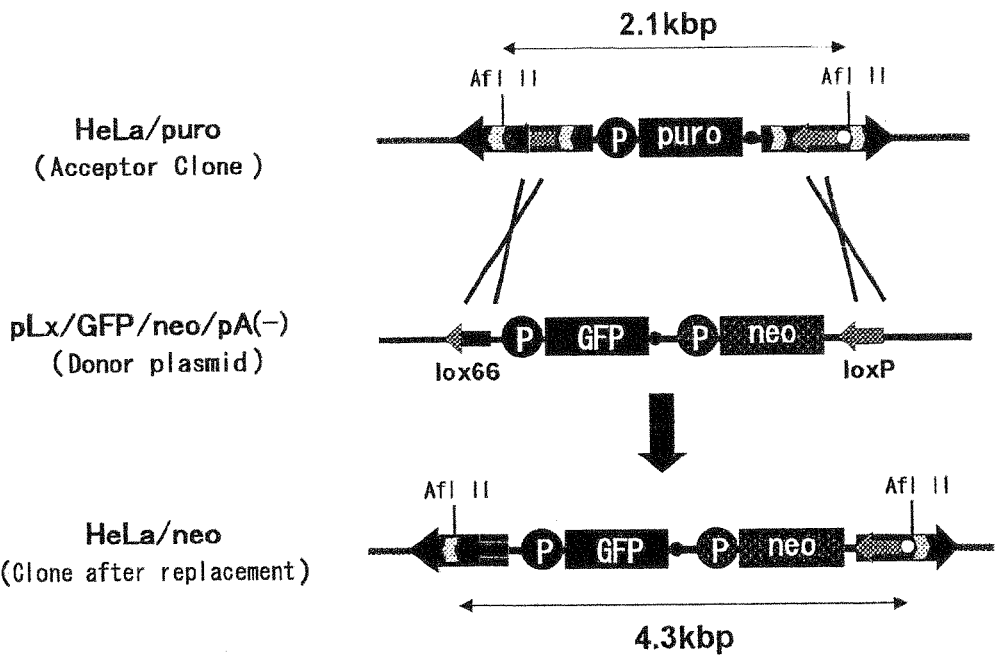
FIG. 20 is a schematic illustration showing a preparation of HeLa/neo estimated from the Southern blot analysis.

(6) Investigation of Gene Replacement Sites in Chromosomal DNAs of HeLa/Neo Cells In order to verify that the gene replacement as shown in FIG. 20 has just occurred on Lox sequences, PCR was performed using BD GenomeWalker Universal Kit (BD Bioscience) and then the vicinity of Lox sequences inserted within both 5′- and 3′-TIR sequences was sequenced (hereinafter also referred to as "Genome Walking"). First, the chromosomal DNAs of the HeLa/neo cells purified in Example 8(4) were digested with any of restriction enzymes EcoRV, PvuII, SspI and NaeI, which may generate blunt-ends, and to the resulting fragments was added an adaptor attached to the kit as instructed by protocol attached thereto. The obtained fragments were used as a template for subsequent PCR.

In order to investigate the insertion site at the 5′-end, a first round PCR as performed with AP1 primer (SEQ ID NO: 41) having a sequence derived from the adaptor and a primer CAG/GSP2 (SEQ ID NO: 42) prepared based on CAG promoter sequence. Then, taking 1 µl of the PCR reaction, second round PCR was performed with AP2 primer (SEQ ID NC: 43) having a sequence derived from the adaptor and a primer CAG/GSP4 (SEQ ID NO: 44) prepared based on CAG promoter sequence.

On the other hand, in order to investigate the insertion site at the 3′-end, a first round PCR was performed with AP1 primer and a primer neo/1306F (SEQ ID NO: 45) prepared based on neo gene sequence with a reaction of volume of 25 µl. Then, a second round PCR was performed with AP2 primer and a primer neo/1389F (SEQ ID NO: 46) prepared based on neo gene sequence.

A total amount of the reaction after the second round PCR was electrophoresed on 1% agarose gel (BioRAD) to separate the amplified DNA fragments. Said DNA fragments were recovered from the agarose gel using GFX PCR DNA and Gel Band Purification Kit (Amersham Bioscience) and cloned into a plasmid pCR2.1 using TOPO TA Cloning kit (INVITROGEN). The amplified portions of the DNA fragments were sequenced using BigDye Terminator Cycle Sequencing FS Ready Reaction Kit and ABI PRISM 310 Genetic Analyzer from Applied Biosystems (ABI).

Figure 21:
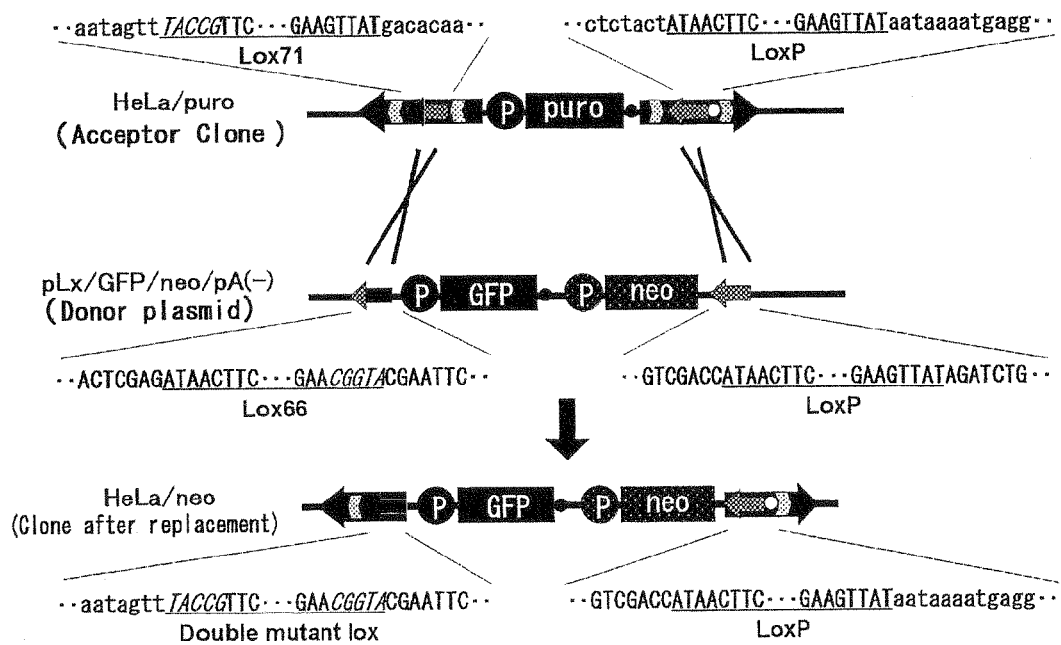
FIG. 21 shows results of nucleotide sequencing of the vicinity of Lox sequences present within 5'- and 3'-TIR sequences of HeLa/puro and HeLa/neo as revealed by Genome walking.

As a result, it was found that the outside portion of Lox sequence inserted within 5′-TIR sequence was identical to that of IR/DR-puro/LxpADb initially introduced whereas the inside portion of Lox sequence was identical to that of pLx/GFP/neo/pA(−) introduced for replacement. Similarly, the outside portion of Lox sequence inserted within 3′-TIR sequence was identical to that of IR/DR-puro/LxpADb initially introduced whereas the inside portion of Lox sequence was identical to that of pLx/GFP/neo/pA(−) introduced for replacement. Furthermore, the investigated Lox sequence within 5′-TIR sequence was such that the sequence of the outside Cre-binding portion was that of Lox71 used in IR/DR-puro/LxpADb initially introduced whereas the sequence of the inside Cre-binding portion was that of Lox66 used in pLx/GFP/neo/pA(−) for replacement. From these nucleotide sequences, it can be verified that the HeLa/neo cells were generated from the HeLa/puro cells wherein IR/DR-puro/LxpADb was inserted by simultaneous introduction of pCAGGS/Cre and pLx/GFP/neo/pA(−) which induced recombination on the Lox sequences to replace the region flanked by the Lox sequences of IR/DR-puro/LxpADb (an expression cassette of a puromycin resistant enzyme gene) with the region flanked by the Lox sequences of pLx/GFP/neo/pA(−) (expression cassettes of GFP and neo gene) (FIG. 21).

Figure 22:
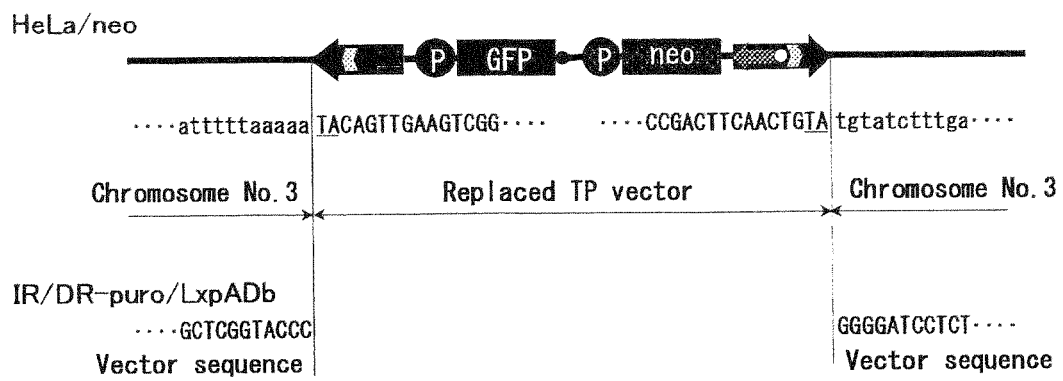
FIG. 22 shows the position in chromosomal DNAs of HeLa/neo at which a modified transposon vector is introduced as revealed by Genome walking.

Besides, upon insertion of the expression cassettes of GFP and of neo gene into chromosomal DNAs of HeLa/neo cells, the sequences outside Lox sequences up to the dinucleotide TA at the ends of both 5′- and 3′-TIR sequences were those of IR/DR-puro/LxpADb initially introduced. However, it was found that sequences further outside these sequences outside the TA were identical to those on human Chromosome No. 3 as registered in nucleotide sequence data base (GeneBank) of NCBI of USA. This result indicates that the transposon vector IR/DR-puro/LxpADb introduced into HeLa cells was transposed and inserted into Chromosome No. 3 of said HeLa cells by the transposon activity induced by a transposase expressed from the expression cassette of a transposase which was simultaneously inserted into the cells (FIG. 22).

The results as described above show that it is possible to introduce a gene into chromosomal DNAs by the transposon activity using a transposon vector wherein Lox sequences are inserted within 5′- and 3′-TIR sequences of a transposon gene and then to replace said gene with another gene by Cre-Lox recombination system via the Lox sequences within the TIR sequences. Furthermore, the results show that by exploiting the gene replacement reaction, it is possible to remove the inner one of the DR regions present by two within each of 5′- and 3′-TIR sequences of a transposon vector initially introduced.

Example 9

Assessment of Transposon Activity after Destruction of TIR Sequences by Gene Replacement (1) Introduction of IR/DR-Puro/LxpADb Alone into HeLa Cells and Gene Replacement by Donor Plasmid Puromycin resistant HeLa cells (hereinafter also referred to as "Single/HeLa/puro cells") wherein IR/DR-puro/LxpADb alone was introduced as described in Example 7(2) and cloning was done as described in Example 8(1) were cultured on 6-well plate till grown in full sheet, recovered and $10^6$ cells were stored in liquid nitrogen. The rest of $1.7 \times 10^5$ cells/well were plated on 6-well plate, cultured overnight and introduced with pLx/GFP/neo/pA(−) and pCAGGS/Cre as described in Example 7(2). On Day 2 after culture, the cells were recovered, suspended in 10 ml of 10% complete medium containing 750 µg G418, plated on dish of 10 cm diameter and cultured for about 10 days. G418 resistant HeLa cells (hereinafter also referred to as "Single/HeLa/neo cells") cloned as described in Example 8(1) were cultured on dish of 10 cm diameter till grown almost in full sheet and recovered. Chromosomal DNAs were purified from said cells as described in Example 8(5) and, after calculating a DNA concentration from absorbance of $OD_{260}$, were stored at $-20°$ C.

(2) Investigation of Gene Replacement Sites in Chromosomal DNAs of Single/HeLa/Neo Cells For the chromosomal DNAs of Single/HeLa/neo cells obtained in Example 9(1), the gene replacement sites were sequenced (Genome Walking). As a result, it was found that the HeLa/neo cells were generated from the HeLa/puro cells wherein the transposon vector IR/DR-puro/LxpADb alone was inserted by simultaneous introduction of pCAGGS/Cre and pLx/GFP/neo/pA(−) which induced recombination on the Lox sequences to replace the region flanked by the Lox sequences of IR/DR-puro/LxpADb (an expression cassette of a puromycin resistant enzyme gene) with the region flanked by the Lox sequences of pLx/GFP/neo/pA(−) (expression cassettes of GFP and neo genes).

Besides, it was found that the outside portions within 5'- and 3'-TIR sequences inserted into chromosomal DNAs of Single/HeLa/neo cells were identical to those of IR/DR-puro/ LxpADb. It was also found that sequences further outside these sequences were identical to those on human Chromosome No. 12 as registered in nucleotide sequence data base (GeneBank) of NCBI of USA. This result indicates that the transposon vector IR/DR-puro/LxpADb introduced into HeLa cells was incorporated into Chromosome No. 12 of said HeLa cells by recombination mechanism normally occurring in the cells to provide Single/HeLa/puro cells, from which Single/HeLa/neo cells were generated by Cre-Lox recombination system.

Figure 23:
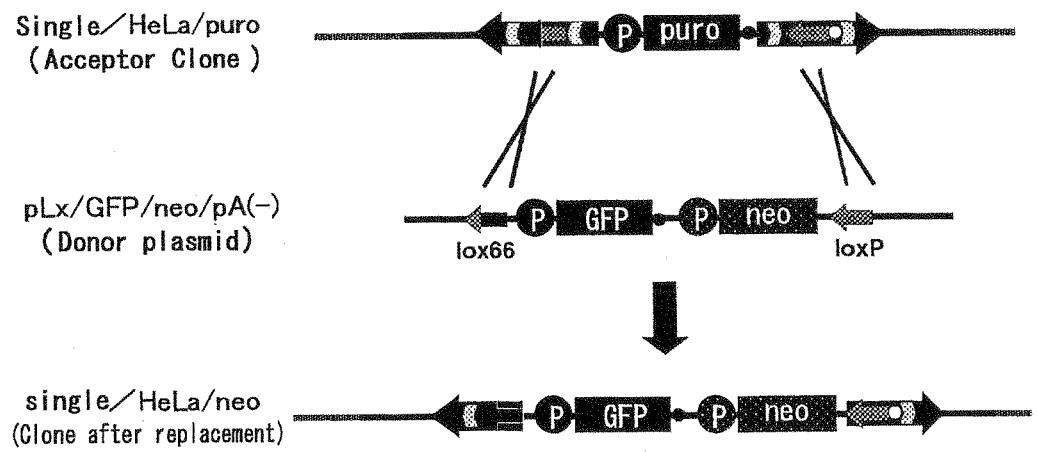
FIG. 23 is a schematic illustration showing a preparation of Single/HeLa/puro obtained by introduction of a single modified transposon vector IR/DR-puro/LxpADb and Single/HeLa/neo obtained therefrom by gene replacement with Cre-Lox system.

The results as described above suggests that it is possible to solely use a transposon vector wherein Lox sequences are inserted within 5'- and 3'-TIR sequences of a transposon gene so as to randomly insert said transposon vector into chromosomal DNAs and then to replace a gene within said transposon vector with another gene by Cre-Lox recombination system via the Lox sequences within the TIR sequences (FIG. 23).

Figure 24:
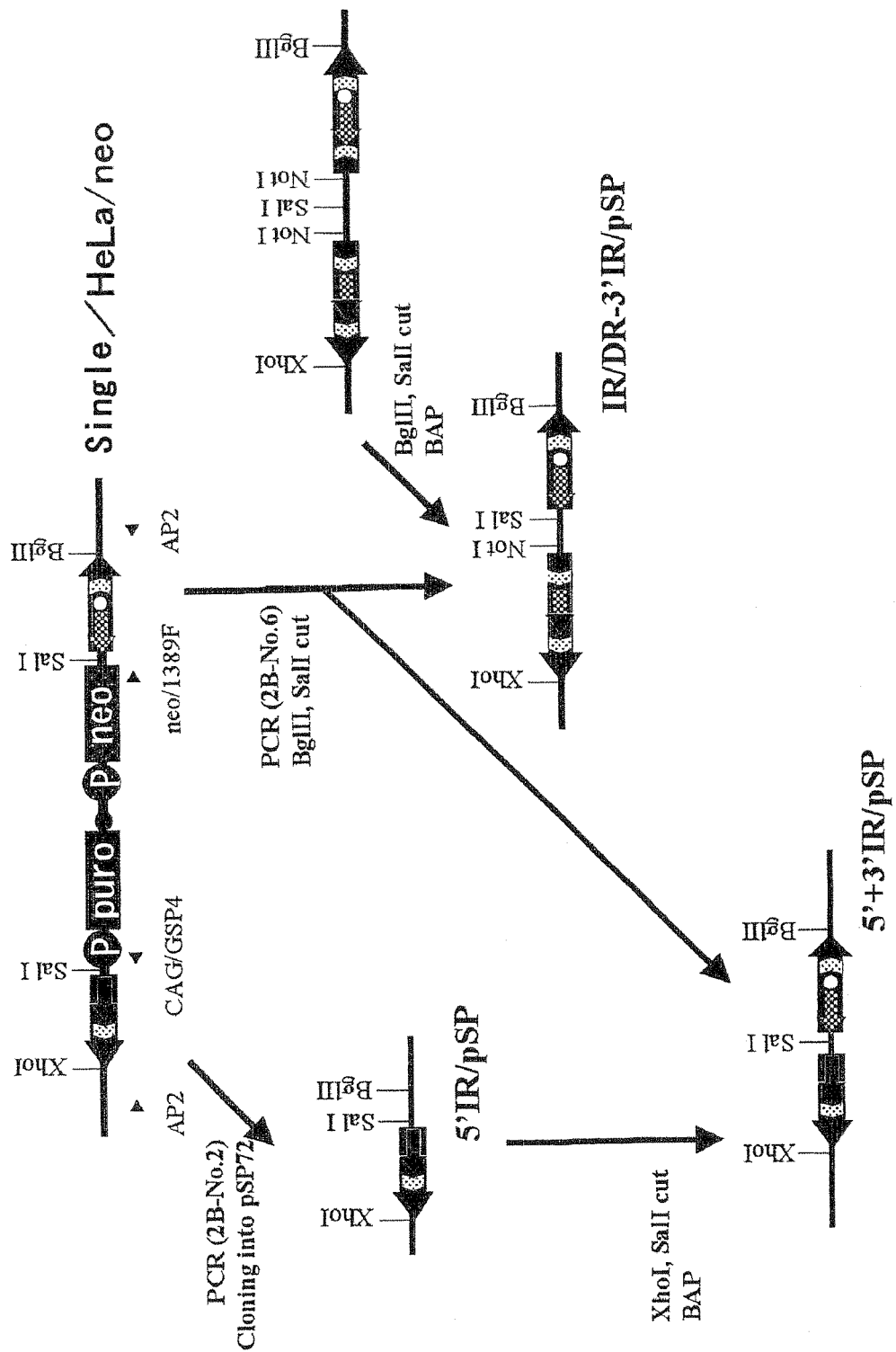
FIG. 24 is a schematic illustration showing construction of a modified transposon vector wherein TIR sequences are destroyed by removing the inner DR sequences within TIR sequences with Cre-Lox system.

(3) Modified Transposon Vector with Destroyed TIR Sequence and Construction of Plasmid for Assessing Transposon Activity of Modified Transposon Vector Clones (2B-No. 2 and 2B-No. 6) bearing a DNA fragment having a portion of 5'-TIR sequence and a DNA fragment having a portion of 3'-TIR sequence, respectively, after gene replacement by Cre-Lox recombination system, obtained by Genome Walking as described in Example 9(2) possess destroyed TIR sequences as a consequence of replacement reaction. Using these two clones, two kinds of transposon vectors, i.e. one with 5'-TIR sequence being destroyed and the other with both 5'- and 3'-TIR sequences being destroyed, were constructed as illustrated in the scheme of FIG. 24.

First, a fragment of about 170 bp was obtained by digestion of 2B-No. 6 with restriction enzymes SalI and BglII and inserted into IR/DR-Ad/LxpADb, which has previously been digested with the same restriction enzymes and then BAP treated, to provide a transposon vector IR/DR-3'IR/pSP wherein 3'-TIR sequence alone was destroyed. Next, 3'IR/ DR-3'IR/pSP was digested with restriction enzyme SalI and then BAP treated and thereto was inserted a DNA fragment of about 1.7 kbp obtained by digestion of pPGKpuro with the same restriction enzyme and BAP treatment to construct a plasmid IR/DR-3'IR/puro for assessing the transposon activity.

Next, a fragment of about 160 bp was obtained by digestion of 2B-No. 2 with restriction enzymes XhoI and SalI and inserted into a cloning vector pSP72, which has previously been digested with the same restriction enzymes and then BAP treated, to provide 5'IR/pSP. 5'IR/pSP was then digested with restriction enzymes SalI and BglII and then BAP treated and thereto was inserted a DNA fragment of about 170 bp obtained by digestion of 2B-No. 6 with the same restriction enzymes and BAP treatment to construct a modified transposon vector 5'+3'IR/pSP wherein both 5'- and 3'-TIR sequences were destroyed. Besides, for assessing the transposon activity in HeLa cells, 5'+3'IR/pSP was digested with restriction enzyme SalI and then BAP treated and thereto was inserted a DNA fragment of about 1.7 kbp obtained by digestion of pPGKpuro with the same restriction enzyme and BAP treatment to construct a plasmid 5'+3'IR/puro for assessing the transposon activity.

(4) Effect to Transposon Activity by Destruction of TIR Sequence

IR/DR-3'IR/puro with 3'-TIR sequence being destroyed (constructed in Example 9(3)), 5'+3'IR/puro with both 5'- and 3'-TIR sequences being destroyed (constructed in Example 9(3)) and IR/DR-Ad/LxpADb bearing TIR sequences before gene replacement (constructed in Example 5(5)) were introduced into HeLa cells together with a transposase expression plasmid pCAGGS/SB (constructed in Example 2) as described in Example 7(2). On Day 2 after culture, the cells were recovered by trypsin treating, plated at $5\times10^5$ cells/dish of 10 cm diameter and drug selection was initiated on 10% complete medium containing 1 µg/ml puromycin. Ten days after initiation of drug selection, the dish was washed with Dulbecco's phosphate buffer. A solution (1 ml/dish) of 0.2% Crystal violet (KISHIDA CHEMICAL Co., Ltd.) in 20% methanol (Wako Pure Chemical Industries, Ltd.) was added to the dish to stain and fix the cells at room temperature for 30 min. The dish was then washed with tap water and, after air dry, a colony number was measured.

HeLa cells wherein both IR/DR-puro/LxpADb and a transposase expression plasmid pCAGGS/SB were introduced exhibited a significantly higher frequency of a colony number than those wherein IR/DR-puro/LxpADb alone was introduced whereas HeLa cells wherein both IR/DR-3'IR/puro and 5'+3'IR/puro were introduced exhibited no such a significantly higher frequency (Table 4). This result indicates that a gene replacement via Lox sequences under Cre-Lox gene expression system destroyed TIR sequences and, as a consequence of the destruction, the transposon activity was lost. This result also indicates that the loss of the transposon activity may occur by destruction of only one of 5'- and 3'-TIR sequences.

In Table 4, $C_{SB}$ indicates a colony number observed when both plasmid and pCAGGS/SB are introduced simultaneously whereas $C_N$ indicates a colony number observed when each plasmid alone is introduced.

TABLE 4

| Plasmid | TIR sequence | | $C_{SB}/C_N$ |
|---|---|---|---|
| | 5' | 3' | |
| IR/DR-puro/LxpADb | o | o | 22.9 |
| IR/DR-3'IR/puro | o | x | 0.8 |
| 5' + 3'IR/puro | x | x | 0.5 |

Note:
o: Maintained;
x: Destroyed

In view of the results as described above, a modified transposon vector of the present invention is characterized by that: (1) a foreign gene may be introduced into cells at a high rate; (2) foreign gene may inserted into a specific site (TA sequence) on chromosomal DNAs; (3) a gene of a large size may be inserted or replaced by Cre-Lox recombination system; and (4) the activity to transpose a gene inserted into chromosomal DNAs characteristic to a transposon may surely be suppressed.

Example 10

Figure 25:
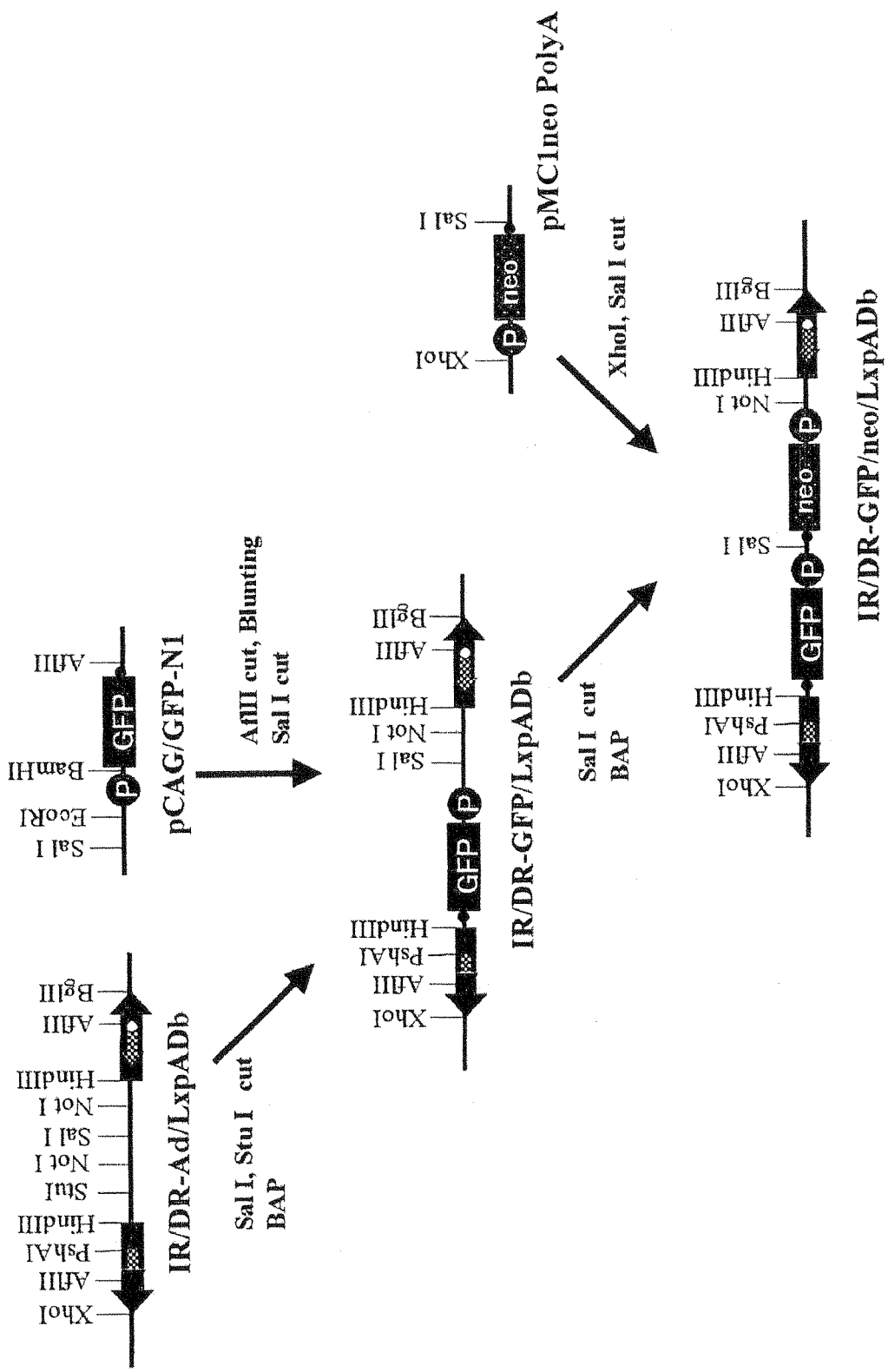
FIG. 25 is a schematic illustration showing construction of IR/DR-GFP/neo/LxpADb.

Use of Modified Transposon Vector System in Chicken Primordial Germ Cell (PGC) and Ontogenesis (1) Construction of Modified Transposon Plasmid for Introduction into PGC IR/DR-GFP/neo/LxpADb was constructed as described below wherein expression cassettes of GFP and of neomycin resistant gene were inserted into a modified transposon vector IR/DR-Ad/LxpADb constructed in Example 5(5) (FIG. 25).

pCAG/GFP-N1 constructed in Example 8(2) was digested with restriction enzyme AflII and, after the cleaved sites were blunted, were further digested with restriction enzyme SalI to recover a DNA fragment of about 2.8 kbp. The DNA fragment was inserted into IR/DR-Ad/LxpADb, which has previously been digested with restriction enzymes StuI and SalI and then BAP treated, to construct IR/DR-GFP/LxpADb. Then, a DNA fragment of about 1.2 kbp recovered after digestion of pMC1neo PolyA (STRATAGENE) with restriction enzymes XhoI and SalI was inserted into IR/DR-GFP/LxpADb, which has previously been digested with restriction enzyme SalI and then BAP treated, to construct IR/DR-GFP/neo/LxpADb.

(2) Isolation and Culture of Chicken PCG

Fertilized eggs immediately after laying purchased from Nisseiken Co., Ltd. were cultured in incubator (Showa Flanki). Two to three days after culture, blood was taken from chicken embryo at stage 12-15 as classified by Hamburger and Hamilton (J. Morphol., 88, 49-92, 1951) and isolated as described by Zhao et al. (Br. Poult. Sci., 44, 30-35, 2003). The isolated PGCs proved to possess the property of PGC based on reactivity with anti-SSEA-1 antibody and were maintained and cultured as described in WO 9606160.

(3) Introduction of Modified Transposon Plasmid into PGC

Introduction of a transposase expression plasmid pCAGGS/SB constructed in Example 2 and IR/DR-GFP/neo/LxpADb constructed in (1) above into PGCs was carried out as described below. To 250 µl Opti-MEM I Reduced-Serum Medium (INVITROGEN) were added 2.5 µg pCAGGS/SB and 2.5 µg IR/DR-GFP/neo/LxpADb. The mixture was added to a solution of 10 µl LF2000 (INVITROGEN) in 250 µl Opti-MEM I Reduced-Serum Medium (INVITROGEN) which has been kept to stand at room temperature for 5 min. and the resulting mixture was further kept to stand at room temperature for 20 min. The mixture was added to PGCs resuspended in a culture medium only defective in antibiotics and PGCs were cultured at 37° C. for 2-3 days in the presence of 5% $CO_2$. PGCs were then recovered and cultured in a culture medium containing 100 µg/ml of G418 (TaKaRa) to initiate selection of resistant clones.

Figure 26:
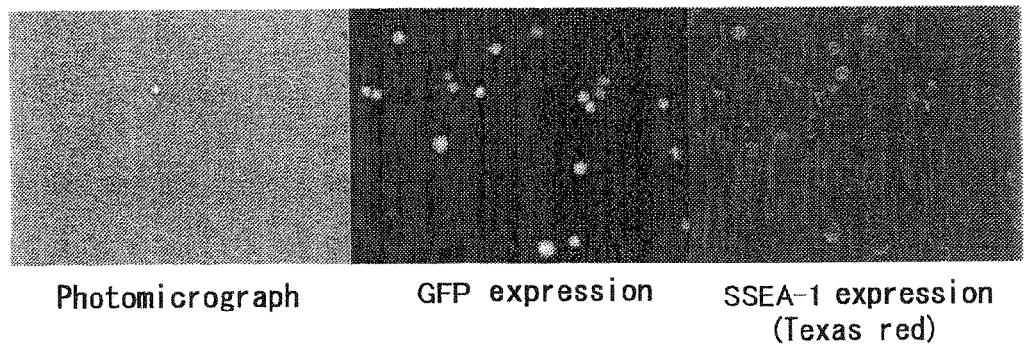
FIG. 26 shows results confirming GFP expression and reactivity with an anti-SSEA-1 antibody of PGCs grown after selection with G418 after introduction of IR/DR-GFP/neo/LxpADb.

After selection for about 2 weeks, the grown PGCs were assessed for expression of GFP and reactivity with a marker anti-SSEA-1 (FIG. 26). As a result, as shown in FIG. 26, it was found that most of the obtained cells emitted red fluorescence as a consequence of reaction with anti-mouse antibody labeled with texas red (Cosmo Bio Co., Ltd.) subsequent to reaction with a primary anti-SSEA-1 antibody (Cosmo Bio Co., Ltd.) to prove that the cells maintained property of PGC. Furthermore, GFP expression derived from the modified transposon plasmid IR/DR-GFP/neo/LxpADb was observed in about a half of the obtained PGCs.

(4) Infusion of PGC Wherein Modified Transposon Plasmid is Introduced and Detection of its Transposition into Gonadal Primordium The G418-resistant, GFP-expressing PCGs wherein modified transposon plasmid was introduced obtained in (3) above were infused into chicken embryo at stage 12-13 as described by Kuwana et al. (Experimental Medicine, 12(2), special number, 154-159, 1994). Briefly, an eggshell of a fertilized egg cultured for about 50-60 hours was removed as wide as manipulation is possible so that an extraembryonic blood vessel (marginal vein) may be observed under a stereoscopic microscope. The G418-resistant, GFP-expressing PCGs wherein modified transposon plasmid was introduced were suspended in a culture medium at about 500 cells/µl. About 2 µl of the suspension was taken in a glass tube (capillary tube) thinner than an extraembryonic blood vessel (marginal vein) and the glass tube (capillary tube) was pricked thereto in the direction of blood flow under a stereoscopic microscope to infuse the PGCs. After infusion, bubble was further infused to prevent reflux. The capillary tube was removed from the vessel and the fertilized egg was sealed with a book tape to cover the removed portion of the eggshell and transferred to an incubator for incubation with rotation stimulus.

Figure 27:
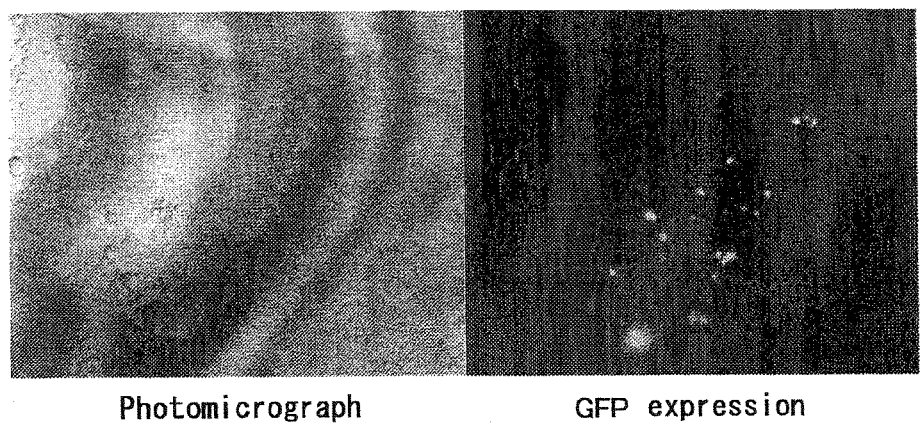
FIG. 27 shows accumulation of PGCs receiving IR/DR-GFP/neo/LxpADb in the gonadal primordium region of an embryo a day after introduction of the PGCs into the embryo.

A day after infusion, the incubated embryo infused with the PGCs wherein the modified transposon plasmid was introduced was cut off and the transposition capacity of the PGCs to a region estimated to be differentiated into the gonad (gonadal primordium) was investigated. As a result, transposition of the cells expressing GFP, i.e. the PGCs wherein the modified transposon plasmid was introduced, to the gonadal primordium could be detected as shown in FIG. 27.

Figure 28:
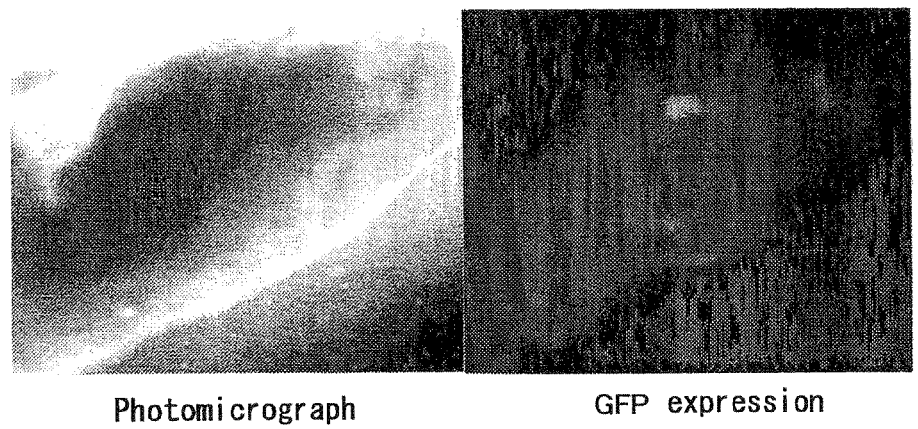
FIG. 28 shows expression of GFP in the gonad of chicken hatched from the embryo into which PGCs receiving IR/DR-GFP/neo/LxpADb is introduced.

(5) Hatching of Egg Infused with PGC Wherein Modified Transposon Plasmid is Introduced and Detection of GFP Expression in Gonad Sixteen embryos infused with the PGCs wherein the modified transposon plasmid was introduced as described in (4) above were transferred to an incubator (MURAI INCUBATOR) on Day 17 after initiation of incubation and further incubated for 3 days. After 3 day incubation, 8 chickens hatched from the 16 embryos. The gonad was removed from these 8 chickens and GFP expression was assessed to prove the GFP expression in 5 chickens (Table 5, FIG. 28).

TABLE 5

GFP expression in gonad of chickens hatched from embryos infused with PGC wherein IR/DR-GFP/neo/LxpADb is introduced

| Individual No. | Sex | GFP expression |
| --- | --- | --- |
| 1 | Male | − |
| 2 | Female | − |
| 3 | Female | + |
| 4 | Female | + |
| 5 | Female | + |
| 6 | Female | + |
| 7 | Female | + |
| 8 | Male | − |

Infusion of the PGCs wherein the modified transposon plasmid was introduced into embryos was repeated four times as described in (4) above. As a result of infusion into 131 embryos in total and their incubation, additional 6 chickens hatched. Other than these 6 chickens, the gonad was removed from 15 embryos which died immediately before hatching and whether GFP was expressed was investigated with fluorescent microscope. As a result, GFP expression derived from the modified transposon plasmid was observed in the gonad from 8 embryos (Table 6).

TABLE 6

GFP expression in gonad of embryos died immediately before hatching after infusion with PGC wherein IR/DR-GFP/neo/LxpADb is introduced

| No. of embryos observed | No. of embryos with GFP expression | A rate of GFP expression (%) |
|---|---|---|
| 15 | 8 | 53.3 |

Viewing that PGC is destined to differentiation into germ cells, i.e. sperms and ova, the fact that PGC wherein the modified transposon plasmid is introduced was got anchored in the gonad of embryo and an introduced gene was kept to be expressed implies that the introduced gene will be inherited to the next generations. Thus, the 6 chickens obtained in accordance with the present invention imply that it is possible to prepare a genetically recombined chicken from PGC wherein a modified transposon plasmid is introduced. In addition, from a fertilized egg laid by a genetically recombined chicken wherein a modified transposon plasmid is introduced, additional insertion or replacement of another foreign gene in PGC from said fertilized egg is possible by Cre-Lox recombination system.

INDUSTRIAL APPLICABILITY

A GFP-producing cell obtained by using a modified transposon vector of the present invention may be utilized as a source for a GFP protein. Said cells may be cultured in a large scale and from its culture or homogenization a GFP protein may be prepared by a suitable purification procedure. Besides, in place of a GFP gene, another foreign genes may also be inserted to provide cells or animals producing a variety of foreign proteins, which may be utilized as a source for such foreign proteins.

The invention claimed is:

1. A modified transposon vector, comprising a nucleic acid fragment having the following features (a)-(b) or (a)-(c):
   (a) 5'- and 3'-terminal inverted repeat (TIR) sequences of a transposon gene;
   (b) a Lox sequence where a recombination reaction occurs is disposed between the two direct repeats (DR) of at least one of the DR regions present in each of the 5'- and 3'-TIR sequences of (a) such that transposon activity is retained, wherein the number of nucleotides between the two DRs is the same as that before said Lox is disposed between the two DRs, and wherein said Lox allows for destruction of the transposon activity through deletion, insertion or replacement reaction to prevent re-transposition from occurring; and
   (c) a restriction enzyme recognition site or an expression cassette of a foreign gene disposed between the 5'- and 3'-TIR sequences of (a).

2. The modified transposon vector of claim 1 wherein the 5'- and 3'-TIR sequences of a transposon gene are SEQ ID NOs: 1 and 2, respectively.

3. The modified transposon vector of claim 1, wherein at least one of the Lox sequence is a mutated Lox sequence.

4. The modified transposon vector of claim 3 wherein said mutated Lox sequence is selected from the group consisting of Lox71, Lox66, Lox2272 and Lox511 sequences.

5. The modified transposon vector of claim 4, wherein Lox71, Lox66, Lox2272 and Lox511 sequences are SEQ ID NOs: 4, 5, 6 and 7, respectively.

6. A method for producing a foreign protein, comprising
   (i) introducing together an expression plasmid encoding transposase and a modified transposon vector comprising a nucleic acid fragment having the following features (a)-(c) into isolated host cells, wherein features (a)-(c) are:
   (a) 5'- and 3'-TIR sequences of a transposon gene;
   (b) a Lox sequence where a recombination reaction occurs is disposed between the two direct repeats (DR) of at least one of the DR regions present in each of the 5'- and 3'-TIR sequences of (a) such that transposon activity is retained, wherein the number of nucleotides between the two DRs is the same as that before said Lox is disposed between the two DRs, and wherein at least one of said Lox sequence is a mutated Lox sequence that allows for destruction of the transposon activity through insertion or replacement reaction to prevent re-transposition from occurring; and (c) an expression cassette of a foreign gene disposed between the 5'- and 3'-TIR sequences of (a), (ii) cloning the resulting transformed isolated host cells comprising the modified transposon vector and the expression plasmid encoding transposase gene, (iii) introducing into the cloned transformed host cells an expression plasmid encoding Cre and an expression cassette of a foreign gene flanked by the Lox sequence where a recombination reaction occurs as described in (i)(b) above at either end or at both ends, and (iv) culturing the cells of step (iii) expressing the foreign gene(s) to produce the foreign protein encoded by the foreign gene(s).

7. The method of claim 6, wherein the 5'- and 3'-TIR sequences of a transposon gene are SEQ ID NOs: 1 and 2, respectively.

8. The method of claim 6, wherein said mutated Lox sequence is selected from the group consisting of Lox71, Lox66, Lox2272 and Lox511 sequences.

9. The method of claim 8, wherein Lox71, Lox66, Lox2272 and Lox511 sequences are SEQ ID NOs: 4, 5, 6 and 7, respectively.

10. The method of claim 6, wherein said plasmid encoding transposase gene is contained in said modified transposon vector.

11. The method of claim 6, wherein said plasmid encoding Cre gene is contained in said expression cassette of a foreign gene.

12. The method of claim 6, wherein said isolated host cells are selected from the group consisting of HeLa, Vero, CHO, 293, BHK and SP2/0 cells.

13. An isolated cell comprising the modified transposon vector of claim 1.

14. An isolated cell comprising the modified transposon vector of claim 2.

15. An isolated cell comprising the modified transposon vector of claim 3.

16. An isolated cell comprising the modified transposon vector of claim 4.

17. An isolated cell comprising the modified transposon vector of claim 5.

* * * * *

UNITED STATES PATENT AND TRADEMARK OFFICE
CERTIFICATE OF CORRECTION

| | |
|---|---|
| PATENT NO. | : 9,175,295 B2 |
| APPLICATION NO. | : 11/994982 |
| DATED | : November 3, 2015 |
| INVENTOR(S) | : Kazuyoshi Kaminaka et al. |

It is certified that error appears in the above-identified patent and that said Letters Patent is hereby corrected as shown below:

On the title page item (86), delete "PCT/JP2006/013302" and insert --PCT/JP2006/313302--.

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 46

<210> SEQ ID NO 1
<211> LENGTH: 292
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Transposon Tcl/mariner

<400> SEQUENCE: 1
tacagttgaa gtcggaagtt tacatacact taagttggag tcattaaaac tcgtttttca      60
actacaccac aaatttcttg ttaacaaaca atagttttgg caagtcagtt aggacatcta     120
ctttgtgcat gacacaagtc atttttccaa caattgttta cagacagatt atttcactta     180
taattcactg tatcacaatt ccagtgggtc agaagtttac atacactaag ttgactgtgc     240
ctttaaacag cttggaaaat tccagaaaat gatgtcatgg ctttagaagc tt             292

<210> SEQ ID NO 2
<211> LENGTH: 303
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Transposon Tcl/mariner

<400> SEQUENCE: 2
tacagttgaa gtcggaagtt tacatacacc ttagccaaat acatttaaac tcactttttc      60
acaattcctg acatttaatc cgagtaaaga ttccctgtct taaggtcagt taggatcacc     120
actttatttt aagaatgtga aatgtcagaa tactagtaga gagaatgatt catttcagct     180
tttatttctt tcatcacatt cccagtgggt cagaagttta catacactca attagtattt     240
ggtagcattg cctttaaatt gtttaacctg ggtcaaacat ttcgggtagc cttccacaag     300
ctt                                                                   303

<210> SEQ ID NO 3
```

```
<211> LENGTH: 34
<212> TYPE: DNA
<213> ORGANISM: Artificial Sequence
<220> FEATURE:
<223> OTHER INFORMATION: Synthetic

<400> SEQUENCE: 3
ataacttcgt atagcataca ttatacgaag ttat                               34

<210> SEQ ID NO 4
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Modified sequence of phage LoxP

<400> SEQUENCE: 4
taccgttcgt atagcataca ttatacgaag ttat                               34

<210> SEQ ID NO 5
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Modified sequence of phage LoxP

<400> SEQUENCE: 5
ataacttcgt atagcataca ttatacgaac ggta                               34

<210> SEQ ID NO 6
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Modified sequence of phage LoxP

<400> SEQUENCE: 6
ataacttcgt ataggatact ttatacgaag ttat                               34

<210> SEQ ID NO 7
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Modified sequence of phage LoxP

<400> SEQUENCE: 7
ataacttcgt atagtataca ttatacgaag ttat                               34

<210> SEQ ID NO 8
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<223> OTHER INFORMATION: Primer for amplifying transposon gene by PCR

<400> SEQUENCE: 8
tacagttgaa gtgtaagttt a                                              21

<210> SEQ ID NO 9
<211> LENGTH: 103
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sense primer for amplifying 5'RgDR/pSP by PCR

<400> SEQUENCE: 9
cagttgaagt cggaagttta catacactta agttggagtc attaaaactc gttttcaac    60 tacaccacaa atttcttgtt aacaaacaat agttttggca agt                    103

<210> SEQ ID NO 10
<211> LENGTH: 86
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense primer for amplifying 5'RgDR/pSP by
      PCR

<400> SEQUENCE: 10
agaagcttct aaagccatga catcattttc tggaattttc caagctgttt aaaggcacag    60
tcaacttagt gtatgtaaac ttctga                                         86

<210> SEQ ID NO 11
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 5' TIR sequence of
      transposon gene by PCR

<400> SEQUENCE: 11
acacttaagt tggagtcatt aaaactcgt                                      29

<210> SEQ ID NO 12
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 5' TIR sequence of
      transposon gene by PCR

<400> SEQUENCE: 12
attgttggaa aaatgacttg tgtcatgcac aaagtagatg tcctaactga cttgcca       57

<210> SEQ ID NO 13
<211> LENGTH: 78
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: Primer for repairing 5' TIR sequence of
      transposon gene by PCR

<400> SEQUENCE: 13
agtcattttt ccaacaattg tttacagaca gattatttca cttataattc actgtatcac    60
aattccagtg ggtcagaa                                                  78

<210> SEQ ID NO 14
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 5' TIR sequence of
      transposon gene by PCR

<400> SEQUENCE: 14
gaagcttcta aagccatgac atcattttct ggaat                               35

<210> SEQ ID NO 15
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 3' TIR sequence of
      transposon gene by PCR

<400> SEQUENCE: 15
tggccatcac aaagctctga cctcaatcct atagaaagga ggaatgagcc aaaattcacc    60
caacttatt                                                            69

<210> SEQ ID NO 16
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 3' TIR sequence of
      transposon gene by PCR

<400> SEQUENCE: 16
catcacattc ccagtgggtc agaagtttac atacactcaa ttagta                   46

<210> SEQ ID NO 17
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 3' TIR sequence of
      transposon gene by PCR

<400> SEQUENCE: 17
acccactggg aatgtgatga agaaataaa agctgaaatg aatcattctc tctact         56
```

```
<210> SEQ ID NO 18
<211> LENGTH: 110
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for repairing 3' TIR sequence of
      transposon gene by PCR

<400> SEQUENCE: 18
cagttgaagt cggaagttta catacacctt agccaaatac atttaaactc acttttcac      60 aattcctgac atttaatccg agtaaagatt ccctgtctta aggtcagtta              110

<210> SEQ ID NO 19
<211> LENGTH: 453
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Transposon Tcl/mariner

<400> SEQUENCE: 19
gaattcgccc tttacagttg aagtcggaag tttacataca cttaagttgg agtcattaaa     60
actcgttttt caactacacc acaaatttct tgttaacaaa caatagtttt ggcaagtcag    120
ttaggacatc tactttgtgc atgacacaag tcatttttcc aacaattgtt tacagacaga   180
ttatttcact tataattcac tgtatcacaa ttccagtggg tcagaagttt acatacacta   240
agttgactgt gcctttaaac agcttggaaa attccagaaa atgatgtcat ggctttagaa   300
gcttctgata ggctaattga cataatttga gtcaatagga ggtgtacctg tggatatatt   360
tcaaggccta ctttcaaact cagtgcctct ttgcttgacg tcatgggata atcaaaagaa   420
atcagccagg acctcgaaaa aaacattgta gac                                453

<210> SEQ ID NO 20
<211> LENGTH: 1064
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Transposon Tcl/mariner

<400> SEQUENCE: 20
gtagacctcc acaagtctgg ttcatcatca cgcagccgtc ataccgttca ggagggagat     60
gtgttctgtc tcctagagat gaacgttctt tggtgtgaaa cgtgcaactc aatcccagaa   120
caacagcaaa ggaccttgtg aagttgctgg aggaaatgga tacaaaagta tctatagcca   180
cagtaaaacg agtcctatat cgacataacc tgaaaggccg ctcagcaagg aagaagccac   240
tgttccaaaa ccgccataaa aaagccagac tacggtttgc aactgcacat cggggcaaag   300
atggtactat ttggagaaat gtcctctggt ctgatgagaa aaaatagaac tgtttgacca   360
taatgaccat cgttatgttt ggagggtaaa gggggggagc ttgcaagccg aagaacacca   420
tcccaaccgt gaagcacggg ggtggcagca cattgttgtg ggggtgcttt gcggcaggag   480
ggactggtgc acttcacaaa atagatgcg tcatgaggta ggaaaatcgc gtggatatat   540
tgaagcaaca tctcaagaca tcagtcagga agttaaaact tggtcgcaaa tgggtcttcc   600
```

```
aaatggacaa tgaccccaag catacttcca aagttgtggt aaaatggctt aaggacaaca      660
aagtcaaggt attggattgg ccatcacaaa gctctgacct caatcctata gaaaggagga      720
atgagccaaa attcacccaa cttattgtgg gaagcttgtg gaaggctacc cgaaatgttt      780
gacccaggtt aaacaattta aaggcaatgc taccaaatac taattgagtg tatgtaaact      840
tctgacccac tgggaatgtg atgaaagaaa taaaagctga aatgaatcat tctctctact      900
agtattctga catttcacat tcttaaaata aagtggtgat cctaactgac cttaagacag      960
ggaatcttta ctcggattaa atgtcaggaa ttgtgaaaaa gtgagtttaa atgtatttgg     1020
ctaaggtgta tgtaaacttc cgacttcaac tgaagggcga attc                      1064

<210> SEQ ID NO 21
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' primer for construction of adapter 5'IR/DR-
      Ad by PCR

<400> SEQUENCE: 21
agcttctgat agactaattg acatcatttg agtcaattgg aggtgtacct gtggatgtat       60
ttcaaggcct gcggccgcg                                                    79

<210> SEQ ID NO 22
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' primer for construction of adapter 5'IR/DR-
      Ad by PCR

<400> SEQUENCE: 22
tcgacgcggc cgcaggcctt gaaatacatc cacaggtaca cctccaattg actcaaatga       60
tgtcaattag tctatcaga                                                    79

<210> SEQ ID NO 23
<211> LENGTH: 88
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' primer for construction of adapter 3'IR/DR-
      Ad by PCR

<400> SEQUENCE: 23
agcttcccac aataagttgg gtgaattttg gctcattcct cctttctata ggattgaggt       60
cagagctttg tgatggccag cggccgcg                                          88

<210> SEQ ID NO 24
<211> LENGTH: 88
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: 3' primer for construction of adapter 3'IR/DR-
      Ad by PCR

<400> SEQUENCE: 24
tcgacgcggc cgctggccat cacaaagctc tgacctcaat cctatagaaa ggaggaatga    60
gccaaaattc acccaactta ttgtggga                                       88

<210> SEQ ID NO 25
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' primer for amplifying TA-Fs/R by PCR

<400> SEQUENCE: 25
ctcgagctcg gtaccctaca gttgaagtcg gaagtttaca tacact                   46

<210> SEQ ID NO 26
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' primer for amplifying TA-Fs/R by PCR

<400> SEQUENCE: 26
agatctagag gatcccctac agttgaagtc ggaagtttac atacacctta gcca          54

<210> SEQ ID NO 27
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sense primer for insertion of Lox71 into 5' TIR
      sequence of transposon by PCR

<400> SEQUENCE: 27
atttaggtga cactatagaa c                                              21

<210> SEQ ID NO 28
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense primer for insertion of Lox71 into 5'
      TIR sequence of transposon by PCR

<400> SEQUENCE: 28
atgacttgtg tcataacttc gtataatgta tgctatacga acggtaaact attgtttgtt    60
aacaagaaat                                                           70

<210> SEQ ID NO 29
<211> LENGTH: 83
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<223> OTHER INFORMATION: Antisense primer for insertion of LoxP into 3'
      TIR sequence of transposon by PCR

<400> SEQUENCE: 29
gtcttaaggt cagttaggat caccataact tcgtataatg tatgctatac gaagttatag      60
tagagagaat gattcatttc agc                                              83

<210> SEQ ID NO 30
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for insertion of LoxP and poly A signal
      sequences into 3'TIR sequence of transposon by PCR

<400> SEQUENCE: 30
cctgtcttaa gatttcctca ttttattata acttcgtata atgtatgcta tacga           55

<210> SEQ ID NO 31
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with XhoI recognition and Lox66
      sequences at 5' end and inside, respectively

<400> SEQUENCE: 31
tccgctcgag ataacttcgt atagcataca ttatacgaac ggtacgaatt caggcctgtc      60
gacggatcct                                                             70

<210> SEQ ID NO 32
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with BglII recognition and LoxP
      sequences at 5' end and inside, respectively

<400> SEQUENCE: 32
tccagatcta taacttggta taatgtatgc tatacgaagt tatggccagg atccgtcgac      60
aggcctgaat tc                                                          72

<210> SEQ ID NO 33
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' primer based on DNA sequence of salmon
      transposase gene

<400> SEQUENCE: 33
atgggaaaat caaagaaat cagccaaga                                         29
```

<210> SEQ ID NO 34
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' primer based on DNA sequence of a rainbow
      trout transposase gene

<400> SEQUENCE: 34
ttagtatttg gtagcattgc ctttaaat                                           28

<210> SEQ ID NO 35
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sense primer with XhoI recognition and Kozak
      sequences for amplifying SB transposase gene by PCR

<400> SEQUENCE: 35
ctcgagttat gggaaaatca aaagaaatca gcca                                   34

<210> SEQ ID NO 36
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense primer with BglII and SalI
      recognition sequences for amplifying SB transposase gene by PCR

<400> SEQUENCE: 36
aagatctgtc gacttagtat ttggtagcat tgccttta                               38

<210> SEQ ID NO 37
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sense primer for amplifying a Neo gene
      detection probe used in Southern blotting

<400> SEQUENCE: 37
agaaagtatc catcatggct gatgcaa                                           27

<210> SEQ ID NO 38
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense primer for amplifying a Neo gene
      detection probe used in Southern blotting

<400> SEQUENCE: 38
ctcgtcaaga aggcgataga aggcga                                          26

<210> SEQ ID NO 39
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sense primer for amplifying a Puro gene
      detection probe used in Southern blotting

<400> SEQUENCE: 39
acgcgtcgac atgaccgagt acaagcccac ggt                                  33

<210> SEQ ID NO 40
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Antisense primer for amplifying a Puro gene
      detection probe used in Southern blotting

<400> SEQUENCE: 40
acgcgtcgac atcgatgcgt caggcaccgg gcttgcgggt ca                        42

<210> SEQ ID NO 41
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for use of the 1st step Geneme Walking
      by PCR, attached to BD Genome Walker Universal Kit

<400> SEQUENCE: 41
gtaatacgac tcactatagg gc                                              22

<210> SEQ ID NO 42
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with CAG promoter for use of the 1st
      step Geneme Walking by PCR

<400> SEQUENCE: 42
gcatatgata cacttgatgt actgcca                                         27

<210> SEQ ID NO 43
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer for use of the 2nd step Geneme Walking
      by PCR, attached to BD Genome Walker Universal Kit

<400> SEQUENCE: 43

```
actatagggc acgcgtggt                                              19

<210> SEQ ID NO 44
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with CAG promoter for use of the 2nd
      step Geneme Walking by PCR

<400> SEQUENCE: 44
gcgggccatt taccgtaagt tatgta                                      26

<210> SEQ ID NO 45
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with a part of DNA sequence of neomycin-
      resistant gene for use of the 1st step Geneme Walking by PCR

<400> SEQUENCE: 45
gcgatgcctg cttgccgaat atcat                                       25

<210> SEQ ID NO 46
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer with a part of DNA sequence of neomycin-
      resistant gene for use of the 2nd step Geneme Walking by PCR

<400> SEQUENCE: 46
cgctatcagg acatagcgtt ggcta                                       25
```